(12) United States Patent
Jammalamadaka et al.

(10) Patent No.: US 10,815,246 B2
(45) Date of Patent: Oct. 27, 2020

(54) THAILANSTATIN ANALOGS

(71) Applicant: pH Pharma Co., Ltd., Seoul (KR)

(72) Inventors: Vasu Jammalamadaka, Dublin, CA (US); Kimberly Ann Tipton, San Francisco, CA (US); Sanjeev Satyal, San Carlos, CA (US); Hoyoung Huh, Portola Valley, CA (US)

(73) Assignee: pH Pharma Co., Ltd., Seoul (KR)

( * ) Notice: Subject to any disclaimer, the term of this patent is extended or adjusted under 35 U.S.C. 154(b) by 0 days.

(21) Appl. No.: 16/376,540

(22) Filed: Apr. 5, 2019

(65) Prior Publication Data
US 2019/0233430 A1  Aug. 1, 2019

Related U.S. Application Data

(62) Division of application No. 16/135,287, filed on Sep. 19, 2018, now Pat. No. 10,301,319.

(60) Provisional application No. 62/686,781, filed on Jun. 19, 2018, provisional application No. 62/561,060, filed on Sep. 20, 2017.

(51) Int. Cl.
| | |
|---|---|
| *C07D 493/10* | (2006.01) |
| *A61K 45/06* | (2006.01) |
| *C07D 493/04* | (2006.01) |
| *A61K 47/68* | (2017.01) |
| *A61P 35/00* | (2006.01) |

(52) U.S. Cl.
CPC ............ *C07D 493/10* (2013.01); *A61K 45/06* (2013.01); *A61K 47/6803* (2017.08); *A61K 47/6841* (2017.08); *A61K 47/6855* (2017.08); *A61P 35/00* (2018.01); *C07D 493/04* (2013.01)

(58) Field of Classification Search
CPC .......................... C07D 493/04; C07D 493/10; A61K 47/6841; A61K 47/6803; A61K 47/6855; A61P 35/00
See application file for complete search history.

(56) References Cited

U.S. PATENT DOCUMENTS

| | | |
|---|---|---|
| 7,521,541 B2 | 4/2009 | Eigenbrot et al. |
| 7,825,267 B2 | 11/2010 | Koide et al. |
| 8,309,599 B2 | 11/2012 | Koide et al. |
| 9,169,264 B2 | 10/2015 | Subramanyam et al. |
| 9,504,669 B2 | 11/2016 | Subramanyam et al. |
| 2012/0121615 A1 | 5/2012 | Flygare et al. |
| 2014/0134193 A1 | 5/2014 | Subramanyam et al. |
| 2016/0297831 A1 | 10/2016 | Ghosh |
| 2019/0084996 A1 | 3/2019 | Jammalamadaka |

FOREIGN PATENT DOCUMENTS

| | | |
|---|---|---|
| WO | 2014068443 A1 | 5/2014 |
| WO | 2015077370 A1 | 5/2015 |
| WO | 2017214423 A2 | 12/2017 |

OTHER PUBLICATIONS

Cancer and Metastasis Reviews (1998), 17(1), 91-106.*
Science (1999), vol. 286, 531-537.*
Arlotta, et al., "In-Depth Comparison of Lysine-Based Antibody-Drug Conjugates Prepared on Solid Support Versus in Solution", Antibodies 7(6), doi:10.3390/antib7010006, 17 pages (2018).
Doronina, et al., "Novel Peptide Linkers for Highly Potent Antibody—Auristatin Conjugate", Bioconjugate Chem 19, 1960-1963 (2008).
Ducry, et al., "Antibody-Drug Conjugates: Linking Cytotoxic Payloads to Monoclonal Antibodies", Bioconjugate Chem 21, 5-13 (2010).
Ghosh, et al., "Enantioselective Total Syntheses of FR901464 and Spliceostatin A and Evaluation of Splicing Activity of Key Derivatives", J Org Chem 79, 5697-5709 (2014).
He, et al., "Cytotoxic Spliceostatins from *Burkholderia* sp. and Their Semisynthetic Analogues", J Nat Prod 77, 1864-1870 (2014).
Junutula, et al., "Rapid identification of reactive cysteine residues for site-specific labeling of antibody-Fabs", Journal of Immunological Methods 332, 41-52 (2008).
Junutula, et al., "Site-specific conjugation of a cytotoxic drug to an antibody improves the therapeutic index", Nature Biotechnology 26(8), 925-932 (2008).
Liu, et al., "Genomics-guided discovery of thailanstatins A, B, and C as pre-mRNA splicing inhibitors and antiproliferative agents from Burkholderia thailandensis MSMB43", J Nat Prod 76, 685-693 (2013).
Nicolaou, et al., "Total Synthesis in Search of Potent Antibody-Drug Conjugate Payloads. From the Fundamentals to the Translational", Acc Chem Res, DOI:10.1021/acs.accounts.8b00537, 13 pages (2018).
Nicolaou, et al., "Total Synthesis of Thailanstatin A", J Am Chem Soc 138, 7532-7535 (2016).

(Continued)

*Primary Examiner* — Rebecca L Anderson
(74) *Attorney, Agent, or Firm* — Viksnins Harris Padys Malen LLP; Alexandra J. Baran

(57) ABSTRACT

The invention provides novel cytotoxic compounds and cytotoxic conjugates comprising these cytotoxic compounds and cell-binding agents. More specifically, this invention relates to novel thailanstatin A analogs, useful as cytotoxic small molecule toxins in antibody-drug conjugates (ADCs). The present invention further relates to compositions including these cytotoxic compounds and ADCs, and methods for using these toxins and ADCs to treat pathological conditions including cancer.

17 Claims, 1 Drawing Sheet

(56) References Cited

OTHER PUBLICATIONS

Patent Cooperation Treaty, International Searching Authority, Search Report and Written Opinion for PCT/US2018/051721, 12 pages, Nov. 27, 2018.

Puthenveetil, et al., "Multivalent peptidic linker enables identification of preferred sites of conjugation for a potent thialanstatin antibody drug conjugate", PLoS ONE 12(5), e0178452, 16 pages (2017).

Puthenveetil, et al., "Natural Product Splicing Inhibitors: A New Class of Antibody-Drug Conjugate (ADC) Payloads", Bioconjugate Chem 27, 1880-1888 (2016).

Shen, et al., "Conjugation site modulates the in vivo stability and therapeutic activity of antibody-drug conjugates", Nature Biotech 30(2), 184-191 (2012).

Sukumaran, et al., "Mechanism-Based Pharmacokinetic/Pharmacodynamic Model for THIOMAB™ Drug Conjugates", Pharm Res 32, 1884-1893 (2015).

\* cited by examiner

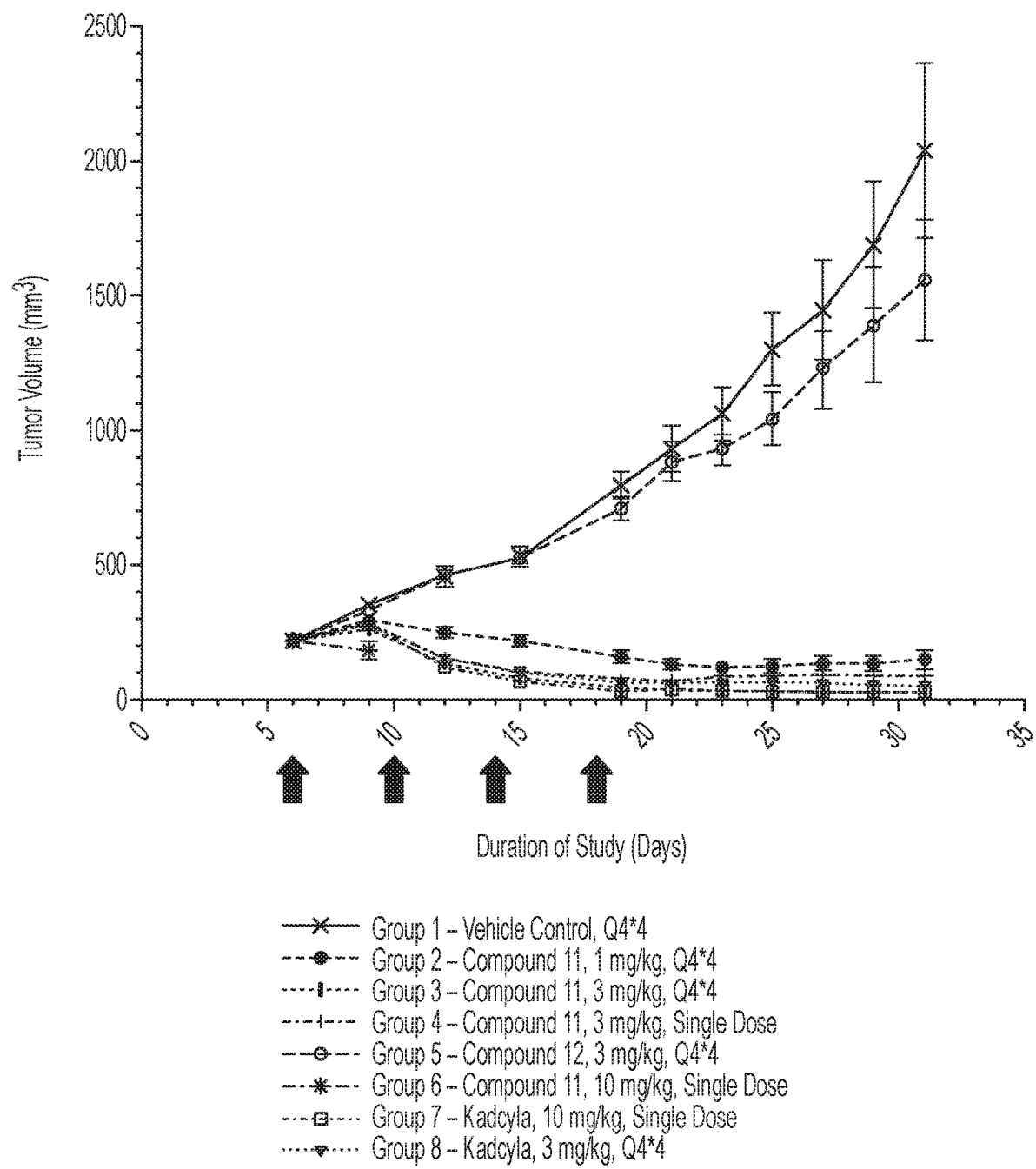

THAILANSTATIN ANALOGS

CROSS REFERENCE TO RELATED APPLICATIONS

This divisional application claims priority to U.S. application Ser. No. 16/135,287, filed Sep. 19, 2018 which is a non-provisional application filed under 37 C.F.R. § 153(b)(1), claiming priority under 35 U.S.C. § 119(e) to provisional application Ser. Nos. 62/561,060, filed Sep. 20, 2017, and 62/686,781, filed Jun. 19, 2018, the contents of which are herein incorporated by reference in their entirety.

TECHNICAL FIELD

The invention relates to novel cytotoxic compounds and cytotoxic conjugates comprising these cytotoxic compounds and cell-binding agents. More specifically, this invention relates to novel thailanstatin A analogs, useful as cytotoxic small molecule toxins in antibody-drug conjugates (ADCs). The present invention further relates to compositions including these cytotoxic compounds and ADCs, and methods for using these toxins and ADCs, to treat pathological conditions including cancer.

BACKGROUND OF THE INVENTION

Conjugation of drugs to antibodies, either directly or via linkers, involves a consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

Antibody-drug conjugates (ADC, also known as immunoconjugates) have demonstrated considerable utility as anti-cancer agents. In an ADC, a therapeutic agent (also referred to as the cytotoxic drug or toxin) is covalently linked to an antibody whose antigen is expressed by a cancer or other proliferative cell (tumor associated antigen). The antibody, by binding to the antigen, delivers the ADC to the cancer site. There, cleavage of the covalent link or degradation of the antibody leads to the release of the therapeutic agent. On the other hand, while the ADC is circulating in the blood system, the therapeutic agent is inactive because of its linkage to the antibody. Thus, the therapeutic agent used in an ADC can be much more potent than ordinary chemotherapeutic agents because of its highly localized release.

While a number of different drug classes have been tried for delivery via antibodies, only a few drug classes have proved efficacious as antibody-drug conjugates, while having a suitable toxicity profile. One successful drug class includes analogs of FR901464, such as spliceostatin C and thailanstatin A, which are extremely potent inhibitors of eukaryotic RNA splicing. These compounds bind tightly to the SF3b subunit of the U2 snRNA subcomplex, an essential component of the spliceosome (Puthenveetil, S., et al., Bioconjugate Chem., 2016, 27:1880-1888).

U.S. Pat. Nos. 9,169,264 and 9,504,669 (both Subramanyam et al.) disclose spliceostatin-based compounds useful as payloads in ADCs and payload-linker compounds useful in connection with ADCs. The patents further disclose use of these compounds in the treatment of pathological conditions including cancer.

SUMMARY OF THE INVENTION

The present invention relates to compounds and pharmaceutical compositions containing them, to their preparation, and to uses for the compounds, primarily but not exclusively anti-cancer agents.

According to one aspect, the present invention relates to a compound or compounds of Formula (I):

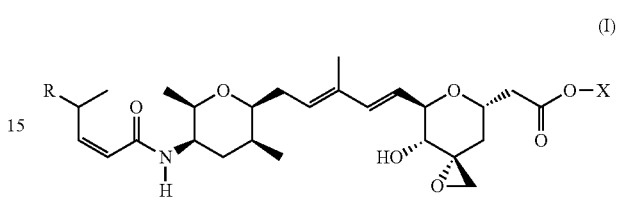

(I)

wherein:
R is selected from the group consisting of: —(CH$_2$)$_n$—R$^1$;
—C$_{5-6}$heteroaryl, optionally substituted with one or more of halogen, —CF$_3$, —C$_{1-6}$alkyl, and —O—C$_{1-6}$alkyl;
—C(R$^2$)=N—R$^3$; —CH(CF$_3$)NH(CH$_2$)$_m$CH$_3$;
—C(R$^a$R$^b$)NH(CH$_2$)$_m$CH$_3$;
—C(halogen)=CH(CH$_2$)$_m$CH$_3$; —SO$_2$—NH(CH$_2$)$_m$CH$_3$; —O(CO)-aryl; —O(CO)-heteroaryl;
—NR$^a$R$^b$; and —NH-heteroaryl;
wherein R$^1$ is —O—CR$^a$R$^b$(CH$_2$)$_m$CH$_3$ or —N—CR$^a$R$^b$(CH$_2$)$_m$CH$_3$;
wherein R$^a$ and R$^b$, together with the atoms to which they are joined, form a C$_{3-10}$ heterocyclyl ring;
R$^2$ is —CN or —NH(CH$_2$)$_m$CH$_3$;
R$^3$ is (CH$_2$)$_m$CH$_3$ or —O—(CH$_2$)$_m$CH$_3$;
X is —H or —CH$_3$;
each n is independently 1, 2, or 3; and
each m is independently 0, 1, 2, or 3;
or a pharmaceutically acceptable salt thereof.

According to another aspect, the present invention relates to a compound or compounds of Formula (II):

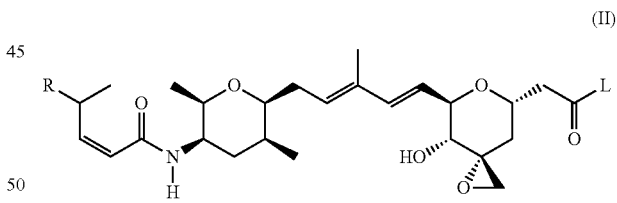

(II)

or a pharmaceutically acceptable salt thereof, wherein:
L is a linker;
R is selected from the group consisting of: —(CH$_2$)$_n$—R$^1$;
—C$_{5-6}$heteroaryl, optionally substituted
with one or more of halogen, —CF$_3$, —C$_{1-6}$alkyl, and —O—C$_{1-6}$alkyl;
—C(R$^2$)=N—R$^3$; —CH(CF$_3$)NH(CH$_2$)$_m$CH$_3$;
—C(R$^a$R$^b$)NH(CH$_2$)$_m$CH$_3$;
—C(halogen)=CH(CH$_2$)$_m$CH$_3$; —SO$_2$—NH(CH$_2$)$_m$CH$_3$; —O(CO)-aryl; —O(CO)-heteroaryl;
—NR$^a$R$^b$; and —NH-heteroaryl;
wherein R$^1$ is —O—CR$^a$R$^b$(CH$_2$)$_m$CH$_3$ or —N—CR$^a$R$^b$(CH$_2$)$_m$CH$_3$;
wherein R$^a$ and R$^b$, together with the atoms to which they are joined, form a C$_{3-10}$ heterocyclyl ring;

$R^2$ is —CN or —NH(CH$_2$)$_m$CH$_3$;
$R^3$ is —(CH$_2$)$_m$CH$_3$ or —O—(CH$_2$)$_m$CH$_3$;
each n is independently 1, 2, or 3; and
each m is independently 0, 1, 2, or 3.

According to a further aspect, the present invention relates to compound or compounds of Formula (III):

T-L'-Ab     (III)

or a pharmaceutically acceptable salt thereof, wherein:
L is a linker moiety;
T is a radical of Formula (I'):

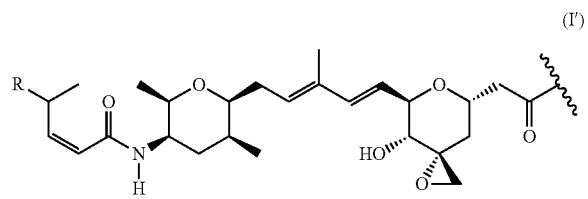

(I')

wherein:
R is selected from the group consisting of: —(CH$_2$)$_n$—R$^1$; —C$_{5-6}$heteroaryl, optionally substituted with one or more of halogen, —CF$_3$, —C$_{1-6}$alkyl, and —O—C$_{1-6}$alkyl; —C(R$^2$)=N—R$^3$; —CH(CF$_3$)NH(CH$_2$)$_m$CH$_3$; —C(R$^a$R$^b$)NH(CH$_2$)$_m$CH$_3$; —C(halogen)=CH(CH$_2$)$_m$CH$_3$; —SO$_2$—NH(CH$_2$)$_m$CH$_3$; —O(CO)-aryl; —O(CO)-heteroaryl; —NR$^a$R$^b$; and —NH-heteroaryl;
wherein R$^1$ is —O—CR$^a$R$^b$(CH$_2$)$_m$CH$_3$ or —N—CR$^a$R$^b$(CH$_2$)$_m$CH$_3$;
wherein R$^a$ and R$^b$, together with the atoms to which they are joined, form a C$_{3-10}$ heterocyclyl ring;
$R^2$ is —CN or —NH(CH$_2$)$_m$CH$_3$;
$R^3$ is —(CH$_2$)$_m$CH$_3$ or —O—(CH$_2$)$_m$CH$_3$;
each n is independently 1, 2, or 3;
each m is independently 0, 1, 2, or 3; and
Ab is an antibody.

According to still another aspect, the present invention relates to a pharmaceutical composition of a compound or compounds of Formula (I) or Formula (III), and/or a salt or salts thereof, comprising a therapeutically effective amount of the compound(s) or salt(s) and a pharmaceutically acceptable diluent, carrier or excipient. Such pharmaceutical compositions may additionally include a therapeutically effective amount of another chemotherapeutic agent known to those skilled in the art.

According to another aspect, the present invention relates to a method for the treatment of cancer comprising administering to a patient in need thereof a therapeutically effective amount of the compound of Formula (I) or Formula (III) and/or a salt or salts thereof, said amount being effective to kill or inhibit the proliferation of the tumor cells or cancer cells.

According to a further aspect, the present invention relates to a method of making a compound or Formula (III), the method comprising reacting an antibody with a compound of Formula (II).

According to another aspect, the present invention relates to a kit for treating cancer comprising the pharmaceutical composition of the invention and instructions for use.

Other objects of the invention may be apparent to one skilled in the art upon reading the following specification and claims.

BRIEF DESCRIPTION OF THE DRAWINGS

FIG. 1 shows mean+/−SEM (standard error of the mean) tumor volume measurements in NCI-N87-derived tumors in female BALB/c nude mice following treatment with various doses of Compound 10, Compound 11, Kadcyla® or vehicle alone. The black arrows indicate the days the mice were injected with test article.

DETAILED DESCRIPTION

This application is not limited to particular methodologies or the specific compositions described, as such may, vary. It is also to be understood that the terminology used herein is for the purpose of describing particular embodiments only, and is not intended to be limiting, because the scope of the present application will be limited only by the appended claims and their equivalents.

The present invention relates to novel thailanstatin analog compounds useful as cytotoxic small molecules in antibody-drug conjugates (ADCs), and toxin-linker compounds, alternatively known as drug-linker compounds, useful in connection with ADCs. The present invention further relates to compositions including these cytotoxic compounds and ADCs, and methods for using these toxins and ADCs, to treat pathological conditions including cancer.

Definitions and Abbreviations

Unless defined otherwise, all technical and scientific terms used herein have the same meaning as commonly understood by one of ordinary skill in the art to which this invention belongs. Although any methods and materials similar or equivalent to those described herein can be used in the practice or testing of the present application, the preferred methods and materials are now described.

The term "antibody" (or "Ab" or "AB") as used herein includes immunoglobulin (Ig) molecules. In certain embodiments, the antibody is a full-length antibody that comprises four polypeptide chains, namely two heavy chains (HC) and two light chains (LC) inter-connected by disulfide bonds. Each heavy chain is comprised of a heavy chain variable region (HCVR or VH) and a heavy chain constant region (CH). The heavy chain constant region is comprised of three domains, CH1, CH2, and CH3. Each light chain is comprised of a light chain variable region (LCVR or VL) and a light chain constant region, which is comprised of one domain, CL. The VH and VL regions can be further subdivided into regions of hypervariability, termed complementarity determining regions (CDRs). Interspersed with such regions are the more conserved framework regions (FRs). Each VH and VL is composed of three CDRs and four FRs, arranged from amino-terminus to carboxy-terminus in the following order: FR1, CDR1, FR2, CDR2, FR3, CDR3, and FR4.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller, et al., J. Immunology, 2003, 170:4854-4861). Antibodies may be murine, human, humanized, chimeric, or derived from other species. An antibody is a protein generated by the immune system that is capable of recognizing and binding to a specific antigen (Janeway, C., et al., Immuno Biology, 5th Ed., 2001, Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; minibodies (Olafsen et al., *Protein Eng. Design Sel.*, 2004, 17(4):315-323), fragments produced by a Fab expression library, anti-idiotypic (anti-Id) antibodies, CDR (complementary determining region), and epitope-binding fragments of any described herein which immunospecifically bind to cancer cell antigens, viral antigens or microbial antigens, single-chain antibody molecules; and multispecific antibodies formed from antibody fragments.

In certain embodiments, the antibody is IgG, IgA, IgE, IgD, or IgM. In certain embodiments, the antibody is IgG1, IgG2, IgG3, or IgG4; or IgA1 or IgA2.

In certain embodiments, the cell-binding agent is an "antigen-binding portion" of a monoclonal antibody, sharing sequences critical for antigen-binding with an antibody (such as huMy9-6 or its related antibodies described in U.S. Pat. Nos. 7,342,110 and 7,557,189, incorporated herein by reference).

As used herein, the term "antigen-binding portion" of an antibody (or sometimes interchangeably referred to herein as "antibody fragments"), include one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding portion" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab) monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; (v) a dAb (domain antibody) or sdAb (single domain antibody) fragment, which consists of a VH domain; and (vi) an isolated complementarity determining region (CDR). In certain embodiments, the antigen-binding portion is a sdAb (single domain antibody).

In certain embodiments, antigen-binding portion also include certain engineered or recombinant derivatives (or "derivative antibodies") that also include one or more fragments of an antibody that retain the ability to specifically bind to an antigen, in addition to elements or sequences that may not be found in naturally existing antibodies.

For example, although the two domains of the Fv fragment, VL and VH, are coded for by separate genes, they can be joined, using standard recombinant methods, by a synthetic linker that enables them to be made as a single protein chain in which the VL and VH regions pair to form monovalent molecules (known as single chain Fv (scFv). In all embodiments described herein, the N-terminum of an scFv may be a VH domain (i.e., N—VH-VL-C), or a VL domain (i.e., N-VL-VH-C).

Divalent (or bivalent) single-chain variable fragments (di-scFvs, bi-scFvs) can be engineered by linking two scFvs. This produces a single peptide chain with two VH and two VL regions, yielding a tandem scFvs (tascFv). More tandem repeats, such as tri-scFv, may be similarly produced by linking three or more scFv in a head-to-tail fashion.

In certain embodiments, scFvs may be linked through linker peptides that are too short (about five amino acids) for the two variable regions to fold together, forcing scFvs to dimerize, and form diabodies. Diabodies may be bi-specific or monospecific. Diabodies have been shown to have dissociation constants up to 40-fold lower than corresponding scFvs, i.e., having a much higher affinity to the target.

Still shorter linkers (one or two amino acids) lead to the formation of trimers, or so-called triabodies or tribodies. Tetrabodies have also been produced similarly. They exhibit an even higher affinity to their targets than diabodies. Diabodies, triabodies, and tetrabodies are sometimes collectively called "AVIBODY™" cell binding agents (or "AVIBODY" in short). That is, AVIBODY having two, three, or four Target Binding Regions (TBRs) are commonly known as Dia, Tria- and Tetrabodies. See, for example, U.S. Publication Nos. 2008/0152586 and 2012/0171115 for details, the entire teachings of which are incorporated herein by reference.

All of these formats can be composed from variable fragments with specificity for two or more different antigens, in which case they are types of bi- or multi-specific antibodies. For example, certain bispecific tandem di-scFvs, are known as bi-specific T-cell engagers (BiTEs). In certain embodiments, each scFv in the tandem scFv or diabody/triabody/tetrabody may have the same or different binding specificity, and each may independently have an N-terminal VH or N-terminal VL.

Fcabs are antibody fragments engineered from the Fc constant region of an antibody. Fcabs can be expressed as soluble proteins, or they can be engineered back into a full-length antibody, such as IgG, to create mAb2. A mAb2 is a full-length antibody with an Fcab in place of the normal Fc region. With these additional binding sites, mAb2 bispecific monoclonal antibodies can bind two different targets at the same time.

Natural antibodies are mono-specific, but bivalent, in that they express two identical antigen-binding domains. In contrast, in certain embodiments, certain engineered antibody derivatives are bi- or multi-specific molecules possess two or more different antigen-binding domains, each with different target specificity. Bispecific antibodies can be generated by fusing two antibody-producing cells, each with distinct specificity. These "quadromas" produced multiple molecular species, as the two distinct light chains and two distinct heavy chains were free to recombine in the quadromas in multiple configurations. Since then, bispecific Fabs, scFvs and full-size mAbs have been generated using a variety of technologies (see above).

The dual variable domain immunoglobulin (DVD-Ig) protein is a type of dual-specific IgG that simultaneously target two antigens/epitopes. The molecule contains an Fc region and constant regions in a configuration similar to a conventional IgG. However, the DVD-Ig protein is unique in that each arm of the molecule contains two variable domains (VDs). The VDs within an arm are linked in tandem and can possess different binding specificities.

Trispecific antibody derivative molecules can also been generated by, for example, expressing bispecific antibodies with two distinct Fabs and an Fc. One example is a mouse IgG2a anti-Ep-CAM, rat IgG2b anti-CD3 quadroma, called BiUII, which is thought to permit the co-localization of tumor cells expressing Ep-CAM, T cells expressing CD3, and macrophages expressing $FC_\delta RI$, thus potentiating the costimulatory and anti-tumor functions of the immune cells.

Probodies are fully recombinant, masked monoclonal antibodies that remain inert in healthy tissue, but are activated specifically in the disease microenvironment (e.g., through protease cleavage by a protease enriched or specific in a disease microenvironment). Similar masking techniques can be used for any of the antibodies or antigen-binding portions thereof described herein.

An intrabody is an antibody that has been modified for intracellular localization, for working within the cell to bind to an intracellular antigen. The intrabody may remain in the cytoplasm, or may have a nuclear localization signal, or may have a KDEL sequence for ER targeting. The intrabody may be a single-chain antibody (scFv), nodified immunoglobulin VL domains with hyperstability, selected antibody resistant to the more reducing intracellular environment, or expressed as a fusion protein with maltose binding protein or other stable intracellular proteins. Such optimizations have improved the stability and structure of intrabodies, and may have general applicability to any of the antibodies or antigen-binding portions thereof described herein.

The antigen-binding portions or derivative antibodies of the invention may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody from which they are derived/engineered. Sequences within these regions may contain conservative amino acid substitutions, including substitutions within the CDR regions. In certain embodiments, there is no more than 1, 2, 3, 4, or 5 conservative substitutions. In an alternative, the antigen-binding portions or derivative antibodies have a light chain region and/or a heavy chain region that is at least about 90%, 95%, 99% or 100% identical to an antibody from which they are derived/engineered. These antigen-binding portions or derivative antibodies may have substantially the same binding specificity and/or affinity to the target antigen compared to the antibody. In certain embodiments, the $K_d$ and/or $k_{off}$ values of the antigen-binding portions or derivative antibodies are within 10-fold (either higher or lower), 5-fold (either higher or lower), 3-fold (either higher or lower), or 2-fold (either higher or lower) of an antibody described herein.

In certain embodiments, the antigen-binding portions or derivative antibodies may be derived/engineered from fully human antibodies, humanized antibodies, or chimeric antibodies, and may be produced according to any art-recognized methods.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

A "cysteine engineered antibody" is an antibody in which one or more residues of an antibody are substituted with cysteine residues. In accordance with the present disclosure, the thiol group(s) of the cysteine engineered antibodies can be conjugated to a thailanstatin analog toxin of Formula I or a drug-linker Formula II compound to form an antibody-drug conjugate (ADC) compound. In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an ADC, as described further herein. For example, a cysteine engineered antibody may be an antibody with a single mutation of a non-cysteine native residue to a cysteine in the light chain (e.g., G64C, K149C or R142C according to Kabat numbering) or in the heavy chain (e.g., D101C or V184C or T205C according to Kabat numbering). In specific examples, a cysteine engineered antibody has a single cysteine mutation in either the heavy or light chain such that each full-length antibody (i.e., an antibody with two heavy chains and two light chains) has two engineered cysteine residues. Cysteine engineered antibodies and preparatory methods are disclosed by U.S. Published Application No. 2012/0121615, U.S. Pat. No. 7,521, 541; Shen, B. et al., *Nat. Biotechnol.*, 2012, 30(2):184-189;

Sukumaran, et al., Pharm. Res., 2015, 32:1884-1893 (incorporated by reference herein in their entirety).

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR). The therapeutically effective amount will vary according to the compound, the severity of the disease or disorder being treated, and the age, weight, etc., of the patient being treated.

The term "substantial amount" refers to a majority, i.e. greater than 50% of a population, of a mixture or a sample.

The term "cytotoxic activity" or "cytotoxicity" refers to a cell-killing, a cytostatic or an antiproliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

The term "patient" refers to a mammal, preferably a human being.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

Unless otherwise indicated, the term "alkyl" by itself or as part of another term refers to a straight chain or branched, saturated hydrocarbon having the indicated number of carbon atoms (e.g., "$C_1$-$C_8$" alkyl refer to an alkyl group having from 1 to 8 carbon atoms). When the number of carbon atoms is not indicated, the alkyl group has from 1 to 8 carbon atoms, preferably from 1 to 6 carbon atoms. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene —$CH_2CH_2$—), 1,3-propylene (—$CH_2CH_2CH_2$—), 1,4-butylene (—$CH_2CH_2CH_2CH_2$—), and the like. A "$C_1$-$C_{10}$" straight chain alkylene is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene. In certain embodiments of the invention, alkylenes have from 1 to 9, from 1 to 8, from 1 to 7, and from 1 to 6 carbons.

The term "compound" or "compounds" as used herein refer to thailanstatin analogs, and includes any specific compounds encompassed by generic formulae disclosed herein. The compounds may be identified either by their chemical structure and/or chemical name. When the chemical structure and chemical name conflict, the chemical structure is determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when the stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, and $^{18}$O. Compounds may exist in unsolvated forms as well as solvated forms, including hydrated forms and as N-oxides. In general, the hydrated, solvated and N-oxide forms are within the scope of the present disclosure. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si, S and/or P, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive.

"Halo" or "halogen" refers to fluoro, chloro, bromo and iodo.

"Halo($C_{1-6}$-alkyl)" refers to $C_{1-6}$-alkyl groups substituted with 1 to 3 or 1 to 2 halo groups, wherein $C_{1-6}$-alkyl and halo are as defined herein. The term includes, for example, $CF_3$.

The term "epoxy", or "epoxy group" or "epoxy residue" refer to a three member ring comprising to carbon atoms and an oxygen atom linked by single bonds. Accordingly, the term "epoxide" refers to a compound that comprise at least one epoxy group as defined.

Unless otherwise indicated, "aryl," by itself or an part of another term, means a substituted or unsubstituted monovalent aromatic hydrocarbon radical of 6 to 20 carbon atoms, preferably from 6 to 14 carbon atoms, derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably between 6 to 12 carbon atoms. A substituted aromatic group (e.g., an aryl group) can be substituted with one or more, preferably 1 to 5, of the following groups: $C_1$-$C_8$alkyl, —O—($C_1$-$C_8$alkyl), —C(O)R', —OC(O)R', —C(O)OR, —C(O)NH$_2$, —C(O)NHR', —C(O)N(R')$_2$, —NHC(O)R', —S(O)$_2$R', —S(O)R', —OH, halogen, —NH(R'), —N(R)$_2$ and —CN; wherein each R' is independently selected from —H, $C_1$-$C_8$ alkyl, $C_1$-$C_8$ heteroalkyl and aryl. In some embodiments, a substituted aromatic group can further include one or more of: —NHC(=NH)NH$_2$, —NHCONH$_2$, —S(=O)$_2$R' and —SR'.

The term "heteroaryl" as used herein refers to an aromatic heterocycle ring of 5 to 14 members, such as 5 to 6 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. Heteroaryls are optionally substituted. Typical substituents include, but are not limited to, —X, —R, —O—, —OR, —SR, —S—, —NR$_2$, —NR$_3$, =NR, —CX$_3$, —CN, —OCN, —NRC(=O)R, —C(=O)NR$_2$, —SO$_3$H, —S(=O)$_2$R, —OS(=O)$_2$OR, —S(=O)$_2$NR, —S(—O)R, —OP(=)(OR)$_2$, —P(=O)(OR)$_2$, PO$_3$H$_2$, —C(=O)R, —C(=O)X, —C(=S)R, —CO$_2$R, —CO—, —C(=S)OR, —C(=O)SR, —C(=S)SR, —C(=O)NR$_2$, —C(=S)NR$_2$, —C(=NR)NR$_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each R is independently —H or $C_1$-$C_6$ alkyl.

The term "hydroxy" refers to the group —OH.

The term "substituted alkyl" means an alkyl in which one or more hydrogen atoms are each independently replaced with a substituent. Typical substituents include, but are not limited to, —X, —R, —O—, —OR, —SR, —S—, —NR$_2$, —NR$_3$, =NR, —CX$_3$, —CN, —OCN, =N$_2$, —NRC(=O)R, —C(=O)NR$_2$, —SO$_3$—, —SO$_3$H, —S(—O)$_2$R, —OS(O=)$_2$OR, —S(=O)$_2$NR, —S(=O)R, —OP(=O)(OR)$_2$, —P(=O)(OR)$_2$, —PO$_{32}$—, PO$_3$H$_2$, —AsO$_2$H$_2$, —C(=O)R, —C(=O)X, —C(=S)R, —CO$_2$R, —CO$_2$, —C(=S)OR, —C(=O)SR, —C(=S)SR, —C(=O)NR$_2$, —C(=S)NR$_2$, —C(=NR)NR$_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each R is independently —H or $C_1$-$C_8$ alkyl. A substituted alkyl substituted with a halogen is sometimes referred to herein as a haloalkyl. Aryl, alkylene, heteroalkylene and other groups containing or not containing an alkyl or alkylene moiety as described herein may also be similarly substituted.

Unless otherwise indicated, "aralkyl" by itself or part of another term, means an alkyl group, as defined above, substituted with an aryl group, as defined above.

Unless otherwise indicated, "$C_3$-$C_8$heterocyclyl" by itself or as part of another term, refers to a monovalent or divalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. Similarly, unless otherwise indicated, "$C_3$-$C_{10}$heterocyclyl" by itself or as part of another term, refers to a monovalent or divalent substituted or unsubstituted aromatic or non-aromatic monocyclic or bicyclic ring system having from 3 to 10 carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Heterocyclyl groups with more than 10 carbons, for instance rings or ring systems with 11, 12, 13, 14, 15, 16, 17, 18, 19 or 20 carbons, are also possible and are encompassed, along with $C_3$-$C_{10}$heterocyclyls, when the term "heterocyclyl" is employed without reference to a specific number of carbons. Similarly, heterocyclyl groups with less than 3 carbons, for instance rings with 1 or 2, are possible and are encompassed when the term "heterocyclyl" is employed without reference to a specific number of carbons. The term "heterocycloalkyl" refers to non-aromatic heterocyclyl rings or ring systems where all carbon atoms are saturated (i.e., bonded to a hydrogen or another substituent as noted below, with no double or triple bonds). In certain embodiments heterocycloalkyl groups typically have 3 to 5 members and 1 to 2 heteroatoms. In certain embodiments heterocycloalkyl can be epoxy.

Unless otherwise noted, the heterocyclyl is attached to its pendant group at any heteroatom or carbon atom that results in a stable structure. Representative examples of a $C_3$—$C_8$ heterocyclyl include, but are not limited to, tetrahyrofuranyl, oxetanyl, pyranyl, pyrrolidinyl, piperidinyl, benzofuranyl, benzothiophene, indolyl, benzopyrazolyl, pyrrolyl, thiophenyl (thiopene), furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocyclyl, or a $C_3$-$C_{10}$ heterocyclyl, can be substituted with up to seven groups including, but not limited to, $C_1$-$C_8$ alkyl, $C_1$-$C_8$ heteroalkyl, —OR, aryl, —C(O)R', —OC(O)R', —C(O)OR, —C(O)NH$_2$, —C(O)NHR', —C(O)N(R')$_2$, —NHC(O)R', —S(=O)$_2$R', —S(O) R', halogen, —NH(R', —N(R)$_2$ and —CN; wherein each R' is independently selected from —H, $C_1$-$C_8$ alkyl, $C_1$-$C_8$ heteroalkyl and aryl. In some embodiments, a substituted heterocyclyl can also include one or more of: —NHC(=NH)NH$_2$, —NHCONH$_2$, —S(=O)$_2$R' and —SR'.

Unless otherwise indicated, "heteroaralkyl" by itself or part of another term, means an alkyl group, as defined above, substituted with an aromatic heterocyclyl group, as defined above.

Unless otherwise indicated, "$C_3$-$C_8$ carbocyclyl" by itself or as part of another term, is a 3-, 4-, 5-, 6-, 7- or 8-membered monovalent or divalent, substituted or unsubstituted, saturated or unsaturated non-aromatic monocyclic or bicyclic carbocyclic ring derived by the removal of one hydrogen atom or two hydrogen atoms from a ring atom of a parent ring system. Similarly, unless otherwise indicated, "$C_3$-$C_{10}$ carbocyclyl" by itself or as part of another term, is a 3-, 4-, 5-,6-, 7-, 8-, 9- or 10-membered monovalent or divalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(111)pentane, and bicyclo(222)octane. A $C_3$-$C_8$ carbocyclyl group, or a $C_3$-$C_{10}$ carbocyclyl group, can be unsubstituted or substituted with up to seven groups including, but not limited to, $C_1$-$C_8$ alkyl, $C_1$-$C_8$ heteroalkyl, —OR', aryl, —C(O)R', —OC(O)R', —C(O)OR, —C(O)NH$_2$, —C(O)NHR', —C(O)N(R)$_2$, —NHC(O)R', —S(=O)$_2$R', —S(=O)R', —OH, -halogen, —NH(R', —N(R)$_2$ and —CN; where each R' is independently selected from —H, $C_1$-$C_8$ alkyl, $C_1$-$C_8$ heteroalkyl and aryl. Carbocyclyl groups with more than 10 carbons, for instance ring systems with 11, 12, 13, 14, 15, 16, 17, 18, 19 or 20 carbons, are also possible and are encompassed, along with $C_3$-$C_{10}$ carbocyclyls, when the term "carbocyclyl" is employed without reference to a specific number of carbons.

The term "cycloalkyl" refers to carbocyclyl rings or ring systems where all carbon atoms are saturated (i.e., bonded to a hydrogen or another substituent as noted below, with no double or triple bonds).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

The terms "racemic mixture" and "racemate" refer to an equimolar mixture of two enantiomeric species, devoid of optical activity.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The terms "loading" or "drug loading" represent or refer to the average number of cytotoxic compounds per antibody in an ADC molecule. Drug loading may range from 1 to 10 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis.

DAR may be limited by the number of attachment sites on the antibody. Two typical means of attachment are via a sulfide linkage with a cysteine thiol residue and an amide linkage with a lysine residue. See Puthenveetil, S., et al., *Bioconjugate Chem.*, 2016, 27:1880-1888. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Most cysteine thiol residues in the antibodies exist as disulfide bridges and must be reduced with a reducing agent such as dithiothreitol (DTT). Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent to form an amide bond with the antibody. The antibody may be subjected to denaturing conditions to reveal reactive nucleophilic groups such as lysine or cysteine.

The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADCs with a distribution of one or more drugs moieties per antibody. The average number of drugs per antibody may be calculated from the mixture by, for example, dual ELISA antibody assay, specific for antibody and specific for the drug. Individual ADCs may be identified in the mixture by mass spectroscopy, and separated by HPLC, e.g., hydrophobic interaction chromatography.

The term "protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

Reference will now be made in detail to certain preferred methods of treatment, compounds and methods of administering these compounds. The invention is not limited to those preferred compounds and methods but rather is defined by the claim(s) issuing here from.

Drug Toxin Compounds

The drug compounds of the present invention are analogs of the naturally occurring cytotoxic compound thailanstatin A or pharmaceutically acceptable salts thereof. Thailanstatin A is one of three structurally similar natural products (A, B and C) identified from a culture broth of *B. thailandensis* MSMB43. These natural products possess potent pre-mRNA inhibitory activity in vitro and antiproliferative activities in human cancer cell lines (Liu, et al., *J. Nat. Prod.*, 2013, 76(4):685-693).

According to one aspect, the present invention relates to a compound or compounds of Formula (I):

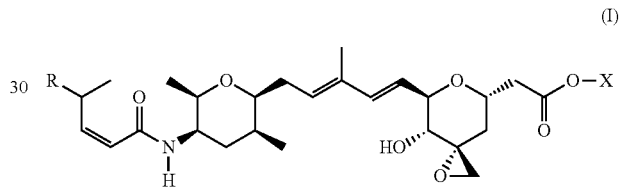

wherein:

R is selected from the selected from the group consisting of:
—(CH$_2$)$_n$—R$^1$; —C$_{5-6}$heteroaryl, optionally substituted with one or more of halogen, —CF$_3$, —C$_{1-6}$alkyl, and —O—C$_{1-6}$alkyl;
—C(R$^2$)=N—R$^3$; —CH(CF$_3$)NH(CH$_2$)$_m$CH$_3$;
—C(R$^a$R$^b$)NH(CH$_2$)$_m$CH$_3$;
—C(halogen)=CH(CH$_2$)$_m$CH$_3$; —SO—NH(CH$_2$)$_m$CH$_3$;
—O(CO)-aryl; —O(CO)-heteroaryl;
—NR$^a$R$^b$; and —NH-heteroaryl;
wherein R$^1$ is —O—CR$^a$R$^b$(CH$_2$)$_m$CH$_3$ or —N—CR$^a$R$^b$(CH$_2$)$_m$CH$_3$;
wherein R$^a$ and R$^b$, together with the atoms to which they are joined, form a C$_{3-10}$ heterocyclyl ring;
R$^2$ is —CN or —NH(CH$_2$)$_m$CH$_3$;
R$^3$ is —(CH$_2$)$_m$CH$_3$ or —O—(CH$_2$)$_m$CH$_3$;
X is —H or —CH$_3$;
each n is independently 1, 2, or 3; and
each m is independently 0, 1, 2, or 3;
or a pharmaceutically acceptable salt thereof.

In certain exemplary embodiments, R is selected from the group consisting of:

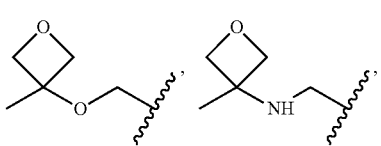

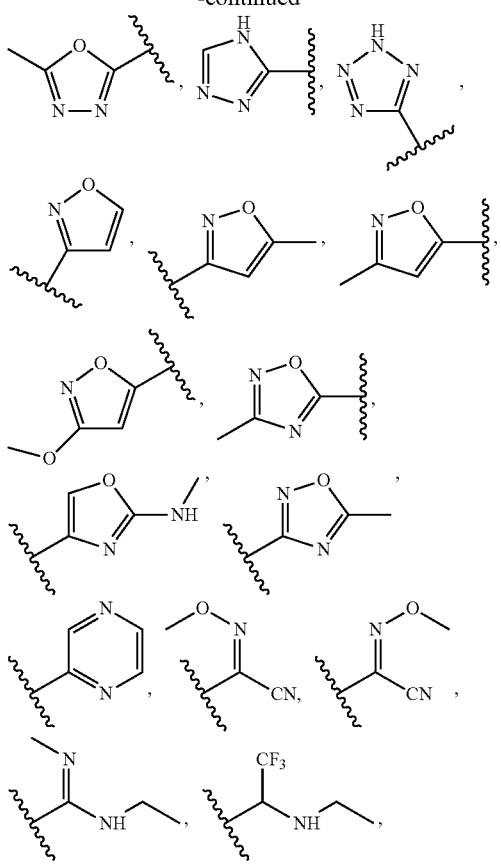
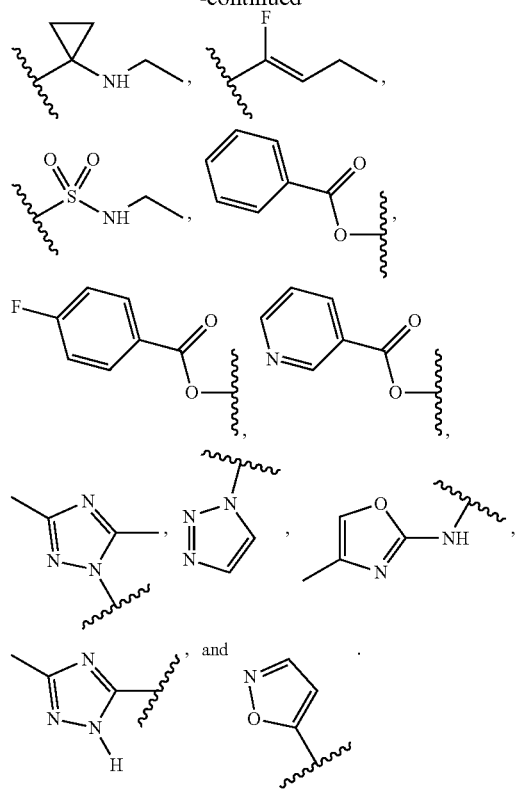
In another embodiment, a compound of the invention is selected from the group consisting of:
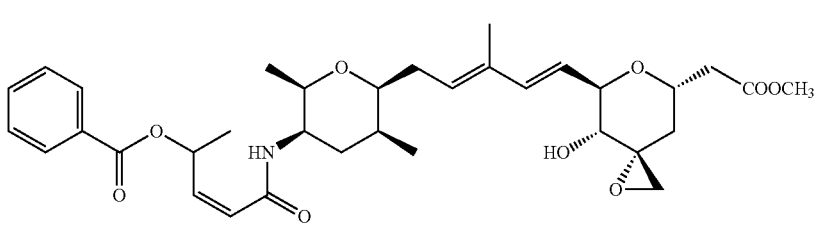
1
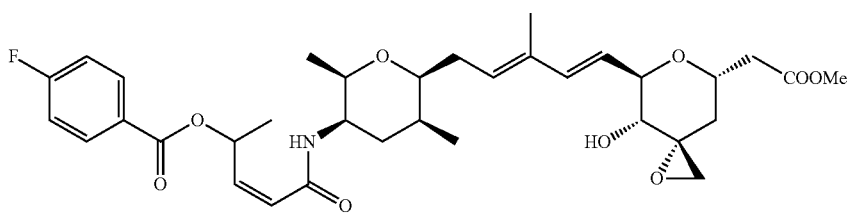
2
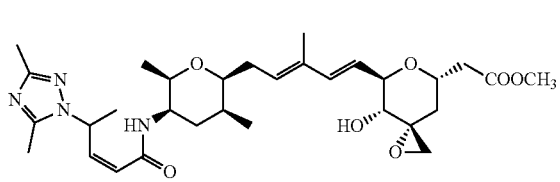
3
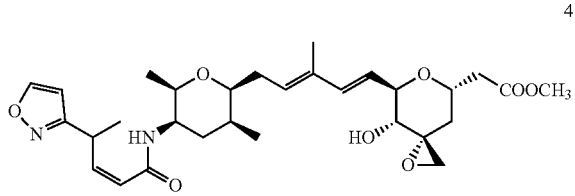
4

-continued

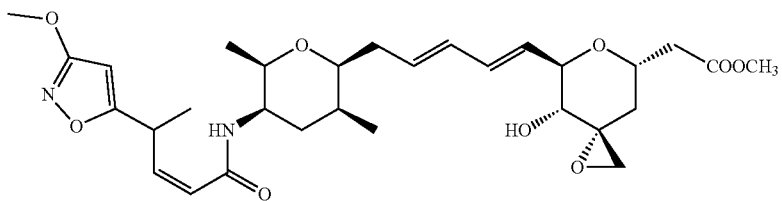

5

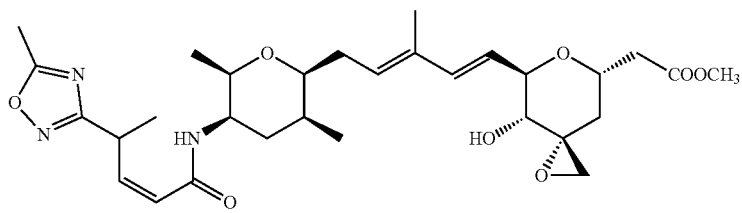

6

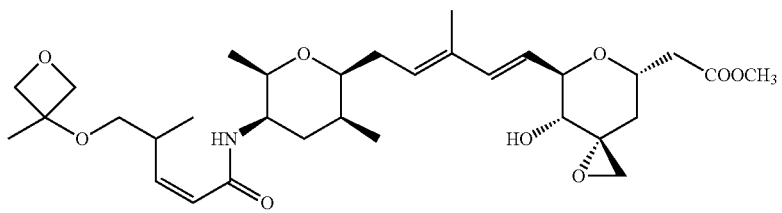

7

Methods for the synthesis of the compounds of the invention are given in the Examples section below.

Linker Unit (L) and Linker Moiety (L')

According to another aspect, the present invention relates to a compound or compounds of Formula (II):

(II)

or a pharmaceutically acceptable salt thereof, wherein:
L is a linker, Formula (II):
R is selected from the selected from the group consisting of:
—(CH$_2$)$_n$—R$^1$; —C$_{5-6}$heteroaryl, optionally substituted with one or more of halogen, —CF$_3$, —C$_{1-6}$alkyl, and —O—C$_{1-6}$alkyl;

—C(R$^2$)=N—R$^3$; —CH(CF$_3$)NH(CH$_2$)$_m$CH$_3$;
—C(R$^a$R$^b$)NH(CH$_2$)$_m$CH$_3$;

—C(halogen)=CH(CH$_2$)$_m$CH$_3$; —SON H(CH$_2$)$_m$CH$_3$;
—O(CO)-aryl; —O(CO)-heteroaryl;

—NR$^a$R$^b$; and —NH-heteroaryl;

wherein R$^1$ is —O—CR$^a$R$^b$(CH$_2$)$_m$CH$_3$ or —N—CR$^a$R$^b$(CH$_2$)$_m$CH$_3$;

wherein R$^a$ and R$^b$, together with the atoms to which they are joined, form a C$_{3-10}$ heterocyclyl ring;

R$^2$ is —CN or —NH(CH$_2$)$_m$CH$_3$;

R$^3$ is —(CH$_2$)$_m$CH$_3$ or —O—(CH$_2$)$_m$CH$_3$;

each n is independently 1, 2, or 3; and
each m is independently 0, 1, 2, or 3;
or a pharmaceutically acceptable salt thereof.

In certain exemplary embodiments, L is selected from the group consisting of Formula (A$^1$), Formula (A$^2$), Formula (A$^3$), Formula (A$^4$), and Formula (A$^5$):

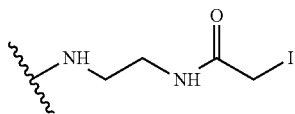
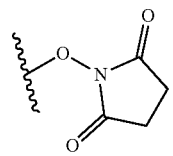
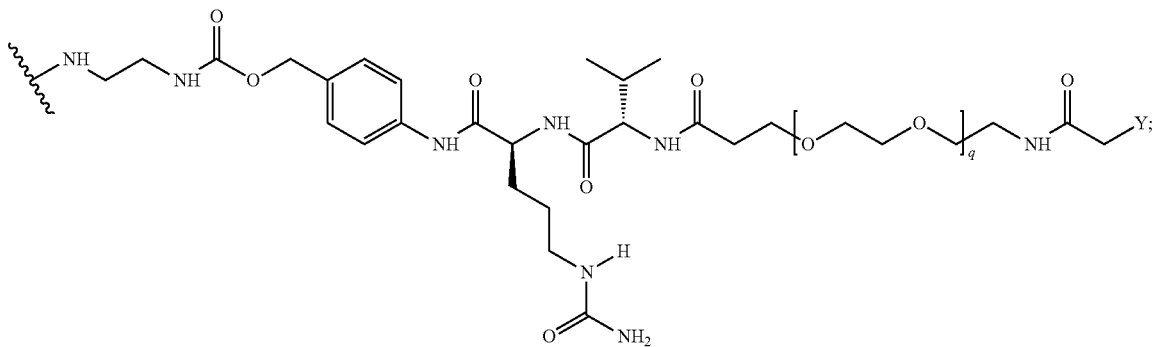
wherein q is 3, 4, 5, 6, 7, 8, 9, or 10; and
Y is Br, I, or
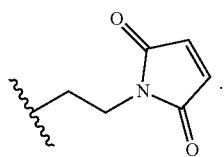 [SMILES: *CCN1C(=O)C=CC1=O]
In other exemplary embodiments, R is selected from the group consisting of:
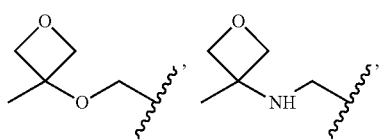
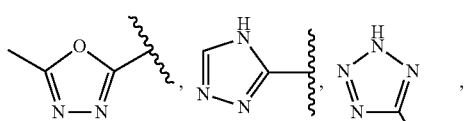
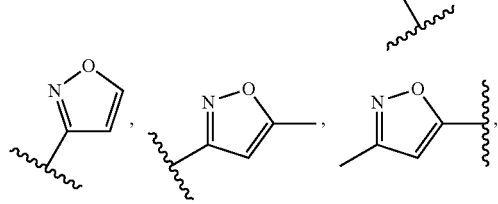
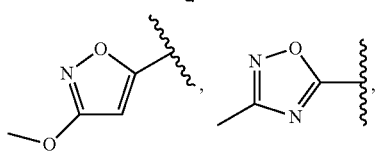
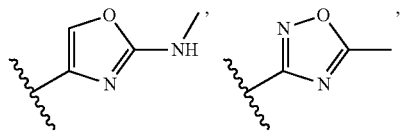
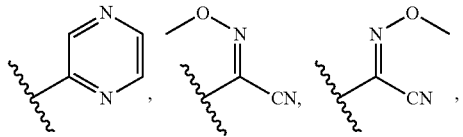
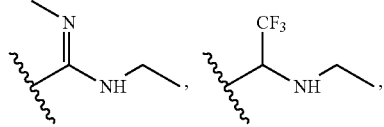
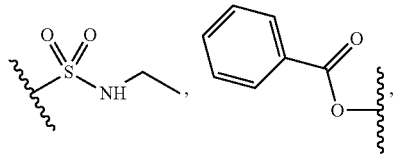
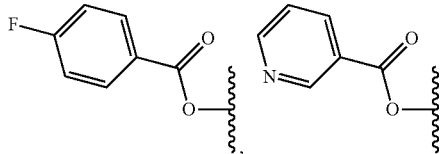
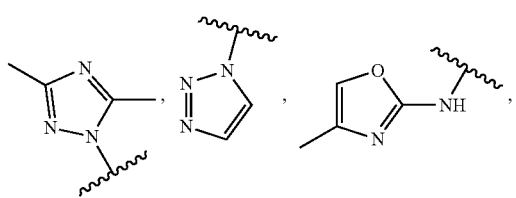

-continued

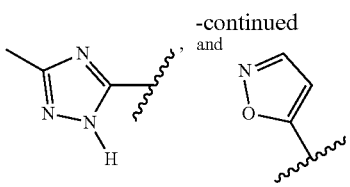

A linker is a bifunctional or multifunctional compound which can be used to link a drug and an antibody to form an antibody-drug conjugate (ADC). Such conjugates are useful, for example, in the formation of immunoconjugates directed against tumor associated antigens. Such conjugates allow the selective delivery of cytotoxic drugs to tumor cells. In an ADC, the linker serves to attach the toxin to the antibody.

In the context of the invention, a "Linker" (L) is a bifunctional or multifunctional moiety that can be used to link one or more toxin drug moieties to an antibody (Ab) to form the antibody-drug conjugate (ADC) of Formula III. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate of Formula II to make an ADC.

The Linker L is covalently bound via one reactive site of a bifunctional compound, leaving the other functional site available for subsequent attachment to an antibody. The Linker L is a moiety having 1-200 non-hydrogen atoms selected from C, N, O, S, or halogen, and optionally incorporates ether, oxo, carboxyl, carboxamide, carboxamidyl, urethanyl, branched, cyclic, unsaturated, amino acid, heterocyclic, aromatic or heteroaromatic moieties. Linker L may be unbranched or branched, flexible or rigid, short or long and may incorporate any combination of moieties as deemed useful. In some embodiments, at least a portion of the linker L may have a polyalkylene oxide polymeric region, which may enhance solubility of the compound of Formula (III). In some embodiments, the Linker L may have a repeating unit of ethylene glycol, and may have a number of repeating ethylene glycol units of about 1 to about 25, or any number there between. In some embodiments, L may include about 1 to about 4, about 3 to about 20, about 4 to about 15, about 5 to about 12 or about 6 to about 10 ethylene glycol units.

In some embodiments, at least a portion of Linker L may include one or more amino acid moieties which may provide enhanced solubility for the compound of Formula (III) or may provide amino acid sequences to enhance target binding, enhance compatibility with a target binding agent, or enhance target binding recognition. In other embodiments, the Linker L may include one or more amino acid moieties that provide a suitable substrate motif for a protease. Such embodiments include amino acids selected from glycine, alanine, phenylalanine, lysine, arginine, valine, and citrulline. When a set of amino acid moieties are incorporated into the linker L that provide a substrate motif specific for a selected protease, the cytotoxic drug compound of Formula (III) may be released from a target bound conjugate to provide localized cytotoxic effects. Such substrate motifs are known in the art and may be incorporated into the Linker L as desired to provide selective release from the target bound conjugate. This selectivity can be based on known presence of a desired protease within the localized delivery region of the drug-antibody conjugate. Other polymeric types of moieties may be incorporated in the Linker L, such as polyacids, polysaccharides, or polyamines. Other moieties such as substituted aromatic or heteroaromatic moieties may be used to enhance rigidity or provide synthetically accessible sites on substituents therein for linking to reactive moieties or to the compound of Formula (III).

The other second functional site of Linker L is available for subsequent attachment to an antibody, thus covalently bonding the toxin of the invention to an antibody via a linker. This second reactive site is, for example, an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit. In some embodiments, the electrophilic groups include:

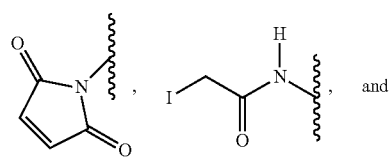

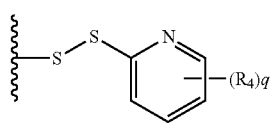

where the wavy lines indicate the attachments to L, and $R^4$ is $NO_2$, Cl, F, CN, or Br, and q is 0, 1, or 2.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments.

In one aspect, a linker has a functionality that is capable of reacting with a free cysteine present on an antibody to form a covalent bond. Nonlimiting examples of such reactive functionalities include maleimide, haloacetamides, α-haloacetyl, pyridyl disulfide, activated esters such as succinimide esters, N-hydroxysuccinimide, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al., *Bioconjugate Chemistry*, 2004, 15(4):765-773, and the Examples herein.

In some embodiments, a linker has a functionality that is capable of reacting with an electrophilic group present on an antibody. Examples of such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting examples of reactive functionalities include, but are not limited to, hydrazide, oxime, amino, hydrazine, thiosemicarbazone, hydrazine carboxylate, and arylhydrazide.

A linker may comprise one or more linker components, including but not limited to, a stretcher unit, a peptidomimetic unit, a peptide unit, and a spacer unit. See J. Lu., et al. (*Int. J. Mol. Sci.*, 2016, 17:561). Exemplary linker components and linker reagents include, but are not limited to, p-amino benzoic acid-valine-citrulline ("PABA-val-cit"), 6-maleimidocaproyl ("MC"), maleimidopropanoyl ("MP"), valine-citrulline ("val-cit" or "vc"), valine-alanine ("val-ala" or "va"), alanine-phenylalanine ("ala-phe"), phenylalanine-lysine (phe-lys), glycine-phenylalanine-leucine-glycine ("GFLG"), p-aminobenzyloxycarbonyl ("PAB"), N-succinimidyl 4-(2-pyridylthio) pentanoate ("SPP"), 4-(N-maleimidomethyl) cyclohexane-1 carboxylate ("MCC"), 4-(N-maleimidomethyl)cyclohexanecarboxylic acid N-hydroxysuccinimide ester ("SMCC"), N-succinimidyl 4-(2-pyridyldithio)butanoate ("SPDB"), and sulfo-N-succinimidyl 4-(2-pyridyldithio)butyrate ("sulfo-SPDB"). Various linker components are known in the art, which are described herein. Exemplary linker components include, but are not limited to, "VC-2×PEG", "VA-2×PEG", and "VC-8×PEG", and "VA-8×PEG", where a valine-citrulline unit is attached to two or more ethyleneoxy units (PEG), for example, two to 10 PEG units.

A linker may be a "cleavable linker," facilitating release of a drug or toxin. Nonlimiting examples of cleavable linkers include acid-labile linkers (e.g., comprising hydrazone), protease-sensitive (e.g., peptidase-sensitive) linkers, photolabile linkers, or disulfide-containing linkers (Chari, et al., *Cancer Research*, 1992, 52:127-131; U.S. Pat. No. 5,208,020).

Further examples of embodiments of linkers are described in U.S. Pat. No. 7,498,298, which is expressly incorporated herein by reference.

In the context of the present invention, the L' moiety is the central portion of a bifunctional linker which remains in an antibody-drug conjugate after the drug has been covalently bound to the antibody via this central portion. The L' moiety is as described above for the Linker L except that the second functional site, either an electrophilic or a nucleophilic group, has reacted as described above with an antibody to form a covalent bond. A non-limiting example of an L' moiety, derived from an N-hydroxysuccinimide acetate ester (NHS ester) linker, and capable of binding to a lysine residue on an antibody as described above, is shown in Formula (B¹):

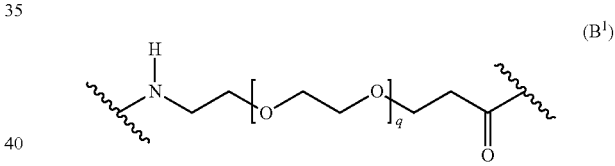

wherein q is 3, 4, 5, 6, 7, 8, 9, or 10. A further non-limiting example of an L' moiety, including a maleimide unit capable of binding to a cysteine residue on an antibody, is shown in Formula (B²):

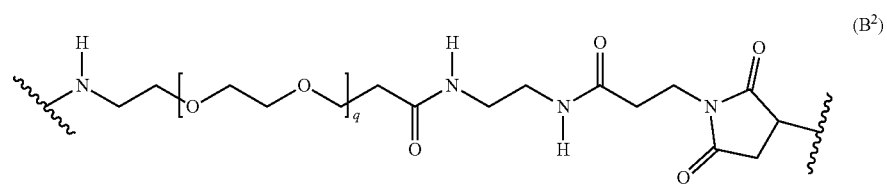

wherein q is 3, 4, 5, 6, 7, 8, 9, or 10. A further non-limiting example of an L' moiety, including an amide unit capable of binding to a cysteine residue on an antibody, is shown in Formula (B³):

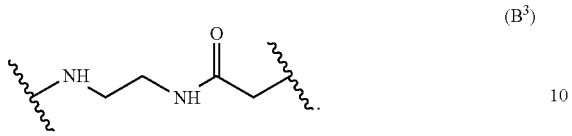

(B³)

Another non-limiting example of an L' moiety, including an amide unit capable of binding to a cysteine residue on an antibody, is shown in Formula (B⁴):

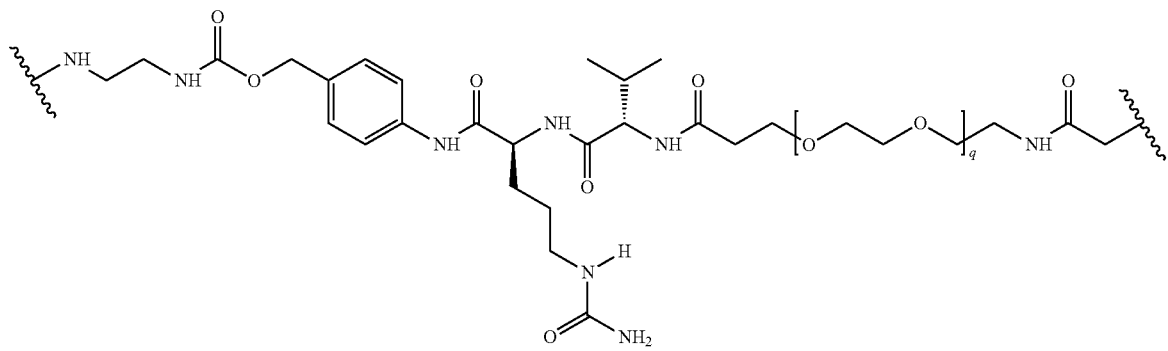

(B⁴)

wherein q is 3, 4, 5, 6, 7, 8, 9, or 10.

In cases where L comprises Formula (A⁴),

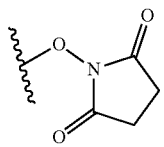

(A⁴)

an available —NH₂ group on the antibody, for example, from a lysine residue, displaces Formula (A⁴), resulting in a direct link between the antibody and the compound of Formula (I).

Antibody Unit (Ab or AB)

As noted above, the term "antibody" (or "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody-drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody a conjugates of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

In another aspect, the present invention relates to an antibody-drug conjugate compound of Formulae III wherein the antibody AB is selected from: gemtuzumab, trastuzumab (Herceptin®), pertuzumab (Perjeta®), iratumumab, inotuzumab, pinatuzumab, epratuzumab, polatuzumab, coltuximab, lovotuzumab, sacituzumab, anetumab, aprutumab, aratumumab, atezolizumab, avelumab, azintuxizumab, bevacizumab (Avastin®), bivatuzumab, brentuximab, camidanlumab, cantuzumab, cetuximab (Erbitux®)), cofetuzumab, denintuzumab, durvalumab, elotuzumab, enfortumab, glembatumumab, ibritumomab, iladatuzumab, indatuximab, industuzumab, labetuzumab, ladiratuzumab, laprituximab, lifastuzumab, loncastuximab, lorvotuzumab, lupartumab, milatuzumab, mirvetuximab, naratuximab, natalizumab, necitumumab, obinutuzumab, ocrelizumab, ofatumumab, olaratumab, panitumumab, pertuzumab, rituximab (Rituxan®), rovalpituzumab, sirtratumab, sofituzumab, telisotuzumab, tositumomab, trastuzumab, and vadastuximab. In certain preferred embodiments, the antibody AB is selected from the group consisting of: trastuzumab, pertuzumab, gemtuzumab, and vadastuximab.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification.

In one embodiment, an antibody unit has a sulfhydryl group and the antibody unit bonds via the sulfhydryl group's sulfur atom.

In another embodiment, the antibody has lysine residues that can react with activated esters (such esters include, but are not limited to, N-hydroxysuccinimde, pentafluorophenyl, and p-nitrophenyl esters) and thus form an amide bond consisting of the nitrogen atom of the antibody unit and a carbonyl.

In yet another aspect, the antibody unit has one or more lysine residues that can be chemically modified to introduce one or more sulfhydryl groups. The reagents that can be used to modify lysines include, but are not limited to, N-hydroxysuccinimide acetate ester (NHS ester), N-succinimidyl S-acetylthioacetate (SATA), and 2-Iminothiolane hydrochloride (Traut's Reagent).

In another embodiment, the antibody unit can have one or more carbohydrate groups that can be chemically modified to have one or more sulfhydryl groups.

In yet another embodiment, the antibody unit can have one or more carbohydrate groups that can be oxidized to provide an aldehyde group. The corresponding aldehyde can form a bond with a reactive site such as, for example, hydrazine and hydroxylamine. Other protocols for the modification of proteins for the attachment or association of drugs are described in Coligan et al., *Current Protocols in Protein Science*, Vol. 2, John Wiley & Sons (2002).

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art.

The antibody can also be a bispecific antibody. Methods for making bispecific antibodies are known in the art.

The antibody can be a functionally active fragment, derivative or analog of an antibody that immunospecifically binds to target cells (e.g., tumor-associated antigens, cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay).

Other useful antibodies include fragments of antibodies such as, but not limited to, F(ab)$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. Humanized antibodies are antibody molecules from non-human species having one or more complementarity determining regions (CDRs) from the non-human species and a framework region from a human immunoglobulin molecule. Such chimeric and humanized monoclonal antibodies can be produced by recombinant DNA techniques known in the art.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies using methods known to one skilled in the art. Other human antibodies can be obtained commercially from numerous companies.

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. Human antibodies can also be produced using various techniques known in the art, including phage display libraries.

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor.

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen (tumor-associated antigens) can be obtained, e.g., from the GenBank database or a database like it, the literature publications, or by routine cloning and sequencing.

Examples of tumor-associated antigens (TAA) include, but are not limited to, TAA (1)-(100) listed herein. For convenience, in most cases, information relating to these antigens, all of which are known in the art, is listed herein and includes, in most cases, names, alternative names, GenBank accession numbers and primary reference(s), following nucleic acid and protein sequence identification conventions of the National Center for Biotechnology Information (NCBI). Nucleic acid and protein sequences corresponding to TAA (1)-(100) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Specific non-limiting examples of TAA include:

(1) BMPR1B (bone morphogenetic protein receptor-type IB, GenBank accession no. NM_001203); ten Dijke, P., et al., *Science*, 1994, 264 (5155):101-104; Oncogene, 1997, 14(11):1377-1382); WO 2004/063362 (Claim 2); WO 2003/042661 (Claim 12); US 2003/134790 (Page 38-39); WO 2002/102235 (Claim 13; Page 296); WO 2003/055443 (Page 91-92); WO 2002/99122 (Example 2; Page 528-530); WO 2003/029421 (Claim 6); WO 2003/024392 (Claim 2; FIG. 112); WO 2002/98358 (Claim 1; Page 183); WO 2002/54940 (Page 100-101); WO 2002/59377 (Page 349-350); WO 2002/30268 (Claim 27; Page 376); WO 2001/48204 (Example; FIG. 4) NP_001194 bone morphogenetic protein receptor, type IB/pid=NP_001194.1—Cross-references: MIM:603248; NP_001194.1; AY065994.

(2) E16 (LAT1, SLC7A5, GenBank accession no. NM_003486); *Biochem. Biophys. Res. Commun.*, 1999, 255 (2), 283-288; Nature, 1998, 395(6699):288-291; Gaugitsch, H. W., et al., *J. Biol. Chem.*, 1992, 267(16):11267-11273); WO 2004/048938 (Example 2); WO 2004/032842 (Example IV); WO 2003/042661 (Claim 12); WO 2003/016475 (Claim 1); WO 2002/78524 (Example 2); WO 2002/99074 (Claim 19; Page 127-129); WO 2002/86443 (Claim 27; Pages 222, 393); WO 2003/003906 (Claim 10; Page 293); WO 2002/64798 (Claim 33; Page 93-95); WO 2000/14228 (Claim 5; Page 133-136); US 2003/224454 (FIG. 3); WO 2003/025138 (Claim 12; Page 150); NP_003477 solute carrier family 7 (cationic amino acid transporter, y+system), member 5/pid=NP_003477.3—Homo sapiens Cross-references: MIM:600182; NP_003477.3; NM_015923; NM_003486_1.

(3) STEAP1 (six transmembrane epithelial antigen of prostate, GenBank accession no. NM_012449); *Cancer Res.*, 2001, 61(15), 5857-5860; Hubert, R. S., et al., *Proc. Natl. Acad. Sci. U.S.A.*, 96 (25):14523-14528); WO 2004/065577 (Claim 6); WO 2004/027049 (FIG. 1L); EP 1394274 (Example 11); WO 2004/016225 (Claim 2); WO 2003/042661 (Claim 12); US 2003/157089 (Example 5); US 2003/185830 (Example 5); US 2003/064397 (FIG. 2); WO 2002/89747 (Example 5; Page 618-619); WO 2003/022995 (Example 9; FIG. 13A, Example 53; Page 173, Example 2; FIG. 2A); NP_036581 six transmembrane epithelial antigen of the prostate Cross-references: MIM:604415; NP_036581.1; NM_012449_1.

(4) 0772P (CA125, MUC16, GenBank accession no. AF361486); *J. Biol. Chem.*, 2001, 276(29):27371-27375; WO 2004/045553 (Claim 14); WO 2002/92836 (Claim 6; FIG. 12); WO 2002/83866 (Claim 15; Page 116-121); US 2003/124140 (Example 16). Cross-references: GI:34501467; AAK74120.3; AF361486_1.

(5) MPF (MPF, MSLN, SMR, megakaryocyte potentiating factor, mesothelin, GenBank accession no. NM_005823); Yamaguchi, N., et al., *Biol. Chem.*, 1994, 269(2), 805-808; Proc. Natl. Acad. Sci. U.S.A., 1999, 96(20):11531-11536; Proc. Natl. Acad. Sci. U.S.A., 1996, 93(1):136-140; J. Biol. Chem., 1995, 270(37):21984-21990; WO 2003/101283 (Claim 14); (WO 2002/102235 (Claim 13; Page 287-288); WO 2002/101075 (Claim 4; Page 308-309); WO 2002/71928 (Page 320-321); WO 9410312 (Page 52-57); Cross-references: MIM:601051; NP 005814.2; NM_0058231.

(6) Napi3b (NAPI-3B, NPTIIb, SLC34A2, solute carrier family 34 (sodium phosphate), member 2, type II sodium-dependent phosphate transporter 3b, GenBank accession no. NM_006424); *J. Biol. Chem.*, 2002, 277(22):19665-19672; Genomics, 1999, 62(2):281-284; Feild, J. A., et al., *Biochem. Biophys. Res. Commun.*, 1999, 258(3):578-582); WO 2004/022778 (Claim 2); EP 1394274 (Example 11); WO 2002/102235 (Claim 13; Page 326); EP 875569 (Claim 1; Page 17-19); WO 2001/57188 (Claim 20; Page 329); WO 2004/032842 (Example IV); WO200175177 (Claim 24; Page 139-140); Cross-references: MIM:604217; NP_006415.1; NM_006424_1.

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, GenBank accession no. AB040878); Nagase T., et al., *DNA Res.*, 2000, 7(2):143-150); WO 2004/000997 (Claim 1); WO 2003/003984 (Claim 1); WO 2002/06339 (Claim 1; Page 50); WO 2001/88133 (Claim 1; Page 41-43, 48-58); WO 2003/054152 (Claim 20); WO 20031/01400 (Claim 11); Accession: Q9P283; EMBL; AB040878; BAA95969.1. Genew; HGNC:10737.

(8) PSCA hig (2700050C12Rik, C530008O16Rik, RIKEN cDNA 2700050C12, RIKEN cDNA 2700050C12 gene, GenBank accession no. AY358628); Ross et al., *Cancer Res.*, 2002, 62:2546-2553; US 2003/129192 (Claim 2);

US 2004/044180 (Claim 12); US 2004/044179 (Claim 11); US 2003/096961 (Claim 11); US 2003/232056 (Example 5); WO 2003/105758 (Claim 12); US 2003/206918 (Example 5); EP 1347046 (Claim 1); WO 2003/025148 (Claim 20); Cross-references: GI:37182378; AAQ88991.1; AY358628_1.

(9) ETBR (Endothelin type B receptor, GenBank accession no. AY275463); Nakamuta M., et al., *Biochem. Biophys. Res. Commun.*, 1991, 177:34-39; Ogawa Y., et al., *Biochem. Biophys. Res. Commun.*, 1991, 178, 248-255; Arai, H., et al., *Jpn. Circ. J.*, 1992, 56:1303-1307; Arai, H., et al., *J. Biol. Chem.*, 1993, 268:3463-3470; Sakamoto A., Yanagisawa M., et al., *Biochem. Biophys. Res. Commun.*, 1991, 178:656-663; Elshourbagy N. A., et al., *J. Biol. Chem.*, 1993, 268:3873-3879; Haendler B., et al., *J. Cardiovasc. Pharmacol.*, 1992, 20:s1-S4; Tsutsumi M., et al., *Gene*, 1999, 228:43-49; Strausberg, R. L., et al., *Proc. Natl. Acad. Sci. U.S.A.*, 2002, 99:16899-16903; Bourgeois C., et al., *J. Clin. Endocrinol. Metab.*, 1997, 82, 3116-3123; Okamoto Y., et al., *Biol. Chem.*, 1997, 272:21589-21596; Verheij, J. B., *Am. J. Med. Genet.*, 2002, 108:223-225; Hofstra, R. M. W., et al., *Eur. J. Hum. Genet.*, 1997, 5:180-185; Puffenberger, E. G., et al., *Cell*, 1994, 79:1257-1266; Attie T., et al., *Hum. Mol. Genet.*, 1995, 4:2407-2409; Auricchio A., et al., *Hum. Mol. Genet.*, 1996, 5:351-354; Amiel J., et al. Hum. Mol. Genet. 5, 355-357, 1996; Hofstra R. M. W., et al. Nat. Genet., 1996, 12:445-447; Svensson, P. J., et al., *Hum. Genet.*, 1998, 103:145-148; Fuchs, S., et al., *Mol. Med.*, 2001, 7:115-124; Pingault V., et al., Hum. Genet., 2002, 111:198-206; WO 2004/045516 (Claim 1); WO 2004/048938 (Example 2); WO 2004/040000 (Claim 151); WO 2003/087768 (Claim 1); WO 2003/016475 (Claim 1); WO 2003/016475 (Claim 1); WO 2002/61087 (FIG. 1); WO 2003/016494 (FIG. 6); WO 2003/025138 (Claim 12; Page 144); WO 2001/98351 (Claim 1; Page 124-125); EP 522868 (Claim 8; FIG. 2); WO 2001/77172 (Claim 1; Page 297-299); US 2003/109676; U.S. Pat. No. 6,518,404 (FIG. 3); U.S. Pat. No. 5,773,223 (Claim 1a; Col 31-34); WO 2004/001004.

(10) MSG783 (RNF124, hypothetical protein FLJ20315, GenBank accession no. NM_017763); WO 2003/104275 (Claim 1); WO 2004/046342 (Example 2); WO 2003/042661 (Claim 12); WO 2003/083074 (Claim 14; Page 61); WO 2003/018621 (Claim 1); WO 2003/024392 (Claim 2; FIG. 93); WO 2001/66689 (Example 6); Cross-references: LocusID:54894; NP_060233.2; NM_017763_1.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, GenBank accession no. AF455138) Lab. Invest. 82 (11):1573-1582 (2002)); WO 2003/087306; US 2003/064397 (Claim 1; FIG. 1); WO 2002/72596 (Claim 13; Page 54-55); WO 2001/72962 (Claim 1; FIG. 4B); WO 2003/104270 (Claim 11); WO 2003/104270 (Claim 16); US 2004/005598 (Claim 22); WO 2003/042661 (Claim 12); US 2003/060612 (Claim 12; FIG. 10); WO 2002/26822 (Claim 23; FIG. 2); WO 2002/16429 (Claim 12; FIG. 10); Cross-references: GI:22655488; AAN04080.1; AF455138_1.

(12) TrpM4 (BR22450, FLJ20041, TRPM4, TRPM4B, transient receptor potential cation channel, subfamily M, member 4, GenBank accession no. NM_017636) Xu, X. Z., et al., *Proc. Natl. Acad. Sci. U.S.A.*, 2001, 98(19):10692-10697; Cell, 2002, 109(3):397-407; J. Biol. Chem., 2003, 278(33):30813-30820; US 2003/143557 (Claim 4); WO 2000/40614 (Claim 14; Page 100-103); WO 2002/10382 (Claim 1; FIG. 9A); WO 2003/042661 (Claim 12); WO 2002/30268 (Claim 27; Page 391); US 2003/219806 (Claim 4); WO 2001/62794 (Claim 14; FIG. 1A-D); Cross-references: MIM:606936; NP_060106.2; NM_017636_1.

(13) CRIPTO (CR, CR1, CRGF, CRIPTO, TDGF1, teratocarcinoma-derived growth factor, GenBank accession no. NP_003203 or NM_003212); Ciccodicola, A., et al., *EMBO J.*, 1989, 8(7):1987-1991; Am. J. Hum. Genet., 1991, 49(3):555-565; US 2003/224411 (Claim 1); WO 2003/083041 (Example 1); WO 2003/034984 (Claim 12); WO 2002/88170 (Claim 2; Page 52-53); WO 2003/024392 (Claim 2; FIG. 58); WO 2002/16413 (Claim 1; Page 94-95, 105); WO 2002/22808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1.

(14) CD21 (CR2 (Complement receptor 2) or C3DR (C3d/Epstein Barr virus receptor) or Hs.73792 GenBank accession no. M26004); Fujisaku, et al., *J. Biol. Chem.*, 1989, 264(4):2118-2125); Weis J. J., et al., *J. Exp. Med.*, 1988, 167:1047-1066; Moore M., et al., *Proc. Natl. Acad. Sci. U.S.A.*, 1987, 84:9194-9198; Barel M., et al., *Mol. Immunol.*, 1998, 35:1025-1031; Weis J. J., et al., *Proc. Natl. Acad. Sci. U.S.A.*, 1986, 83:5639-5643; Sinha S. K., et al., *J. Immunol.*, 1993, 150:5311-5320; WO 2004/045520 (Example 4); US 2004/005538 (Example 1); WO 2003/062401 (Claim 9); WO 2004/045520 (Example 4); WO 9102536 (FIGS. 9.1-9.9); WO 2004/020595 (Claim 1); Accession: P20023; Q13866; Q14212; EMBL; M26004; AAA35786.1.

(15) CD79b (CD79B, CD79β, IGb (immunoglobulin-associated beta), B29, GenBank accession no. NM_000626 or 11038674); *Proc. Natl. Acad. Sci. U.S.A.*, 2003, 100(7): 4126-4131; Blood, 2002, 100(9):3068-3076; Muller, et al., *Eur. J. Immunol.*, 1992, 22(6):1621-1625; WO 2004/016225 (claim 2, FIG. 140); WO 2003/087768, US 2004/101874 (claim 1, page 102); WO 2003/062401 (claim 9); WO 2002/78524 (Example 2); US 2002/150573 (claim 5, page 15); U.S. Pat. No. 5,644,033; WO 2003/048202 (claim 1, pages 306 and 309); WO 99/558658, U.S. Pat. No. 6,534,482 (claim 13, FIG. 17A/B); WO 2000/55351 (claim 11, pages 1145-1146); Cross-references: MIM:147245; NP_000617.1; NM_000626_1.

(16) FcRH2 (IFGP4, IRTA4, SPAP1A (SH2 domain containing phosphatase anchor protein 1a), SPAP1B, SPAP1C, GenBank accession no. NM_030764, AY358130); *Genome Res.*, 2003, 13(10):2265-2270; Immunogenetics, 2002, 54(2):87-95; Blood, 2002, 99(8):2662-2669; Proc. Nat. Acad. Sci. U.S.A., 2001, 98(17):9772-9777; Xu, M. J., et al., *Biochem. Biophys. Res. Commun.*, 2001, 280(3):768-775; WO 2004/016225 (Claim 2); WO 2003/077836; WO 2001/38490 (Claim 5; FIG. 18D-1-18D-2); WO 2003/097803 (Claim 12); WO 2003/089624 (Claim 25); Cross-references: MIM:606509; NP_110391.2; NM_030764_1.

(17) HER2 (ErbB2, GenBank accession no. M11730); Coussens, L., et al., *Science*, 1985, 230(4730):1132-1139); Yamamoto, T., et al., *Nature*, 1986, 319:230-234; Semba, K., et al., *Proc. Natl. Acad. Sci. U.S.A.*, 1985, 82:6497-6501; Swiercz, J. M., et al., *J. Cell Biol.*, 2004, 165:869-880; Kuhns, J. J., et al., *J. Biol. Chem.*, 1999, 274:36422-36427; Cho H.-S., et al., *Nature*, 1993, 421:756-760; Ehsani, A., et al., *Genomics*, 1993, 15:426-429; WO 2004/048938 (Example 2); WO 2004/027049 (FIG. 11); WO 2004/009622; WO 2003/081210; WO 2003/089904 (Claim 9); WO 2003/016475 (Claim 1); US 2003/118592; WO 2003/008537 (Claim 1); WO 2003/055439 (Claim 29; FIG. 1A-B); WO 2003/025228 (Claim 37; FIG. 5C); WO 2002/22636 (Example 13; Page 95-107); WO 2002/12341 (Claim 68; FIG. 7); WO 2002/13847 (Page 71-74); WO 2002/14503 (Page 114-117); WO 2001/53463 (Claim 2; Page 41-46); WO 2001/41787 (Page 15); WO 2000/44899 (Claim 52; FIG. 7); WO 2000/20579 (Claim 3; FIG. 2); U.S. Pat. No. 5,869,445 (Claim 3; Col 31-38); WO 9630514 (Claim 2; Page 56-61); EP 1439393 (Claim 7); WO 2004/043361 (Claim 7); WO 2004/022709; WO 2001/00244 (Example 3; FIG. 4); Accession: P04626; EMBL; M11767; AAA35808.1. EMBL; M11761; AAA35808.1.

(18) NCA (CEACAM6, GenBank accession no. M18728); Barnett T., et al., *Genomics*, 1988, 3:59-66; Tawaragi, Y., et al., *Biochem. Biophys. Res. Commun.*, 1988, 150:89-96; Strausberg, R. L., et al. *Proc. Natl. Acad. Sci. U.S.A.*, 2002, 99:16899-16903; WO 2004/063709; EP 1439393 (Claim 7); WO 2004/044178 (Example 4); WO 2004/031238; WO 2003/042661 (Claim 12); WO 2002/78524 (Example 2); WO 2002/86443 (Claim 27; Page 427); WO 2002/60317 (Claim 2); Accession: P40199; Q14920; EMBL; M29541; AAA59915.1. EMBL; M18728.

(19) MDP (DPEP1, GenBank accession no. BC017023); *Proc. Natl. Acad. Sci. U.S.A.*, 2002, 99(26):16899-16903; WO 2003/016475 (Claim 1); WO 2002/64798 (Claim 33; Page 85-87); JP 05003790 (FIG. 6-8); WO 9946284 (FIG. 9); Cross-references: MIM:179780; AAH17023.1; BC017023_1.

(20) IL20Rα (IL20Ra. ZCYTOR7, GenBank accession no. AF184971); Clark H. F., et al., *Genome Res.*, 2003, 13:2265-2270; Mungall A. J., et al., *Nature*, 2003, 425:805-811; Blumberg H., et al., *Cell*, 2001, 104:9-19; Dumoutier L., et al., *J. Immunol.*, 2001, 167:3545-3549; Parrish-Novak J., et al., *J. Biol. Chem.*, 2002, 277:47517-47523; Pletnev, S., et al., *Biochemistry*, 2003, 42:12617-12624; Sheikh F., et al., *J. Immunol.*, 2004, 172:2006-2010; EP 1394274 (Example 11); US 2004/005320 (Example 5); WO 2003/029262 (Page 74-75); WO 2003/002717 (Claim 2; Page 63); WO 2002/22153 (Page 45-47); US 2002/042366 (Page 20-21); WO 2001/46261 (Page 57-59); WO 2001/46232 (Page 63-65); WO 9837193 (Claim 1; Page 55-59); Accession: Q9UHF4; Q6UWA9; Q96SH8; EMBL; AF184971; AAF01320.1.

(21) Brevican (BCAN, BEHAB, GenBank accession no. AF229053); Gary S. C., et al., *Gene*, 2000, 256:39-147; Clark H. F., et al., *Genome Res.*, 2003, 13:2265-2270; Strausberg, R. L., et al. *Proc. Natl. Acad. Sci. U.S.A.*, 2002, 99:16899-16903; US 2003/186372 (Claim 11); US 2003/186373 (Claim 11); US 2003/119131 (Claim 1; FIG. 52); US 2003/119122 (Claim 1; FIG. 52); US 2003/119126 (Claim 1); US 2003/119121 (Claim 1; FIG. 52); US 2003/119129 (Claim 1); US 2003/119130 (Claim 1); US 2003/119128 (Claim 1; FIG. 52); US 2003/119125 (Claim 1); WO 2003/016475 (Claim 1); WO 2002/02634 (Claim 1).

(22) EphB2R (DRT, ERK, Hek5, EPHT3, Tyro5, GenBank accession no. NM_004442) Chan, J. and Watt, V. M., *Oncogene*, 1991, 6(6): 1057-1061; Oncogene, 1995, 10(5): 897-905; Annu. Rev. Neurosci., 1998, 21:309-345; Int. Rev. Cytol., 2000, 196:177-244; WO 2003/042661 (Claim 12); WO 2000/53216 (Claim 1; Page 41); WO 2004/065576 (Claim 1); WO 2004/020583 (Claim 9); WO 2003/004529 (Page 128-132); WO 2000/53216 (Claim 1; Page 42); Cross-references: MIM:600997; NP_004433.2; NM_004442_1.

(23) ASLG659 (B7h, GenBank accession no. AX092328) US20040101899 (Claim 2); WO 2003/104399 (Claim 11); WO 2004/000221 (FIG. 3); US 2003/165504 (Claim 1); US 2003/124140 (Example 2); US 2003/065143 (FIG. 60); WO 2002/102235 (Claim 13; Page 299); US 2003/091580 (Example 2); WO 2002/10187 (Claim 6; FIG. 10); WO 2001/94641 (Claim 12; FIG. 7b); WO 2002/02624 (Claim 13; FIG. 1A-1B); US 2002/034749 (Claim 54; Page 45-46); WO 2002/06317 (Example 2; Page 320-321, Claim 34; Page 321-322); WO 2002/71928 (Page 468-469); WO 2002/02587 (Example 1; FIG. 1); WO 2001/40269 (Example 3; Pages 190-192); WO 2000/36107 (Example 2; Page 205-207); WO 2004/053079 (Claim 12); WO 2003/004989 (Claim 1); WO 2002/71928 (Page 233-234, 452-453); WO 0116318.

(24) PSCA (Prostate stem cell antigen precursor, GenBank accession no. AJ297436) Reiter R. E., et al., *Proc. Natl. Acad. Sci. U.S.A.*, 1998, 95:1735-1740; Gu Z., et al., *Oncogene*, 2000, 19:1288-1296; Biochem. Biophys. Res. Commun., 2000, 275(3):783-788; WO 20040/22709; EP 1394274 (Example 11); US 2004/018553 (Claim 17); WO 2003/008537 (Claim 1); WO 2002/81646 (Claim 1; Page 164); WO 2003/003906 (Claim 10; Page 288); WO 2001/40309 (Example 1; FIG. 17); US 2001/055751 (Example 1; FIG. 1b); WO 2000/32752 (Claim 18; FIG. 1); WO 1998/51805 (Claim 17; Page 97); WO 1998/51824 (Claim 10; Page 94); WO 1998/40403 (Claim 2; FIG. 1B); Accession: O43653; EMBL; AF043498; AAC39607.1.

(25) GEDA (GenBank accession No. AY260763); AAP14954 lipoma HMGIC fusion-partner-like protein/pid=AAP14954.1—Homo sapiens Species: Homo sapiens (human) WO 2003/054152 (Claim 20); WO 2003/000842 (Claim 1); WO 2003/023013 (Example 3, Claim 20); US 2003/194704 (Claim 45); Cross-references: GI:30102449; AAP14954.1; AY260763_1.

(26) BAFF-R (B cell-activating factor receptor, BLyS receptor 3, BR3, GenBank accession No. AF116456); BAFF receptor/pid=NP_443177.1—Homo sapiens Thompson, J. S., et al., *Science*, 2001, 293(5537):2108-2111; WO 2004/058309; WO 2004/011611; WO 2003/045422 (Example; Page 32-33); WO 2003/014294 (Claim 35; FIG. 6B); WO 2003/035846 (Claim 70; Page 615-616); WO 2002/94852 (Col 136-137); WO 2002/38766 (Claim 3; Page 133); WO 2002/24909 (Example 3; FIG. 3); Cross-references: MIM: 606269; NP_443177.1; NM_052945_1; AF132600.

(27) CD22 (B-cell receptor CD22-B isoform, BL-CAM, Lyb-8, Lyb8, SIGLEC-2, FLJ22814, GenBank accession No. AK026467); Wilson, et al., *J. Exp. Med.*, 1991, 173: 137-146; WO 2003/072036 (Claim 1; FIG. 1); Cross-references: MIM:107266; NP_001762.1; NM_001771_1.

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, GenBank accession No. NP_001774.10) WO 2003/088808, US 2003/0228319; WO 2003/062401 (claim 9); US 2002/150573 (claim 4, pages 13-14); WO 9958658 (claim 13, FIG. 16); WO 9207574 (FIG. 1); U.S. Pat. No. 5,644,033; Ha, et al., *J. Immunol.*, 1992, 148(5):1526-1531; Mueller, et al., *Eur. J. Biochem.*, 1992, 22:1621-1625; Hashimoto, et al., *Immunogenetics*, 1994, 40(4):287-295; Preud'homme, et al., *Clin. Exp. Immunol.*, 1992, 90(1):141-146; Yu, et al., *J. Immunol.*, 1992, 148(2) 633-637; Sakaguchi, et al., *EMBO J.*, 1988, 7(11): 3457-3464.

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, GenBank accession No. NP_001707.1) WO 2004/040000; WO 2004/015426; US 2003/105292 (Example 2); U.S. Pat. No. 6,555,339 (Example 2); WO 2002/61087 (FIG. 1); WO 2001/57188 (Claim 20, page 269); WO 2001/72830

(pages 12-13); WO 2000/22129 (Example 1, pages 152-153, Example 2, pages 254-256); WO 1999/28468 (claim 1, page 38); U.S. Pat. No. 5,440,021 (Example 2, col 49-52); WO 9428931 (pages 56-58); WO 1992/17497 (claim 7, FIG. 5); Dobner, et al., *Eur. J. Immunol.,* 1992, 22:2795-2799; Barella, et al., *Biochem. J.,* 1995, 309:773-779.

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, GenBank accession No. NP_002111.1); Tonnelle, et al., *EMBO J.,* 1985, 4(11):2839-2847; Jonsson, et al., *Immunogenetics,* 1989, 29(6):411-413; Beck, et al., *J. Mol. Biol.,* 1992, 228:433-441; Strausberg, et al., *Proc. Natl. Acad. Sci USA,* 2002, 99:16899-16903; Servenius, et al., *J. Biol. Chem.,* 1987, 262:8759-8766; Beck, et al., *J. Mol. Biol.,* 1996, 255:1-13; Naruse, et al., *Tissue Antigens,* 2002, 59:512-519; WO 9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara, et al., *Immunogenetics,* 1989, 30(1):66-68; Larhammar, et al., *J. Biol. Chem.,* 1985, 260(26):14111-14119.

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3, GenBank accession No. NP_002552.2); Le, et al., *FEBS Lett.,* 1997, 418 (1-2):195-199; WO 2004/047749; WO 2003/072035 (claim 10); Touchman, et al., *Genome Res.,* 2000, 10:165-173; WO 2002/22660 (claim 20); WO 2003/093444 (claim 1); WO 2003/087768 (claim 1); WO 2003/029277 (page 82).

(32) CD72 (B-cell differentiation antigen CD72, Lyb-2), pI: 8.66, MW: 40225 TM: 1 [P] Gene Chromosome: 9p13.3, GenBank accession No. NP_001773.1) WO2004042346 (claim 65); WO 2003/026493 (pages 51-52, 57-58); WO 2000/75655 (pages 105-106); Von Hoegen, et al., *J. Immunol.,* 1990, 144(12):4870-4877; Strausberg, et al., *Proc. Natl. Acad. Sci USA,* 2002, 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis; 661 aa, pI: 6.20, MW: 74147 TM: 1 [P] Gene Chromosome: 5q12, GenBank accession No. NP_005573.1) US 2002/193567; WO 9707198 (claim 11, pages 39-42); Miura, et al., *Genomics,* 1996, 38(3):299-304; Miura, et al., *Blood,* 1998, 92:2815-2822; WO 2003/083047; WO 9744452 (claim 8, pages 57-61); WO 2000/12130 (pages 24-26).

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, GenBank accession No. NP_443170.1) WO 2003/077836; WO 2001/38490 (claim 6, FIG. 18E-1-18-E-2); Davis, et al., *Proc. Natl. Acad. Sci USA,* 2001, 98(17):9772-9777; WO 2003/089624 (claim 8); EP 1347046 (claim 1); WO 2003/089624 (claim 7).

(35) IRTA2 (Immunoglobulin superfamily receptor translocation associated 2, a putative immunoreceptor with possible roles in B cell development and lymphomagenesis; deregulation of the gene by translocation occurs in some B cell malignancies; 977 aa, pI: 6.88 MW: 106468 TM: 1 [P] Gene Chromosome: 1q21, GenBank accession No. Human: AF343662, AF343663, AF343664, AF343665, AF369794, AF397453, AK090423, AK090475, AL834187, AY358085; Mouse:AK089756, AY158090, AY506558; NP_112571.1. WO 2003/024392 (claim 2, FIG. 97); Nakayama, et al., *Biochem. Biophys. Res. Commun.,* 2000, 277(1):124-127; WO 2003/077836; WO 2001/38490 (claim 3, FIG. 18B-1-18B-2).

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; GenBank accession No. AF179274; AY358907, CAF85723, CQ782436 WO 2004/074320; JP 2004113151; WO 2003/042661; WO 2003/009814; EP 1295944 (pages 69-70); WO 2002/30268 (page 329); WO 2001/90304; US 2004/249130; US 2004/022727; WO 2004/063355; US 2004/197325; US 2003/232350; US 2004/005563; US 2003/124579; Horie, et al., *Genomics,* 2000, 67:146-152; Uchida, et al., *Biochem. Biophys. Res. Commun.,* 1999, 266:593-602; Liang, et al., *Cancer Res.,* 2000, 60:4907-12; Glynne-Jones, et al., *Int. J. Cancer,* 2001, 94(2):178-84.

(37) PMEL17 (silver homolog; SILV; D12S53E; PMEL17; SI; SIL); ME20; gp100) BC001414; BT007202; M32295; M77348; NM_006928; McGlinchey, R. P., et al., *Proc. Natl. Acad. Sci. U.S.A.,* 2009, 106(33):13731-13736; Kummer, M. P., et al., *J. Biol. Chem.,* 2009, 284 (4):2296-2306.

(38) TMEFF1 (transmembrane protein with EGF-like and two follistatin-like domains 1; Tomoregulin-1); $H_{7365}$; C9orf2; C9ORF2; U19878; X83961; NM_080655; NM_003692; Harms, P. W., *Genes Dev.,* 2003, 17(21):2624-2629; Gery, S., et al., Oncogene, 2003, 22(18):2723-2727.

(39) GDNF-Ra1 (GDNF family receptor alpha 1: GFRA1; GDNFR; GDNFRA; RETL1; TRNR1; RET1L; GDNFR-alpha1; GFR-ALPHA-1); U95847; BC014962; NM_145793 NM_005264; Kim, M. H., et al., *Mol. Cell. Biol.,* 2009, 29(8):2264-2277; Treanor, J. J., et al., *Nature,* 1996, 382(6586):80-83.

(40) Ly6E (lymphocyte antigen 6 complex, locus E; Ly67, RIG-E, SCA-2, TSA-1); NP_002337.1; NM_002346.2; de Nooij-van Dalen, A. G., et al., *Int. J. Cancer,* 2003, 103(6):768-774; Zammit, D. J., et al., *Mol. Cell. Biol.,* 2002, 22(3):946-952.

(41) TMEM46 (shisa homolog 2 (*Xenopus laevis*); SHISA2); NP_001007539.1; NM_001007538.1; Furushima, K., et al., *Dev. Biol.,* 2007, 306(2):480-492; Clark, H. F., et al., *Genome Res.,* 2003, 13(10):2265-2270.

(42) Ly6G6D (lymphocyte antigen 6 complex, locus G6D; Ly6-D, MEGT1); NP_067079.2; NM_021246.2; Mallya, M., et al., *Genomics,* 2002, 80(1):113-123; Ribas, G., et al., *J. Immunol.,* 1999, 163(1):278-287.

(43) LGR5 (leucine-rich repeat-containing G protein-coupled receptor 5; GPR49, GPR67); NP_003658.1; NM_003667.2; Salanti, G., et al., *Am. J. Epidemiol.,* 2009, 170(5):537-545; Yamamoto, Y., et al., Hepatology, 2003, 37(3):528-533.

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H., et al., *Cancer Sci.,* 2009 100(10):1895-1901; Narita, N., et al., *Oncogene,* 2009, 28(34):3058-3068.

(45) LY6K (lymphocyte antigen 6 complex, locus K; LY6K; HSJ001348; FLJ35226); NP_059997.3; NM_017527.3; Ishikawa, N. et al., *Cancer Res.,* 2007, 67(24):11601-11611; de Nooij-van Dalen, A. G., et al., *Int. J. Cancer,* 2003, 103(6):768-774.

(46) GPR19 (G protein-coupled receptor 19; Mm.4787); NP_006134.1; NM_006143.2; Montpetit, A. and Sinnett, D., *Hum. Genet.*, 1999, 105 (1-2):162-164; O'Dowd, B. F., et al., *FEBS Lett.*, 1996, 394(3):325-329.

(47) GPR54 (KISS1 receptor: KISS1R; GPR54; HOT7T175; AXOR12); NP_115940.2; NM_032551.4; Navenot, J. M., et al., *Mol. Pharmacol.*, 2009, 75(6):1300-1306; Hata, K., et al., *Anticancer Res.* 2009, 29(2):617-623.

(48) ASPHD1 (aspartate beta-hydroxylase domain containing 1; LOC253982); NP_859069.2; NM_181718.3; Gerhard, D. S., et al., *Genome Res.*, 2004, 14 (10B):2121-2127.

(49) Tyrosinase (TYR; OCA1A; OCA1A; tyrosinase; SHEP3); NP_000363.1; NM_000372.4; Bishop, D. T., et al., *Nat. Genet.*, 2009, 41(8):920-925; Nan, H., et al., *Int. J. Cancer*, 2009, 125(4):909-917.

(50) TMEM118 (ring finger protein, transmembrane 2: RNFT2; FLJ14627); NP_001103373.1; NM_001109903.1; Clark, H. F., et al., *Genome Res.*, 2003, 13(10):2265-2270; Scherer, S. E., et al., *Nature*, 2006, 440(7082):346-351.

(51) GPR172A (G protein-coupled receptor 172A; GPCR41; FLJ11856; D15Ertd747e); NP_078807.1; NM_024531.3; Ericsson, T. A., et al., *Proc. Natl. Acad. Sci. U.S.A.*, 2003, 100(11):6759-6764; Takeda, S., et al., *FEBS Lett.*, 2002, 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath, et al., *J. Clin. Invest.*, 1985, 75:756-56; Andrews, et al., *Blood*, 1986, 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer, K., *Curr. Opin. Struct. Biol.*, 1999, 9(5):585-90; van Rhenen, A., et al., *Blood*, 2007, 110(7):2659-66; Chen, C. H., et al., *Blood*, 2006, 107(4):1459-67; Marshall, A. S., et al., *Eur. J. Immunol.*, 2006, 36(8):2159-69; Bakker, A. B., et al., *Cancer Res.*, 2005, 64(22):8443-50; Marshall, A. S., et al., *J. Biol. Chem.*, 2004, 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

(54) CD70 (CD27 ligand: CD27-L): cytokine that binds to CD27) plays a role in T-cell activation and induces the proliferation of co-stimulated T-cells and enhances the generation of cytolytic T-cells. CD70 protein is expressed on highly activated lymphocytes such as T- and B-cell lymphomas (Israel, B. F., et al., *Mol. Cancer Ther.*, 2005, 4(12): 2037-44; O'Neill, R. E., et al., *J. Immunol.*, 2017, 199(10): 3700-3710; Leigh, N. D., et al., *J. Immunol.*, 2017, 199(1): 336-347; Itani, H. A., et al., *Circ. Res.*, 2016, 118(8):1233-43; Burchill, M. A., et al., *Eur. J. Immunol.*, 2015, 45(11): 3140-9; Allam, A., et al., *J. Immunol.*, 2014, 193(2):871-8).

(55) CLDN18.2 (Claudin-18 Spice Variant 2); CLDN18 encodes the human gene, Claudin 18. It may also be known as: Claudin-18; SFTA5; and SFTPJ. The encoded protein has an amino acid length of 261 and a mass of 27.9 kDa. CLDN18 is a member of the Claudin family (WO 2013/167295; WO 2016/166122). The tight junction molecule claudin 18 isotype 2 (CLDN 18.2) is a cancer-associated splice variant of Claudin 18. CLDN 18.2 is a 27.8 kDa transmembrane protein comprising four membrane spanning domains with two small extracellular loops (loop1 embraced by hydrophobic region 1 and hydrophobic region 2; loop2 embraced by hydrophobic regions 3 and 4). CLDN 18.2 is a highly selective gastric lineage antigen, exclusively expressed on short-lived differentiated gastric epithelial cells and not detectable in any other normal human tissue. The antigen is ectopically expressed at significant levels in a diversity of human cancers including gastroesophageal and pancreatic cancer (Sahin, U., et al., *Clin. Cancer Res.*, 2008, 14(23):7624-34). The CLDN18.2 protein is also frequently detected in lymph node metastases of gastric cancer and in distant metastases. CLDN 18.2 seems to be involved in proliferation of CLDN 18.2 positive tumor cells, since down regulation of the target by siRNA technology results in inhibition of proliferation of gastric cancer cells. 1MAB362 is a chimeric monoclonal antibody of IgGI subtype directed against CLDN 18.2. 1MAB362 recognizes the first extra-cellular domain of CLDN 1 8.2 with high affinity and specificity and does not bind to any other claudin family member including the closely related splice variant 1 of Claudin 18.

(56) CD151 (Cluster of differentiation 151, Tspan24, PETA-3, SFA-1); human gene from the Raph blood group. The protein encoded by CD151 gene is a member of the transmembrane 4 superfamily, also known as the tetraspanin family. Most of these members are cell-surface proteins that are characterized by the presence of four hydrophobic domains. The proteins mediate signal transduction events that play a role in the regulation of cell development, activation, growth and motility. This encoded protein is a cell surface glycoprotein that is known to complex with integrins and other transmembrane 4 superfamily proteins. It is involved in cellular processes including cell adhesion and may regulate integrin trafficking and/or function. This protein enhances cell motility, invasion and metastasis of cancer cells. Multiple alternatively spliced transcript variants that encode the same protein have been described for this gene (Berditchevski F., *J. Cell Sci.*, 2002, 114 (Pt 23):4143-51; Ashman, L. K., *J. Biol. Regul. Homeost. Agents*, 2003, 16(3):223-6; Sincock, P. M., et al., *J. Histochem. Cytochem.*, 1997, 45(4):515-25; Fitter S, et al., *Biochim. Biophys. Acta.*, 1998, 1398(1):75-85; Sincock, P. M., et al., *J. Cell Sci.*, 1999, 112 (Pt 6):833-44; Sterk, L. M., et al., *J. Cell Biol.*, 2000, 149(4):969-82; Zhang, X. A., *Mol. Biol. Cell.*, 2002, 13(1):1-11).

(57) ITGaV (integrin alpha-V, CD51; MSK8; VNRA; VTNR); a protein in humans is encoded by the ITGAV gene (Sosnoski, D. M., et al., *J. Clin. Invest.*, 1988, 81(6):1993-8). ITGAV encodes integrin alpha chain V. Integrins are heterodimeric integral membrane proteins composed of an alpha chain and a beta chain. Alpha V undergoes post-translational cleavage to yield disulfide-linked heavy and light chains that combine with multiple integrin beta chains to form different integrins. Among the known associating beta chains (beta chains 1,3,5,6, and 8: 'ITGB1', 'ITGB3', 'ITGB5', 'ITGB6', and 'ITGB8'), each can interact with extracellular matrix ligands; the alpha V beta 3 integrin, perhaps the most studied of these, is referred to as the Vitronectin receptor (VNR). In addition to adhesion, many integrins are known to facilitate signal transduction. Overexpression of the ITGAV gene is associated with progression and spread of colorectal cancer (Waisberg, J., et al., *Anticancer Res.*, 2014, 34(10):5599-607) and prostate cancer (Cooper, C. R., et al., *Neoplasia*. 2002, 4(3):191-4). Monoclonal antibodies intetumumab and abituzumab target this protein which is found on some tumor cells (Élez, E., et a., *Ann. Oncology*, 2015, 26(1):132-40).

Further exemplary antigens include, but are not limited to: (58) Nectin-4; (59) FGFR2; (60) FGFR3; (61) gpNMB; (62) GUCY2C; (63) CLDN6; (64) cMET; (65) CEACAM4; (66) CEACAM5; (67) CD29; (68) CD37; (69) CD352; (70) CD248; (71) MUC1; (72) CD123; (73) BCMA; (74) ADAM9; (75) 5T4; (76) P-cadherin; (77) CA9; (78) CD138; (79) CD166; (80) CD71; (81) CD22; (82) CD20; (83) CD74; (84) DLL3; (85) Folate Receptor alpha; (86) ITGa2; (87) ITGa3; (88) LAMP1; (89) LIV-1; (90) MMP14; (91) LRCC15; (92) MSLN; (93) PMSA; (94) PRLR; (95) PTK7; (96) SLAMF7; (97) SCL44A4; (98) SLTRK5; (99) TM4SF1; and (100) TROP2.

In certain embodiments of the present invention, TAA are selected from the group consisting of HER2, CD33, CD70, MUC1/CanAg, MUC16, CD151 and ITGaV.

Antibody-Drug Conjugate (Toxin-Linker-Antibody) Compounds

According to another aspect, the present invention relates to a compound or compounds of Formula (III):

T-L'-Ab  (III)

or a pharmaceutically acceptable salt thereof, wherein:
L' is a linker moiety;
T is a radical of Formula (I'):

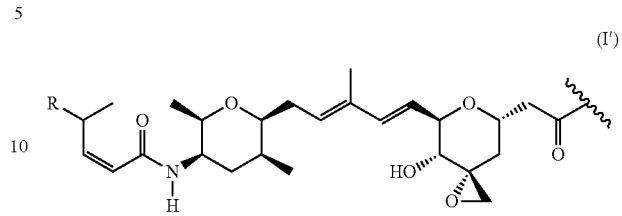

wherein:
R is selected from the selected from the group consisting of:
—$(CH_2)_n$—$R^1$; —$C_{5-6}$heteroaryl, optionally substituted with one or more of halogen, —$CF_3$, —$C_{1-6}$alkyl, and —O—$C_{1-6}$alkyl;
—$C(R^2)$=N—$R^3$;     —$CH(CF_3)NH(CH_2)_mCH_3$;
—$C(R^aR^b)NH(CH_2)_mCH_3$;
—$C(halogen)$=$CH(CH_2)_mCH_3$;    —$SO_2$—$NH(CH_2)_mCH_3$; —O(CO)-aryl; —O(CO)-heteroaryl;
—$NR^aR^b$; and —NH-heteroaryl;
wherein $R^1$ is —O—$CR^aR^b(CH_2)_mCH_3$ or —N—$CR^aR^b(CH_2)_mCH_3$;
wherein $R^a$ and $R^b$, together with the atoms to which they are joined, form a $C_{3-10}$ heterocyclyl ring;
$R^2$ is —CN or —$NH(CH_2)_mCH_3$;
$R^3$ is —$(CH_2)_mCH_3$ or —O—$(CH_2)_mCH_3$;
each n is independently 1, 2, or 3;
each m is independently 0, 1, 2, or 3; and
Ab is an antibody.

In certain exemplary embodiments, L' is selected from the group consisting of Formula ($B^1$), Formula ($B^2$), Formula ($B^3$), and Formula ($B^4$):

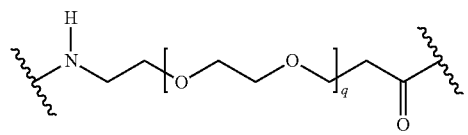

($B^1$)

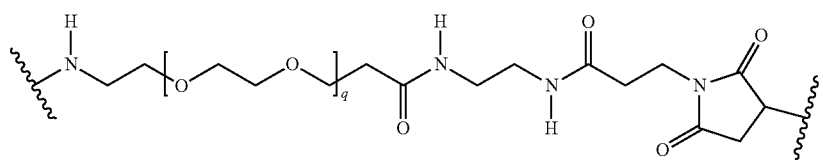

($B^2$)

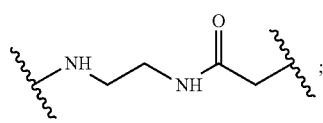

($B^3$)

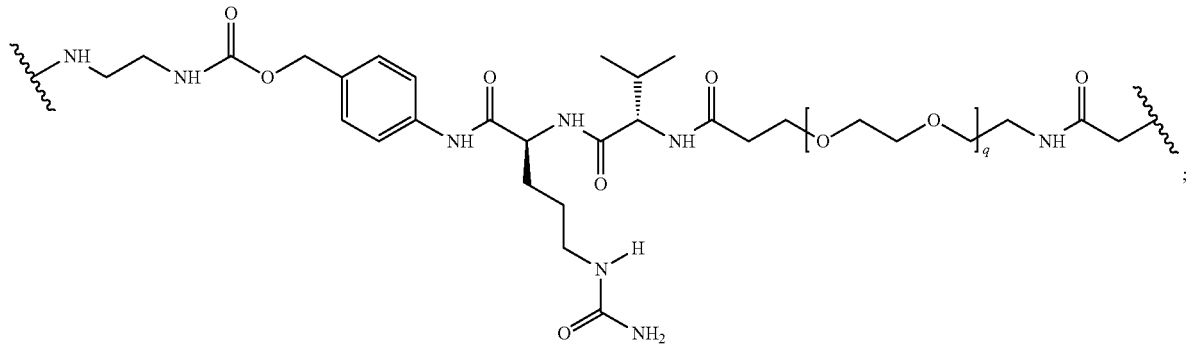
(B⁴)
wherein q is 3, 4, 5, 6, 7, 8, 9, or 10.
In certain exemplary embodiments, R is selected from the group consisting of:
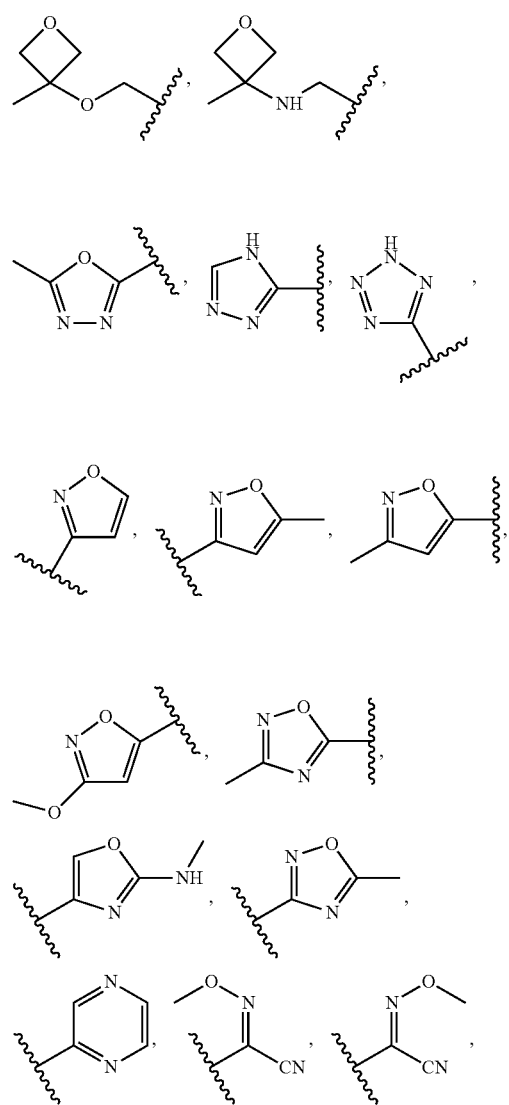
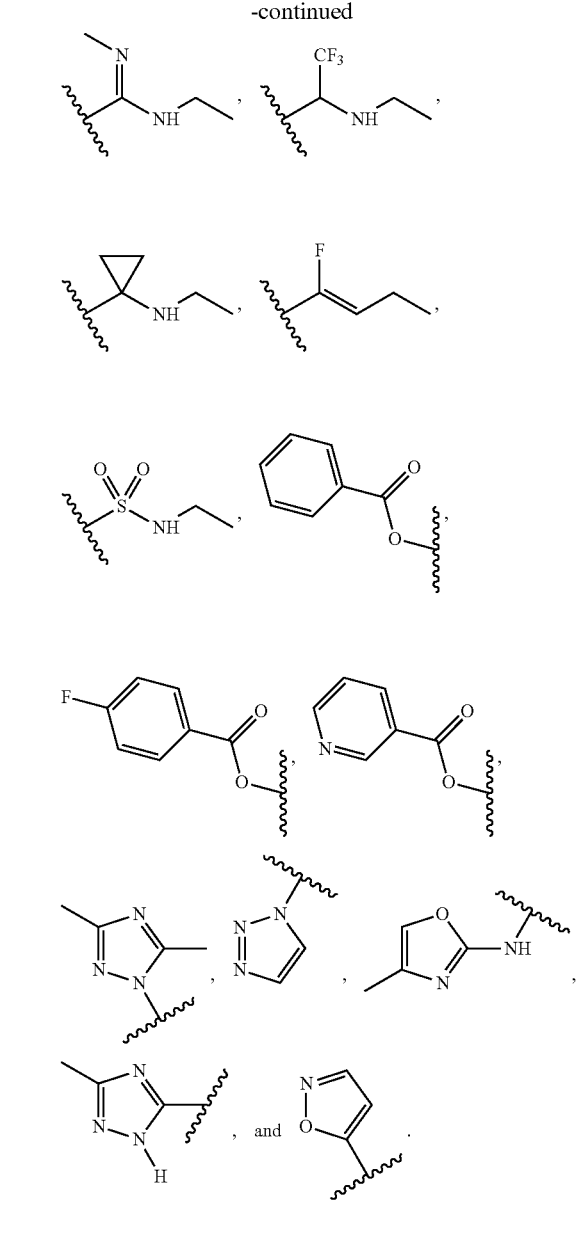

A non-limiting example of Formula (III) comprises the Formula (C¹):

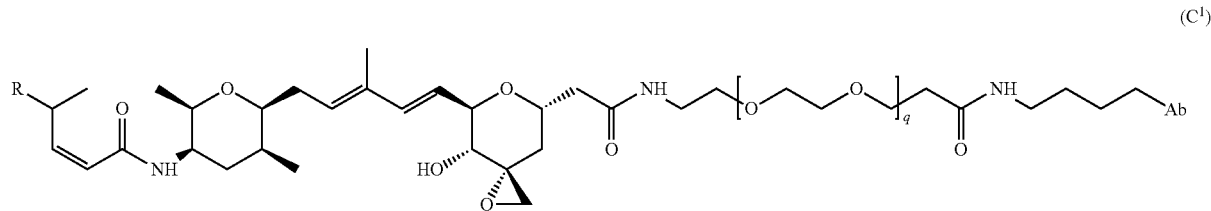

(C¹)

wherein R and q are as described above and Ab is an antibody as described above. A further non-limiting example of Formula (III) comprises Formula (C²):

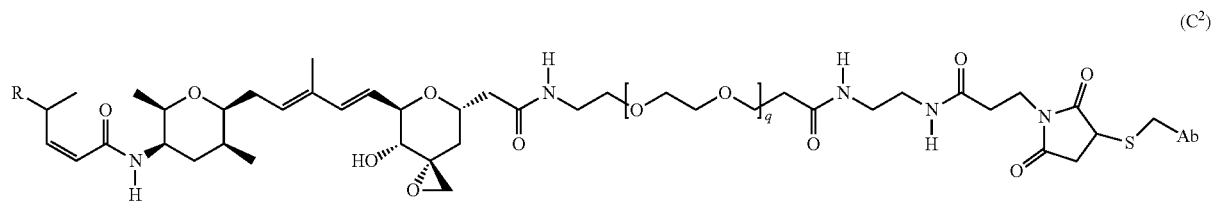

(C²)

wherein R is as described above and Ab is an antibody as described above. Another non-limiting example of Formula (III) comprises Formula (C³):

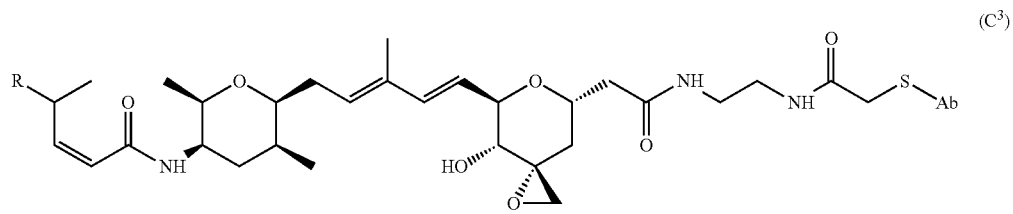

(C³)

wherein R is as described above and Ab is an antibody as described above. A further non-limiting example of Formula (III) comprises Formula (C⁴):

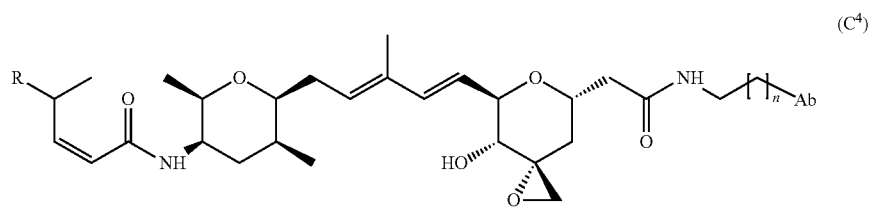

(C⁴)

wherein R is as described above, Ab is an antibody as described above, and n is 1, 2, or 3 as described above. Another non-limiting example of Formula (III) comprises Formula (C⁵):

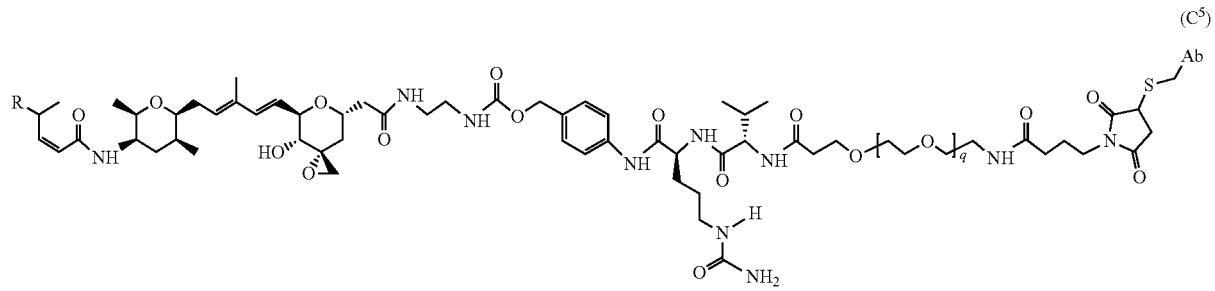

wherein R is as described above, Ab is an antibody as described above, and q is 3, 4, 5, 6, 7, 8, 9, or 10 as described above.

In an exemplary embodiment, the antibody binds to one or more tumor-associated or cell-surface receptors selected from (1)-(100):

(1) BMPR1B (bone morphogenetic protein receptor-type IB); (2) E16 (LAT1, SLC7A5); (3) STEAP1 (six transmembrane epithelial antigen of prostate); (4) MUC16 (0772P, CA125); (5) MPF (MPF, MSLN, SMR, megakaryocyte potentiating factor, mesothelin); (6) Napi2b (NAPI-3B, NPTIIb, SLC34A2, solute carrier family 34 (sodium phosphate), member 2, type II sodium-dependent phosphate transporter 3b); (7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B); (8) PSCA hlg (2700050C12Rik, C530008016Rik, RIKEN cDNA 2700050C12, RIKEN cDNA 2700050C12 gene); (9) ETBR (Endothelin type B receptor); (10) MSG783 (RNF124, hypothetical protein FLJ20315); (11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein); (12) TrpM4 (BR22450, FLJ20041, TRPM4, TRPM4B, transient receptor potential cation channel, subfamily M, member 4); (13) CRIPTO (CR, CR1, CRGF, CRIPTO, TDGF1, teratocarcinoma-derived growth factor); (14) CD21 (CR2 (Complement receptor 2) or C3DR (C3d/Epstein Barr virus receptor) or Hs 73792); (15) CD79b (CD79B, CD79β, IGb (immunoglobulin-associated beta), B29); (16) FcRH2 (IFGP4, IRTA4, SPAP1A (SH2 domain containing phosphatase anchor protein 1a), SPAP1B, SPAP1C); (17) HER2; (18) NCA; (19) MDP; (20) IL20Rα; (21) Brevican; (22) EphB2R; (23) ASLG659; (24) PSCA; (25) GEDA; (26) BAFF-R (B cell-activating factor receptor, BLyS receptor 3, BR3); (27) CD22 (B-cell receptor CD22-B isoform); (28) CD79a (CD79A, CD79α, immunoglobulin-associated alpha); (29) CXCR5 (Burkitt's lymphoma receptor 1); (30) HLA-DOB (Beta subunit of MHC class II molecule (Ia antigen)); (31) P2X5 (Purinergic receptor P2X ligand-gated ion channel 5); (32) CD72 (B-cell differentiation antigen CD72, Lyb-2); (33) LY64 (Lymphocyte antigen 64 (RP105), type I membrane protein of the leucine rich repeat (LRR) family); (34) FcRH1 (Fc receptor-like protein 1); (35) FcRH5 (IRTA2, Immunoglobulin superfamily receptor translocation associated 2); (36) TENB2 (putative transmembrane proteoglycan); (37) PMEL17 (silver homolog: SILV; D12S53E; PMEL17; SI; SIL); (38) TMEFF1 (transmembrane protein with EGF-like and two follistatin-like domains 1; Tomoregulin-1); (39) GDNF-Ra1 (GDNF family receptor alpha 1: GFRA1; GDNFR; GDNFRA; RETL1; TRNR1; RETL1; GDNFR-alpha1; GFR-ALPHA-1); (40) Ly6E (lymphocyte antigen 6 complex, locus E; Ly67, RIG-E, SCA-2, TSA-1); (41) TMEM46 (shisa homolog 2 (Xenopus laevis); SHISA2); (42) Ly6G6D (lymphocyte antigen 6 complex, locus G6D; Ly6-D, MEGT1); (43) LGR5 (leucine-rich repeat-containing G protein-coupled receptor 5; GPR49, GPR67); (44) RET (ret proto-oncogene; MEN2A; HSCR1; MEN2B; MTC1; PTC; CDHF12; Hs.168114; RET51; RET-ELE1); (45) LY6K (lymphocyte antigen 6 complex, locus K; LY6K; HSJ001348; FLJ35226); (46) GPR19 (G protein-coupled receptor 19; Mm.4787); (47) GPR54 (KISS1 receptor; KISS1R; GPR54; HOT7T175; AXOR12); (48) ASPHD1 (aspartate beta-hydroxylase domain containing 1; LOC253982); (49) Tyrosinase (TYR; OCAIA; OCA1A; tyrosinase; SHEP3); (50) TMEM118 (ring finger protein, transmembrane 2; RNFT2; FLJ14627); (51) GPR172A (G protein-coupled receptor 172A; GPCR41; FLJ11856; D15Ertd747e); (52) CD33; (53) CLL-1; (54) CD70 (CD27 ligand; CD27-L); (55) CLDN18.2 (Claudin-18 Spice Variant 2); (56) CD151 (Cluster of differentiation 151, Tspan24, PETA-3, SFA-1); (57) ITGaV (integrin alpha-V, CD51; MSK8; VNRA; VTNR); (58) Nectin-4; (59) FGFR2; (60) FGFR3; (61) gpNMB; (62) GUCY2C; (63) CLDN6; (64) cMET; (65) CEACAM4; (66) CEACAM5; (67) CD29; (68) CD37; (69) CD352; (70) CD248; (71) MUC1; (72) CD123; (73) BCMA; (74) ADAM9; (75) 5T4; (76) P-cadherin; (77) CA9; (78) CD138; (79) CD166; (80) CD71; (81) CD22; (82) CD20; (83) CD74; (84) DLL3; (85) Folate Receptor alpha; (86) ITGa2; (87) ITGa3; (88) LAMP1; (89) LIV-1; (90) MMP14; (91) LRCC15; (92) MSLN; (93) PMSA; (94) PRLR; (95) PTK7; (96) SLAMF7; (97) SCL44A4; (98) SLTRK5; (99) TM4SF1; and (100) TROP2.

In certain exemplary embodiments of the invention, the antibody is bound via an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase.

In certain embodiments, the present invention relates to any of the aforementioned antibody-drug conjugates and attendant definitions, wherein the antibody-drug conjugate comprises between 1, 2, 3, 4, 5, 6, 7, 8, 9 or 10 compounds of the invention. In certain exemplary embodiments, the antibody-drug conjugate comprises 1, 2, 3 or 4 compounds of the invention.

The number of toxins covalently linked to an antibody may vary according to the specific toxic compound and antibody. In one embodiment, 1 to 4 toxins are linked. In another embodiment from about 1 to about 4 toxins are linked. In a further embodiment, from about 1 to about 6 toxins are linked. In embodiments where more than one toxin is linked, the antibody (Ab) of Formula (III) has multiple T-L'-units covalently bonded to it.

The loading (drug/antibody ratio) of an antibody-drug conjugate may be controlled in different ways, and for example, by: (i) limiting the molar excess of the drug-linker intermediate Formula (II) compound relative to antibody, (ii) limiting the conjugation reaction time or temperature, and (iii) partial or limiting reductive conditions for cysteine thiol modification.

It is to be understood that where more than one nucleophilic group reacts with a drug, then the resulting product is a mixture of Formula (III) antibody-drug conjugate compounds with a distribution of one or more drug moieties attached to an antibody. The average number of drugs per antibody may be calculated from the mixture by a dual ELISA antibody assay, which is specific for antibody and specific for the drug. Individual antibody-drug conjugate molecules may be identified in the mixture by mass spectroscopy and separated by HPLC, e.g. hydrophobic interaction chromatography (see, e.g., McDonagh, et al., *Prot. Engr. Design Sel.*, 2006, 19(7):299-307; Hamblett, et al., *Clin. Cancer Res.*, 2004, 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al., "Controlling the location of drug attachment in antibody-drug conjugates," Abstract No. 627, American Association for Cancer Research, 2004 Annual Meeting, March 27-31, 2004, Proceedings of the AACR, Volume 45, March 2004). In certain embodiments, a homogeneous antibody-drug conjugate with a single loading value may be isolated from the conjugation mixture by electrophoresis or chromatography.

In Vitro Cell Proliferation Assays

The cytotoxic drug compounds and the antibody-drug conjugates of the invention can be evaluated for their ability to suppress the proliferation of various cancer cell lines in vitro.

Generally, the cytotoxic or cytostatic activity of a cytotoxic drug or ADC is measured by: exposing mammalian cells having receptor proteins, e.g. HER2, to the antibody of the ADC in a cell culture medium, culturing the cells for a period from about 6 hours to about 5 days, and measuring cell viability. Cell-based in vitro assays are used to measure viability (proliferation), cytotoxicity, and induction of apoptosis (caspase activation) of the ADC of the invention.

For example, the in vitro potency of a cytotoxic drug or ADC is measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713; and 5,700,670). This cell proliferation assay determines the number of viable cells in culture based on quantitation of the ATP present, an indicator of metabolically active cells (Crouch, et al., *J. Immunol.* Meth., 1993, 160:81-88; U.S. Pat. No. 6,602,677). The CellTiter-Glo® Assay is conducted in 96-well format, making it amenable to automated high-throughput screening (HTS) (Cree, et al., *AntiCancer Drugs*, 1995, 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with cytotoxic drug compounds or ADC, or they may be treated and separated from cytotoxic drug compounds or ADC. Generally, cells treated briefly, i.e., 3 hours, showed the same potency effects as continuously treated cells.

In Vivo Efficacy

The in vivo efficacy of a cytotoxic drug or ADC of the invention can be tested by tumor xenograft studies in mice to measure target-dependent and dose-dependent potency in inhibition of tumor growth. Efficacy of the cytotoxic drug or ADC may correlate with target antigen expression of the tumor cells.

The efficacy of the cytotoxic drug or ADC is measured in vivo by implanting allografts or xenografts of cancer cells in rodents and treating the tumors with the cytotoxic drug or ADC. Variable results are to be expected depending on the cell line, the dose of the cytotoxic drug, the specificity of antibody binding of the ADC to receptors present on the cancer cells, dosing regimen, and other factors. The in vivo efficacy of the cytotoxic drug or ADC can be measured using a transgenic explant mouse model expressing moderate to high levels of a tumor-associated antigen, including Her2-expressing KPL4, and CD22-expressing BJAB. Subjects may be treated once with the cytotoxic drug or ADC and monitored over several, e.g. 3-6, weeks to measure the time to tumor doubling, log cell kill, and tumor shrinkage. Follow up dose-response and multi-dose experiments may be conducted.

For example, the in vivo efficacy of an anti-HER2 ADC of the invention can be measured by a high expressing HER2 transgenic explant mouse model (Phillips, et al., *Cancer Res.*, 2008, 68:9280-90). An allograft is propagated from the Fo5 mmtv transgenic mouse which does not respond to, or responds poorly to, HERCEPTIN® (Genentech, Inc.) therapy. Subjects are treated once or more with ADC at certain dose levels (mg/kg) and placebo buffer control (Vehicle) and monitored over two weeks or more to measure the time to tumor doubling, log cell kill, and tumor shrinkage.

Pharmaceutical Compositions and Methods of Administration

In other embodiments, another aspect of the invention relates to pharmaceutical compositions or dosage forms including an effective amount of a compound of the invention and/or antibody-drug conjugate thereof and a pharmaceutically acceptable carrier or vehicle.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention and/or conjugate thereof to be bioavailable upon administration of the composition to a patient. Compositions can take the form of one or more dosage units, where for example, a tablet can be a single dosage unit, and a container of a compound of the invention and/or antibody-drug conjugate thereof in liquid form can hold a plurality of dosage units.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringers solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a compound of the invention and/or antibody-drug conjugate thereof that is effective in the treatment of a particular disorder or condition will depend on the nature of the disorder or condition, and can be determined by standard clinical techniques. In addition, in vitro or in vivo assays can be employed to help identify optimal dosage ranges. The precise dose to be utilized in the compositions will also depend on the route of administration, and should be decided according to the judgment of the practitioner and each patient's circumstances. The specific dose level for any particular individual will depend upon a variety of factors including the activity of the compound or drug-antibody conjugate, the age, body weight, general physical and mental health, genetic factors, environmental influences, sex, diet, time of administration, route of administration, rate of excretion, and the severity of the particular problem being treated.

The compositions comprise an effective amount of a compound of the invention and/or antibody-drug conjugate thereof such that a suitable dosage will be obtained. Typically, this amount is at least about 0.01% of a compound of the invention and/or antibody-drug conjugate thereof by weight of the composition. In an exemplary embodiment, pharmaceutical compositions are prepared so that a parenteral dosage unit contains from about 0.01% to about 2% by weight of the amount of a compound of the invention and/or antibody-drug conjugate thereof.

For intravenous administration, the composition can comprise from about 0.01 to about 100 mg of a compound of the invention and/or antibody-drug conjugate thereof per kg of the patient's body weight. In one aspect, the composition can include from about 1 to about 100 mg of a compound of the invention and/or antibody-drug conjugate thereof per kg of the patient's body weight. In another aspect, the amount administered will be in the range from about 0.1 to about 25 mg/kg of body weight of a compound of the invention and/or antibody-drug conjugate thereof.

Generally, the dosage of a compound of the invention and/or antibody-drug conjugate thereof administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In a further aspect, the dosage administered is between about 1 mg/kg to about 3 mg/kg of the patient's body weight.

In specific embodiments, it can be desirable to administer one or more compounds of the invention and/or antibody-drug conjugates thereof locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the compound of the invention and/or antibody-drug conjugate thereof can be delivered in a controlled release system, such as but not limited to, a pump or various polymeric materials can be used. In yet another embodiment, a controlled-release system can be placed in proximity of the target of the compound of the invention and/or antibody-drug conjugate thereof, e.g., the liver, thus requiring only a fraction of the systemic dose.

The term "carrier" refers to a diluent, adjuvant or excipient, with which a compound or antibody-drug conjugate thereof is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

In an embodiment, the compound of the invention and/or antibody-drug conjugate thereof are formulated in accordance with procedures known to those skilled in the art for the manufacture of a pharmaceutical composition adapted for intravenous administration. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule indicating the quantity of active agent. Where a compound of the invention and/or antibody-drug conjugate thereof is to be administered by infusion, it can be dispensed, for example, with an infusion bottle containing sterile pharmaceutical grade water or saline. Where the compound of the invention and/or antibody-drug conjugate thereof is administered by injection, an ampoule of sterile water for injection or saline can be provided so that the ingredients can be mixed prior to administration.

Whether in solid or liquid form, the present compositions can include an additional therapeutic agent(s) used in the treatment of cancer. For example, compounds or their antibody-drug conjugates can be administered in combination with, including antibodies, alkylating agents, angiogenesis inhibitors, antimetabolites, DNA cleavers, DNA cross-linkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, beta-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

Therapeutic Uses of Compounds and Antibody-Drug Conjugates

Another aspect of the invention relates to a method of using the compounds of the invention, their antibody-drug conjugates, and pharmaceutical compositions thereof for treating cancer. In certain embodiments, the conjugates provide conjugation-specific tumor or cancer drug targeting, thus reducing general toxicity of the compounds of the invention. In another embodiment, the antibody unit binds to the tumor cell or cancer cell. In another embodiment, the antibody unit binds to a tumor cell or cancer cell antigen which is on the surface of the tumor cell or cancer cell. In another embodiment, the antibody unit binds to a tumor cell or cancer cell antigen which is an extracellular matrix protein associated with the tumor cell or cancer cell. The specificity of the antibody unit for a particular tumor cell or cancer cell can be important for determining those tumors or cancers that are most effectively treated.

Particular types of cancers that can be treated with a compound of the invention and/or antibody-drug conjugate thereof, include but are not limited to, carcinomas of the bladder, breast, cervix, colon, endometrium, kidney, lung, esophagus, ovary, prostate, pancreas, skin, stomach, and testes; and blood born cancers including but not limited to leukemias and lymphomas.

In one aspect, an antibody-drug conjugate provided herein is used in a method of inhibiting proliferation of a cancer cell, the method comprising exposing the cell to the antibody-drug conjugate under conditions permissive for binding of the antibody or antibody-drug conjugates to a tumor-associated antigen on the surface of the cell, thereby inhibiting the proliferation of the cell. In certain embodiments, the method is an in vitro or an in vivo method. In further embodiments, the cell is a lymphocyte, lymphoblast, monocyte, or myelomonocyte cell.

In another aspect, a cytotoxic drug compound or ADC for use as a medicament is provided. In further aspects, a cytotoxic drug compound or ADC for use in a method of treatment is provided. In certain embodiments, a cytotoxic drug compound or ADC for use in treating cancer is provided. In certain embodiments, the invention provides a cytotoxic drug compound or ADC for use in a method of treating an individual comprising administering to the individual an effective amount of the cytotoxic drug compound or ADC. In one such embodiment, the method further comprises administering to the individual an effective amount of at least one additional therapeutic agent, e.g., as described herein.

In a further aspect, the invention provides for the use of a cytotoxic drug compound or ADC in the manufacture or preparation of a medicament. In one embodiment, the medicament is for treatment of cancer, the method comprising administering to an individual having cancer an effective amount of the medicament. In one such embodiment, the method further comprises administering to the individual an effective amount of at least one additional therapeutic agent, e.g., as described herein.

In a further aspect, the invention provides a method for treating cancer. In one embodiment, the method comprises administering to an individual having such cancer, characterized by detection of a tumor-associated expressing antigen, an effective amount of an antibody-drug conjugate of the invention. In one such embodiment, the method further comprises administering to the individual an effective amount of at least one additional therapeutic agent.

Cytotoxic drug compounds or ADC of the invention can be used either alone or in combination with other agents in a therapy. For instance, a cytotoxic drug compound or ADC of the invention may be co-administered with at least one additional therapeutic agent, such as a chemotherapeutic agent.

Such combination therapies noted herein encompass combined administration (where two or more therapeutic agents are included in the same or separate formulations), and separate administration, in which case, administration of the cytotoxic drug compound or ADC of the invention can occur prior to, simultaneously, and/or following, administration of the additional therapeutic agent and/or adjuvant. Cytotoxic drug compounds or ADC of the invention can also be used in combination with radiation therapy.

Cytotoxic drug compounds or ADC of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

The following examples are offered by way of illustration and not by way of limitation.

EXAMPLES

Synthetic Experimental Procedures

Experiments are generally carried out under inert atmosphere (nitrogen or argon), particularly in cases where oxygen- or moisture-sensitive reagents or intermediates are employed. Commercial solvents and reagents are generally used without further purification, including anhydrous solvents where appropriate. Mass spectrometry data is reported from either liquid chromatography-mass spectrometry (LCMS) or atmospheric pressure chemical ionization (APCI). Chemical shifts for nuclear magnetic resonance (NMR) data are expressed in parts per million (ppm, δ) referenced to residual peaks from the deuterated solvents employed.

In general, reactions are followed by thin layer chromatography, LCMS or HPLC, and subjected to work-up when appropriate. Purifications may vary between experiments: in general, solvents and the solvent ratios used for eluents/gradients are chosen to provide appropriate retention times. Unless otherwise specified, reverse phase HPLC fractions are concentrated via lyophilization/freeze-drying. Intermediate and final compounds are stored at (0° C.) or room temperature in closed vials or flasks under nitrogen.

General Procedure A1. Preparation of Thailanstatin Analog Toxin Compounds

The first step in preparing compounds of the invention with the above-described R groups involves coupling a carboxylic acid containing the R group, Formula (IV), to amino pyran (Compound 8) to produce intermediate amide Formula (V).

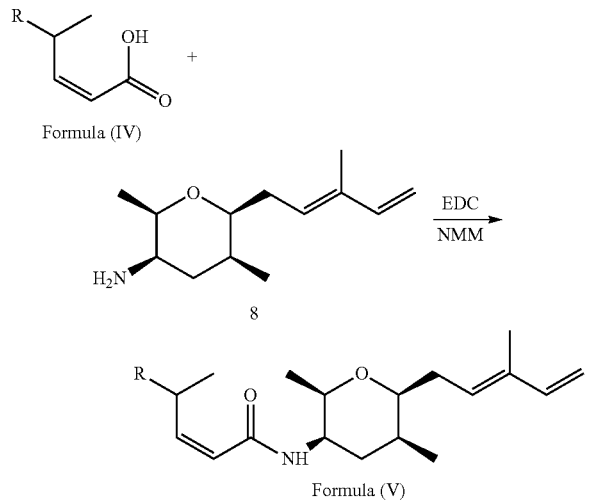

N-methylmorpholine (NMM) (0.12 mL, 1.0 mmol, 6.0 equiv), 1-ethyl-3-(dimethylaminopropyl)carbodiimide (EDCI) (196 mg, 1.0 mmol, 6.0 equiv), and a solution of acid Formula (IV) (108 mg, 0.68 mmol, 2.0 equiv) in dichloromethane (0.6 mL) were added sequentially to a stirred solution of amine 8 dissolved in dichloromethane (5 mL) at 25° C. After 2 h, the reaction mixture was quenched with a saturated aqueous solution of ammonium chloride (5.0 ml), and the phases were separated. The aqueous layer was extracted with EtOAc (3×2 ml), and the combined organic layers were dried with anhydrous sodium sulfate and concentrated in vacuo. The obtained residue was purified by flash column chromatography (silica gel, 10-30% ethyl acetate in hexanes) to provide the amide Formula (V) (74 mg, 0.24 mmol, 73%) as a colorless oil.

Intermediate amide Formula (V) was converted to Formula (I), where X is methyl, essentially according to the procedure described by A. K. Ghosh et al. (*J. Org. Chem.*, 2018, 83(9):5187-5198).

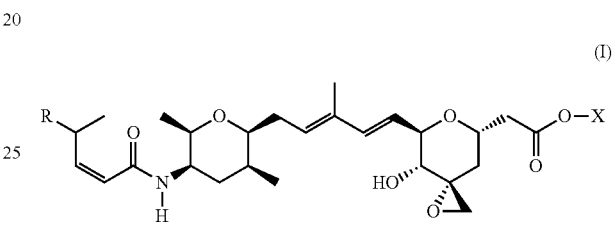

General Procedure A2. Preparation of Thailanstatin Analog Toxin Compounds

Alternatively, the first step in preparing compounds of the invention with the above-described R groups involves coupling a carboxylic acid containing the R group, Formula (IV), to amino pyran (2R,3R,5S,6S)-2, 5-dimethyl-6-((E)-3-methylpenta-2,4-dien-1-yl)tetrahydro-2H-pyran-3-amine (Compound 8) to produce the intermediate amide of Formula (V). The intermediate amide of Formula (V) is reacted with methyl 2-((3R,5S,7R,8R)-8-hydroxy-7-vinyl-1, 6-dioxaspiro [2.5]octan-5-yl)acetate (Compound 9) using Grubb's $2^{nd}$ Generation Catalyst (Grubb's-II catalyst to afford the compound of Formula (I), where X is methyl.

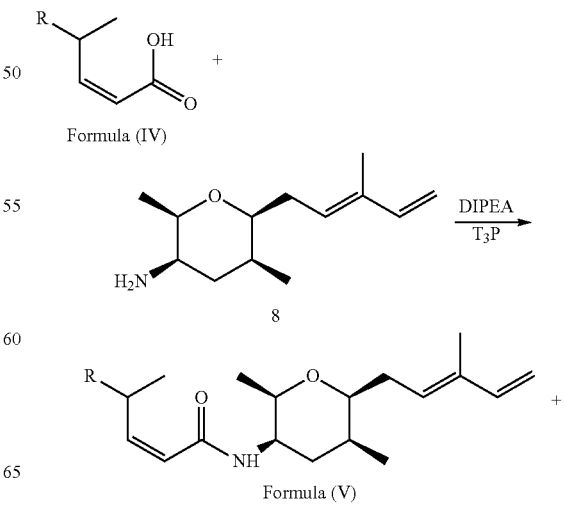

General Procedure B1. Preparation of Toxin-Linker Compounds

Compound 8 (2 equiv.) and the carboxylic acid of Formula (IV) (1 equiv.) were dissolved in tetrahydrofuran (THF) and N,N-diisopropylethylamine (DIPEA) (8.3 equiv.) and T₃P® (propylphosphonic anhydride; 50% in ethyl acetate) (5 equiv.) were added at room temperature. The reaction mixture was stirred for approximately three hours until the starting materials were consumed as determined by thin-layer chromatography (TLC). The mixture was concentrated in vacuo to obtain crude product. The crude product was purified by column chromatography to afford the desired intermediate amide of Formula (V).

The purified intermediate amide of Formula (V) (1 equiv.) was dissolved in dichloromethane (DCM) and Compound 9 (2 equiv.) and Grubb's-II catalyst (3.3 equiv.) were added with stirring at room temperature under argon atmosphere. The mixture was stirred at 40° C. for approximately 5 hours until the starting materials were consumed as determined by TLC. The reaction mixture was filtered through a celite pad and washed with DCM. The solvent was removed in vacuo to obtain the crude product, which was purified by preparative HPLC to afford the compound of Formula (I).

Synthesis of the toxin-Linker compounds of the invention with the above-described R groups involves forming an amide bond between the carboxylic acid moiety on Formula (I) and an amine on the chosen Linker to provide Formula (II).

A mixture of toxin of Formula (I) (0.47 mmol, 1.0 eq), 1-[bis(dimethylamino)methylene]-1H-1,2,3-triazolo[4,5-b]pyridinium 3-oxide hexafluorophosphate (HATU) (0.58 mmol, 1.2 eq) and DIEA (Hunigs base, 0.1 mL) in DMF (2.0 mL) is stirred at ambient temperature for 60 min. To the mixture was added the linker (0.50 mmol, 1.06 eq) along with DIEA (Hunigs base) (0.1 mL). The resulting mixture is stirred for 30 mins. The reaction is subjected to aqueous work up. The desired Formula (II) product containing the toxin coupled to the linker is obtained by further purification by flash chromatography.

General Procedure B2. Preparation of Toxin-Linker Compounds

Alternatively, the synthesis of the toxin-linker compounds of the invention with the above-described R and L groups may be prepared as shown in Scheme (I), Scheme (II) or Scheme (III).

Scheme (I)

-continued
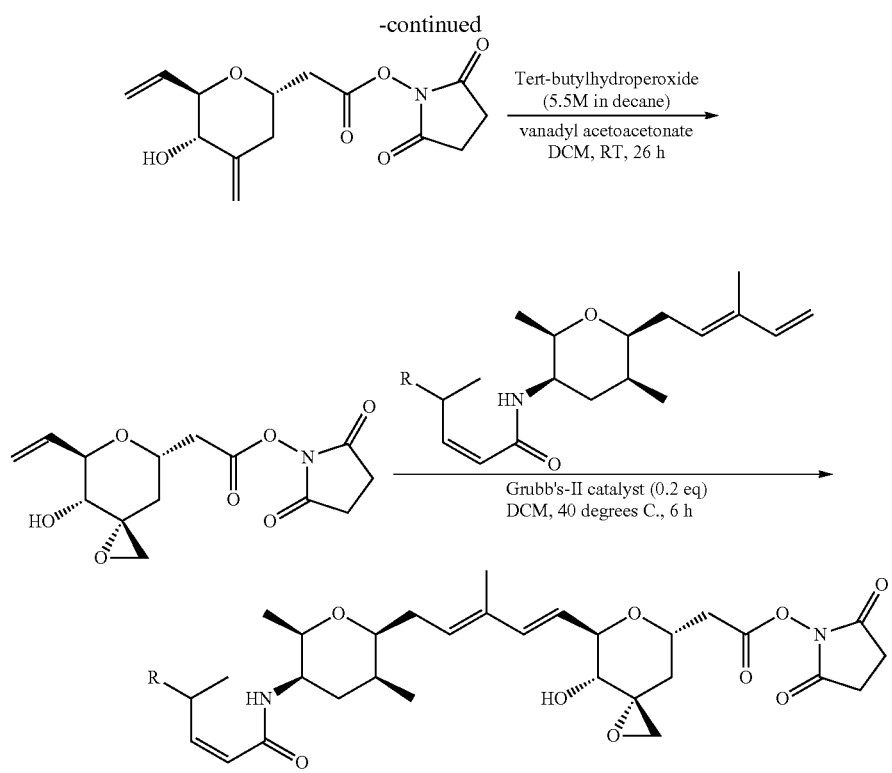
Scheme (II)
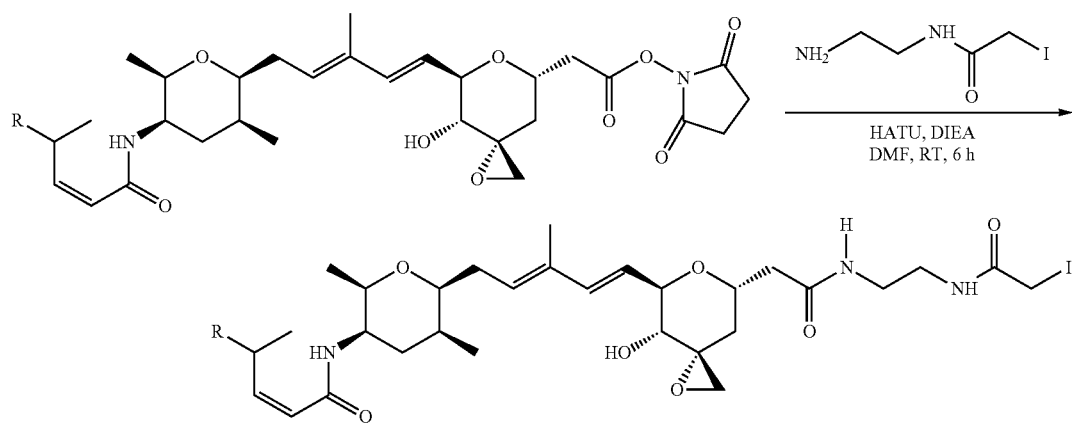
Scheme (III)
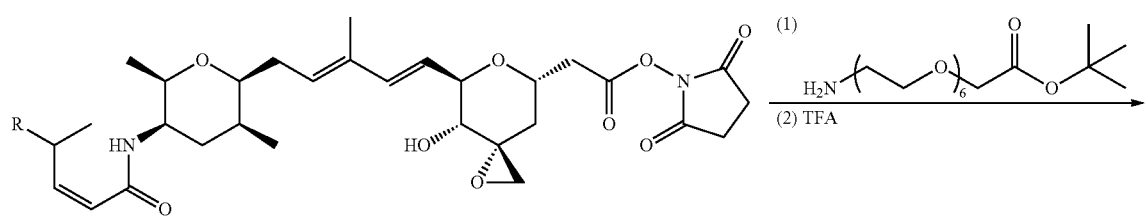

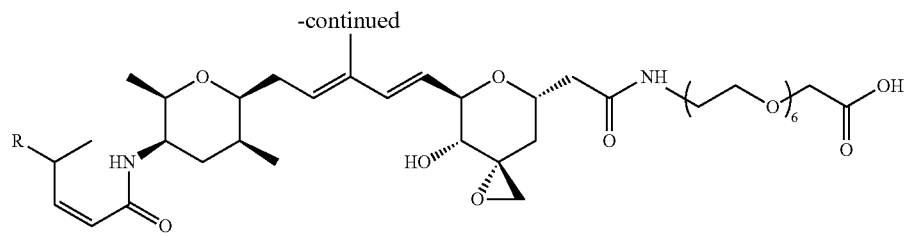

General Procedure C1. Preparation of Antibody-Drug Conjugates

Commercially available therapeutic antibody (Ab) is dialyzed into Dulbecco's Phosphate Buffered Saline (DPBS, Lonza). The dialyzed antibody (5-10 mg/mL) is then reacted with the toxin-linker compound of Formula (II) (3-12 equivalents) 10 mM in dimethyl sulfoxide (DMSO)) containing the reactive N-hydroxysuccinimide ester or the maleimide at room temperature for 2 h in 50 mM borate buffer pH 8.7. In some cases, 50 mM borate buffer pH 8.7 is substituted by Dulbecco's Phosphate Buffered Saline (DPBS, Lonza). In some cases, to improve the solubility/reactivity of the linker-toxin, dimethylacetamide (DMA) or DMSO is added to achieve 10-15% (v/v) total organic solvent component in final reaction mixture. The reaction mixture is then buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated and buffer exchanged in to 10 mM Sodium succinate buffer, 5.4% trehalose pH 5.1 using GE Healthcare Sephadex G-25 M buffer exchange columns per manufacturer's instructions. The ADC Formula (III) is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Procedure C2. Alternative Preparation of Antibody-Drug Conjugates

Alternatively, after reduction and reoxidation to prepare for conjugation, a cysteine-engineered antibody is dissolved in PBS (phosphate buffered saline) buffer and chilled on ice. An excess, from about 1.5 molar to 20 equivalents of a drug-linker intermediate according to Formula (II), activated with a thiol-reactive group such as pyridyl disulfide, maleimide, or bromoacetamide, is dissolved in DMSO, diluted in acetonitrile and water, and added to the chilled, reduced, and reoxidized antibody in PBS. Typically the drug-linker is added from a DMSO stock at a concentration of about 20 mM in 50 mM Tris, pH 8, to the antibody and monitored until the reaction is complete from about 1 to about 24 hours as determined by LC-MS analysis of the reaction mixture. When the reaction is complete, an excess of a capping reagent such as ethyl maleimide is added to quench the reaction and cap any unreacted antibody thiol groups. The conjugation mixture may be loaded and eluted through a HiTrap SP FF column to remove excess drug-linker and other impurities. The reaction mixture is concentrated by centrifugal ultrafiltration and the cysteine engineered antibody-drug conjugate is purified and desalted by elution through G25 resin in PBS, filtered through 0.2 μm filters under sterile conditions, and frozen for storage.

For example, the crude antibody-drug conjugate is applied to a cation exchange column after dilution with 20 mM sodium succinate, pH 5. The column is washed with at least 10 column volumes of 20 mM sodium succinate, pH 5, and the antibody is eluted with PBS. The antibody-drug conjugates are formulated into 20 mM His/acetate, pH 5, with 240 mM sucrose using gel filtration columns. The antibody-drug conjugates are characterized by UV spectroscopy to determine protein concentration, analytical SEC (size-exclusion chromatography) for aggregation analysis and LC-MS before and after treatment with Lysine C endopeptidase.

Example 1

Synthesis of (Z)-5-((2R, 3R, 5S, 6S)-6-((2E, 4E)-5-((3R, 4R, 5R, 7S)-4-hydroxy-7-(2-methoxy-2-oxo-ethyl)-1,6-dioxaspiro[2.5]octan-5-yl)-3-methylpenta-2,4-dienyl)-2,5-dimethyltetrahydro-2H-pyran-3-ylamino)-5-oxopent-3-en-2-yl benzoate, Compound 1

Part A:

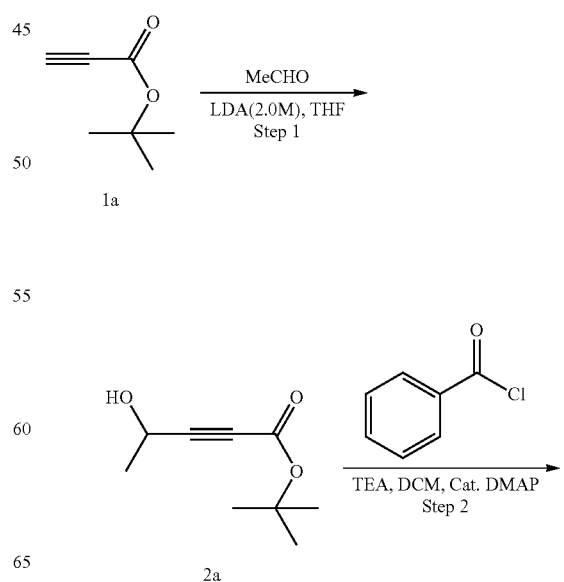

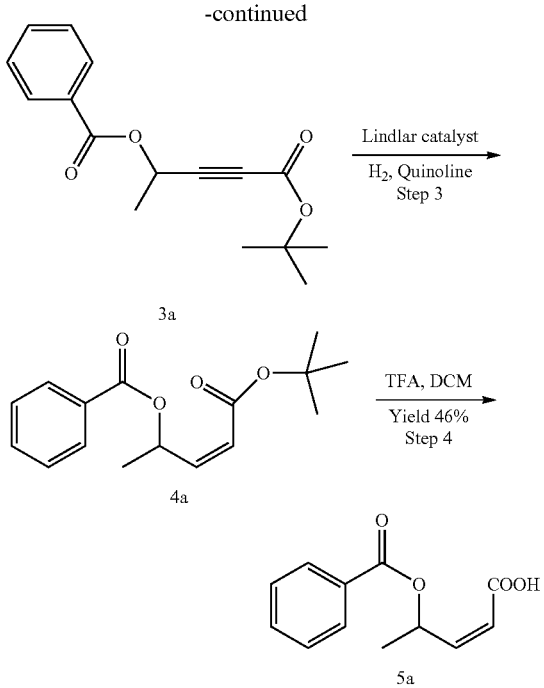

Step 1. tert-Butyl 4-hydroxypent-2-ynoate, Compound 2a

To a solution of tert-butyl propiolate Compound 1a (10 g, 79.28 mmol) in THF (600 mL) was added LDA (2.0 M in THF) (43.6 ml, 87.20 mmol) at −78° C. The reaction mixture was stirred at −78° C. for 50 minutes and then acetaldehyde (4.45 ml, 79.28 mmol) was added dropwise at the same temperature. The reaction mixture stirred at same temperature for 2 h. The progress of the reaction was monitored by TLC (25% EtOAc in petroleum ether, RF=0.2, KMnO$_4$ active) until the starting material was consumed. The reaction mixture quenched with sat. aq. NH$_4$Cl solution (400 ml) and stirred for 20 min. The product was then extracted in diethyl ether (2×400 ml), and dried over anhydrous sodium sulfate. The solvent removed under reduced pressure and the crude product was isolated. The product was purified by column chromatography (100-200 silica gel/eluent 20% EtOAc in petroleum ether) to give Compound 2a (7 g, 52%) as a yellow liquid. $^1$H NMR (400 MHz, DMSO-d$_6$) δ=5.66 (d, J=5.7 Hz, 1H), 4.50 (quin, J=6.4 Hz, 1H), 1.43 (s, 9H), 1.32 (d, J=6.6 Hz, 3H).

Step 2. Synthesis of 5-(tert-butoxy)-5-oxopent-3-yn-2-yl Benzoate, Compound 3a A solution of Compound 2a (2 g, 11.76 mmol) in dry DCM (60 mL) was cooled to −10° C., and then triethyl amine (8.02 ml, 58.82 mmol) and DMAP (143 mg, 1.176 mmol) were added. After 5 minutes, benzoyl chloride (1.36 ml, 11.764 mmol) was added dropwise to the reaction mixture. The reaction mixture was warmed to room temperature over 2 h. The progress of the reaction was monitored by TLC (10% EtOAc in petroleum ether, RF=0.5, UV and KMnO$_4$ active). After completion of the reaction, the reaction mixture was diluted with DCM (200 ml), then washed with water and brine solution (1×60 ml), and dried over anhydrous sodium sulfate. The solvent removed under reduced pressure and purified by column chromatography (100-200 silica gel/eluent 6% EtOAc in petroleum ether) to give Compound 3a (1.35 g, 42%) as a yellow gummy liquid. $^1$H NMR (400 MHz, DMSO-d$_6$) δ=7.99 (d, J=7.5 Hz, 2H), 7.74-7.67 (m, 1H), 7.60-7.53 (m, 2H), 5.76 (q, J=6.7 Hz, 1H), 1.62 (d, J=6.8 Hz, 3H), 1.44 (s, 9H).

Step 3. 5-(tert-butoxy)-5-oxopent-3-en-2-yl Benzoate, Compound 4a

To a solution of Compound 3a (1 g, 3.64 mmol) in EtOAC:hexane (30 ml+10 mL) was added quinoline (0.4 ml) and iUndlar catalyst (496 mg, 4.67 mmol) under argon purging. After 5 minutes of purging, the reaction mixture was stirred under hydrogen balloon pressure for 3 h. The progress of the reaction was monitored by TLC (5% EtOAc in petroleum ether, RF=0.3, UV and KMnO$_4$ active). After completion of reaction, the reaction mixture filtered through celite, the filtrate concentrated under vacuum, and the crude product isolated. The crude product was purified by column chromatography (100-200 silica gel, eluent 12% EtOAc in petroleum ether) and concentrated and dried under vacuum to give Compound 4a (600 mg, 60%) as a yellow liquid. $^1$H NMR (400 MHz, DMSO-d$_6$) δ=7.97 (d, J=7.5 Hz, 2H), 7.70-7.63 (m, 1H), 7.57-7.49 (m, 2H), 6.39-6.27 (m, 2H), 5.79 (d, J=10.3 Hz, 1H), 1.50-1.38 (m, 12H).

Step 4. (Z)-4-(benzoyloxy)pent-2-enoic acid, Compound 5a

A stirred solution of Compound 4a (600 mg, 2.173 mmol) in dry DCM (20 mL) was cooled to −10° C. and trifluoroacetic acid (2.4 ml) was added dropwise to the reaction mixture. The reaction mixture was allowed to warm to 25° C. and stirred for 3 h. The progress of the reaction was monitored by TLC (30% EtOAc in petroleum ether, RF=0.15, UV and KMnO$_4$ active) until the starting material was consumed. After completion of reaction, the crude product was washed with 50% diethyl ether in n-pentane (2×10 ml) and dried under vacuum to give Compound 5a (220 mg, 46%) as an off-white solid. $^1$H NMR (400 MHz, DMSO-d$_6$) δ=12.64 (br s, 1H), 7.97 (d, J=7.5 Hz, 2H), 7.70-7.64 (m, 1H), 7.57-7.50 (m, 2H), 6.44-6.32 (m, 2H), 5.84 (d, J=10.7 Hz, 1H), 1.43 (d, J=6.1 Hz, 3H); D$_2$O (400 MHz, DMSO-d$_6$) δ=8.01-7.94 (m, 2H), 7.70-7.63 (m, 1H), 7.58-7.51 (m, 2H), 6.44-6.34 (m, 2H), 5.89-5.83 (m, 1H), 1.44 (d, J=6.1 Hz, 3H); LCMS: 95.41% (221.23, M+H), RT=2.08 min.

Part B:

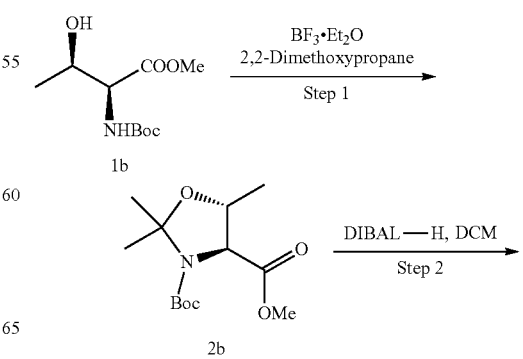

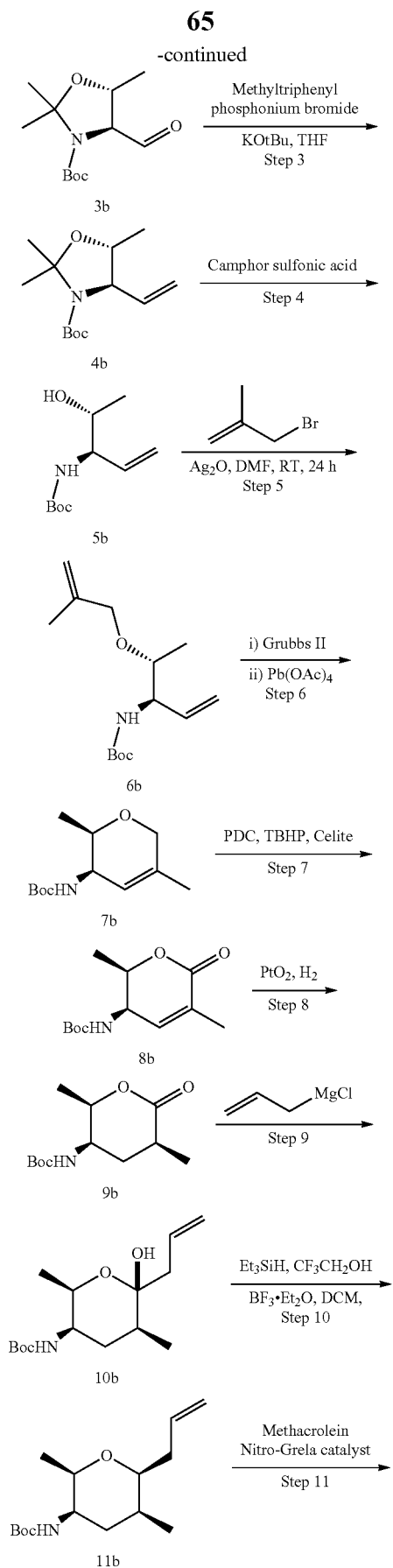

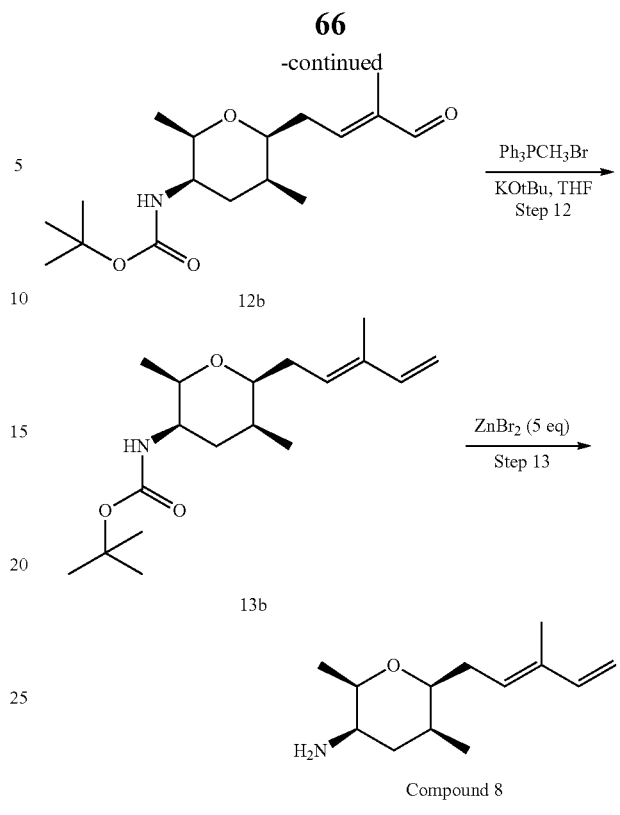

Compound 8

Step 1. (4S, 5R)-3-tert-butyl 4-methyl 2, 2, 5-trimethyloxazolidine-3,4-dicarboxylate, Compound 2b 2,2-Dimethoxypropane (159.1 mL, 1285 mmol) was added to a stirred solution of Compound 1b (150 g, 642 mmol) in DCM (1500 mL) at 23° C., and boron trifluoride diethyl etherate (3.96 mL, 32.13 mmol) was added. The reaction mixture was then stirred at 23° C. for 30 min. The progress of the reaction was monitored by TLC (50% EtOAc in hexane; $R_f$; 0.6, PMA visible). After completion of the reaction, the mixture was quenched with brine (1000 ml). The organic layer was separated, dried over anhydrous sodium sulfate, filtered and concentrated in vacuo to obtain the crude product. The crude residue was purified by flash chromatography (1 to 5% EtOAc in hexanes) on silica (100-200 mesh) to afford Compound 2b (145 g, 82.85%) as a colorless oil. $^1$H NMR (400 MHz, chloroform-d) δ:1.36-1.42 (m, 9H) 1.48 (s, 3H) 1.54-1.67 (m, 6H) 3.76 (s, 3H) 3.86-4.02 (m, 1H) 4.07-4.19 (m, 1H).

Step 2. (4S, 5R)-tert-butyl 4-formyl-2,2,5-trimethyloxazolidine-3-carboxylate, Compound 3b To a stirred solution of Compound 2b (130 g, 475.6 mmol) in dry toluene (750 ml) at −78° C. was added DIBAL-H (1 min toluene) (713 ml, 713 mmol). After the addition, the mixture was stirred at −78° C. for another 10 min and quenched by slow addition of cold MeOH (220 ml) at −78° C. The resulting white emulsion was poured into ice-cold 1N HCl (2000 ml) with stirring over 15 min and the aqueous mixture was then extracted with EtOAc (1000 ml×2), dried over anhydrous sodium sulfate, filtered and concentrated in vacuo to obtain the crude product. The crude residue was purified by flash chromatography (1 to 5%

EtOAc in hexanes) on silica (100-200 mesh) to afford Compound 3b (100 g, 86.95%) as a colorless oil. $^1$H NMR (400 MHz, choloroform-d) δ: 1.36 (d, J=6.10 Hz, 3H) 1.40-1.52 (m, 9H) 1.57-1.72 (m, 6H) 3.67-3.84 (m, 1H) 4.02-4.10 (m, 1H) 9.36-9.47 (m, 1H).

Step 3. (4R, 5R)-tert-Butyl 2, 2, 5-trimethyl-4-vinyloxazolidine-3-carboxylate, Compound 4b To a solution of methyltriphenylphosphonium bromide (293 g, 822 mmol) in THF (750 ml) at 0° C. was added KOtBu (92 g, 822 mmol) in one portion. The resulting mixture was stirred for one hour at the same temperature, after which Compound 3b (100 g, 411 mmol) in THF (250 ml) was added and the mixture was stirred at 50° C. for 12 h. The progress of the reaction was monitored by TLC (10% EtOAc in hexane, $R_f$: 0.5, PMA visible). After cooling to 23° C., the reaction mixture was quenched with saturated NH$_4$Cl solution (1000 ml), extracted with EtOAc (1000 ml×2). The combined organic layers were washed with brine (1000 ml), dried over anhydrous sodium sulfate, filtered and concentrated in vacuo to obtain the crude compound. The crude residue was purified by flash chromatography (1 to 5% EtOAc in hexanes) on silica (100-200 mesh) to afford Compound 4b (80 g, 80.80%) as a colorless oil. $^1$H NMR (400 MHz, chloroform-d) δ ppm 1.28 (d, J=5.99 Hz, 3H) 1.38-1.49 (m, 9H) 1.51 (s, 3H) 1.56-1.63 (m, 3H) 3.72 (br d, J=1.31 Hz, 1H) 3.78-3.86 (m, 1H) 5.16 (br d, J=7.85 Hz, 2H) 5.66 (br d, J=6.43 Hz, 1H).

Step 4. tert-Butyl (3R, 4R)-4-hydroxypent-1-en-3-ylcarbamate, Compound 5b

To stirred solution of Compound 4b (80 g, 331.4 mmol) in MeOH (2.0 l) at 23° C., was added camphor sulfonic acid (7.7 g, 33.14 mmol). The reaction mixture was stirred at 23° C. for 48 h. The progress of the reaction was monitored by TLC (40% EtOAc in hexane, $R_f$: 0.25, PMA visible). After completion, the reaction mixture was quenched with saturated NaHCO$_3$ solution (1000 ml) and most of the solvent was removed in vacuo. The aqueous residue was extracted with EtOAc (1000 ml×2). The combined organic layers were washed with brine (1000 ml), dried over anhydrous sodium sulfate, filtered and concentrated in vacuo to obtain the crude compound. The crude residue was purified by flash chromatography (10→40% EtOAc in hexanes) on silica (100-200 mesh) to afford Compound 5b (58 g, 86.95%) as a colorless oil. $^1$H NMR (400 MHz, chloroform-d) δ ppm 1.23 (d, J=6.32 Hz, 3H) 1.46 (s, 9H) 1.94 (br s, 1H) 3.87 (br dd, J=5.99, 3.05 Hz, 1H) 4.02-4.12 (m, 1H) 4.87 (br s, 1H) 5.21-5.26 (m, 1H) 5.28-5.31 (m, 1H) 5.84 (ddd, J=17.19, 10.49, 5.12 Hz, 1H); LCMS: 94.36% (202.14, M+H), RT: 1.50 min.

Step 5. tert-Butyl (3R, 4R)-4-(2-methylallyloxy) pent-1-en-3-ylcarbamate, Compound 6b To stirred solution of Compound 5b (40 g, 198.73 mmol) in DMF (250 ml) at 23° C., was added methallyl bromide (107.3 g, 795.9 mmol). The flask was wrapped with aluminum foil and silver oxide (69 g, 298 mmol) was added. The reaction mixture was stirred at 23° C. for 24 h. The progress of the reaction was monitored by TLC (10% EtOAc in hexane, $R_1$: 0.4, PMA visible). After 24 h at 23° C., the reaction mixture was diluted with ether (500 ml), filtered through celite and washed with additional ether (500 ml). The filtrate was then extracted with water (5×500 ml), brine (50 ml), dried over anhydrous Na$_2$SO$_4$, filtered and concentrated in vacuo. The crude residue was purified by flash chromatography (2.5→10% EtOAc in hexanes) on silica (100-200 mesh) to afford Compound 6b (40.5 g, 79.88%) as a colorless oil. $^1$H NMR (400 MHz, chloroform-d) δ ppm 1.16 (d, J=6.32 Hz, 3H) 1.45 (s, 9H) 1.68-1.77 (m, 3H) 3.51-3.63 (m, 1H) 3.75-3.86 (m, 1H) 3.89-4.01 (m, 1H) 4.12 (br d, J=7.08 Hz, 1H) 4.79-4.91 (m, 2H) 4.94 (d, J=0.87 Hz, 1H) 5.09-5.25 (m, 2H) 5.89 (ddd, J=17.22, 10.46, 5.45 Hz, 1H); LCMS: 78.48% (256.33, M+H), RT: 2.69 min.

Step 6. tert-Butyl ((2R, 3R)-2,5-dimethyl-3,6-dihydro-2H-pyran-3-yl)carbamate Compound 7b To a stirred solution of Compound 6b (35 g, 137 mmol) in benzene (500 ml) was added Grubbs-II catalyst (2.3 g, 2.74 mmol) at 23° C. under a nitrogen atmosphere. The reaction was then refluxed for 3 h. After cooling to 23° C., lead tetra acetate (1.8 g, 4.11 mmol) was added and stirred for an additional 12 h at 23° C. The reaction was monitored by TLC (10% EtOAc in hexane, $R_F$=0.3, PMA visible). The solvent was then removed in vacuo and the crude residue was purified by flash chromatography (2.5→10% EtOAc in hexanes) on silica (100-200 mesh) to afford Compound 7b (26 g, 83.60%) as a white solid. $^1$H NMR (400 MHz, chloroform-d) δ ppm 1.16-1.22 (m, 3H) 1.44 (s, 9H) 1.61 (s, 3H) 3.57-3.66 (m, 1H) 3.86-3.94 (m, 1H) 3.97 (s, 1H) 3.98-4.06 (m, 1H) 4.60 (br d, J=9.66 Hz, 1H) 5.56-5.62 (m, 1H); LCMS: 94.00% (228.29, M+H), RT: 2.35 min.

Step 7. tert-Butyl ((2R,3R)-2,5-dimethyl-6-oxo-3,6-dihydro-2H-pyran-3-yl)carbamate, Compound 8b To a stirred solution of Compound 7b (30 g, 132.1 mmol) in benzene (1200 ml) at 23° C. was added celite (120 g), pyridinium dichromate (99.3 g, 364.3 mmol) and tert-butyl hydroperoxide (70 wt % in water, 47.5 ml, 528.6 mmol). After 5 h at 23° C., the reaction mixture was filtered through celite, washed with ethyl acetate (500 ml), dried over anhydrous Na$_2$SO$_4$, filtered and concentrated in vacuo. The crude residue was purified by flash chromatography (7.5→30% EtOAc in hexanes) on silica gel (100-200 mesh) to afford Compound 8b (18 g, 56.60%) as a white solid. $^1$H NMR (400 MHz, chloroform-d) δ ppm 1.38 (d, J=6.44 Hz, 3H) 1.42-1.49 (m, 9H) 1.92-1.97 (m, 3H) 4.21-4.31 (m, 1H) 4.51-4.65 (m, 2H) 6.63 (dd, J=6.32, 1.43 Hz, 1H); LCMS: 96.91% (242.17, M+H), RT: 1.68 min.

Step 8. tert-Butyl ((2R, 3R, 5S)-2,5-dimethyl-6-oxotetrahydro-2H-pyran-3-yl)carbamate, Compound 9b To a stirred solution of Compound 8b (25 g, 103.61 mmol) in ethanol (500 ml) at 23° C. was added PtO$_2$ (470 mg, 2.07 mmol) and the atmosphere in the reaction flask was changed to hydrogen. The reaction mixture was stirred at 23° C. for 24 h with monitoring by TLC (30% EtOAc in hexane, $R_F$=0.35, PMA visible). After 24 h at 23° C., the reaction mixture was filtered through filter paper and the solvent was removed in vacuo to afford Compound 9b (25 g, 99%) as a white solid. $^1$H NMR (400 MHz, chloroform-d) δ ppm 1.16-1.25 (m, 4H) 1.29-1.38 (m, 5H) 1.39-1.54 (m, 12H) 2.49-2.71 (m, 2H) 4.03-4.19 (m, 1H) 4.41-4.55 (m, 1H) 4.64-4.82 (m, 1H).

Step 9. tert-Butyl ((2R, 3R, 5S)-6-allyl-6-hydroxy-2,5-dimethyltetrahydro-2H-pyran-3-yl)carbamate, Compound 10b To a stirred solution of Compound 9b (25 g, 102.7 mmol) in THF (300 ml) at −78° C. was added allyl magnesium chloride (1.4 M solution in THF, 146 ml, 205.4 mmol) down the flask sides under a nitrogen atmosphere. After 1.5 h at the same temperature, the reaction was quenched with saturated aqueous $NH_4Cl$ (500 ml). The aqueous residue was extracted with EtOAc (2×500 ml). The combined organic layers were washed with brine (500 ml), dried over anhydrous $Na_2SO_4$, filtered and concentrated in vacuo. The crude residue was purified by flash chromatography (10-, 50% EtOAc in hexanes) on silica (100-200 mesh) to afford Compound 10b (20 g, 68.25%) as a pale yellow oil. $^1H$ NMR (400 MHz, chloroform-d) δ ppm 1.13 (d, J=7.2 Hz, 3H) 1.16 (d, J=6.3 Hz, 3H) 1.45 (s, 9H) 1.93-2.03 (m, 1H) 2.10-2.29 (m, 1H) 2.68-2.80 (m, 1H) 3.24-3.39 (m, 2H) 3.65-3.76 (m, 1H) 4.71 (br d, J=9.06 Hz, 1H) 5.05-5.22 (m, 2H) 5.78-6.02 (m, 1H).

Step 10. tert-Butyl ((2R, 3R, 5S, 6S)-6-allyl-2,5-dimethyltetrahydro-2H-pyran-3-yl)carbamate, Compound 11b To a stirred solution of Compound 10b (5 g, 17.54 mmol) in DCM (50 ml) was added 2,2,2-trifluoroethanol (10 ml, 140.3 mmol) and triethylsilane (28 ml, 175.4 mmol) at 23° C. under a nitrogen atmosphere. The reaction was cooled to −78° C. and $BF_3.OEt_2$ complex (8.6 ml, 70.16 mmol) was added slowly down the flask side. After an additional 3 h at the same temperature, saturated aqueous $NaHCO_3$ (100 ml) was added at −78° C., and the layers were separated. The aqueous residue was extracted with EtOAc (3×50 ml). The combined organic layers were washed with brine (100 ml), dried over anhydrous $Na_2SO_4$, filtered, and concentrated under reduced pressure. The resulting residue was purified by flash chromatography (2-. 12.5% EtOAc in hexanes) on silica gel (100-200 mesh) to afford Compound 11b (1.8 g, 38.29%) as colorless oil. $^1H$ NMR (400 MHz, chloroform-d) δ ppm 0.98-1.07 (m, 3H) 1.10-1.21 (m, 3H) 1.45 (d, J=1.43 Hz, 9H) 1.68-1.81 (m, 1H) 1.95 (br d, J=2.74 Hz, 2H) 2.03-2.20 (m, 1H) 2.24-2.41 (m, 1H) 3.37-3.68 (m, 3H) 4.78 (br d, J=9.06 Hz, 1H) 4.98-5.15 (m, 2H) 5.71-5.88 (m, 1H); LCMS: 60.33% (270.33, M+H), RT: 2.74 min.

Step 11. tert-Butyl ((2R, 3R, 5S, 6S)-2,5-dimethyl-6-((E)-3-methyl-4-oxobut-2-en-1-yl)tetrahydro-2H-pyran-3-yl)carbamate, Compound 12b To a stirred solution of Compound 11b (3.6 g, 13.36 mmol) in DCM (50 ml) at 23° C. was added methacrolein (22 ml, 267.2 mmol) followed by Nitro-Grela catalyst (897 mg, 1.336 mmol), under a nitrogen atmosphere. After 12 h at 23° C., the solvent was removed in vacuo. The crude residue was purified by flash chromatography (10→25% EtOAc in hexanes) on silica (100-200 mesh) to afford Compound 12b (2.2 g, 52.88%) as a pale yellow oil. $^1H$ NMR (400 MHz, chloroform-d) δ ppm 1.07 (d, J=7.34 Hz, 3H) 1.16 (d, J=6.36 Hz, 3H) 1.45 (s, 9H) 1.76 (s, 3H) 1.85-1.99 (m, 2H) 2.34-2.45 (m, 1H) 2.56 (dt, J=15.41, 7.46 Hz, 1H) 3.53-3.68 (m, 3H) 4.73 (br d, J=9.29 Hz, 1H) 6.50-6.57 (m, 1H) 9.42 (s, 1H); LCMS: 86.69% (312.31, M+H), RT: 2.52 min.

Step 12. tert-Butyl ((2R, 3R, 5S, 6S)-2,5-dimethyl-6-((E)-3-methylpenta-2,4-dien-1-yl)tetrahydro-2H-pyran-3-yl)carbamate, Compound 13b To a stirred suspension of methyl triphenyl phosphonium bromide (3.7 g, 10.59 mmol) in THF (25 ml) at 0° C. was added KOtBu (1.1 g, 9.88 mmol) under a nitrogen atmosphere. After 30 min, Compound 12b (2.2 g, 7.064 mmol) in THF (15 ml) was added dropwise by cannula at the same temperature and rinsed with additional THF (5 ml). After 2 h at 23° C., the reaction was quenched with saturated aqueous $NH_4Cl$ (50 ml) and most of the solvent was removed in vacuo. The aqueous residue was extracted with EtOAc (2×30 ml). The combined organic layers were washed with brine (50 ml), dried over anhydrous $Na_2SO_4$, filtered and concentrated in vacuo. The crude residue was purified by flash chromatography (1→10% EtOAc in hexanes) on silica (100-200 mesh) to give Compound 13b (1.5 g, 68.80%) as a colorless oil. $^1H$ NMR (400 MHz, chloroform-d) δ ppm 1.03 (d, J=7.41 Hz, 3H) 1.15 (d, J=6.32 Hz, 3H) 1.44 (s, 9H) 1.72-1.80 (m, 3H) 1.84-1.97 (m, 2H) 2.19-2.30 (m, 1H) 2.33-2.44 (m, 1H) 3.51 (td, p7.28, 2.67 Hz, 1H) 3.54-3.66 (m, 2H) 4.69-4.81 (m, 1H) 4.95 (d, J=10.68 Hz, 1H) 5.11 (d, J=17.44 Hz, 1H) 5.46 (t, J=6.98 Hz, 1H) 6.37 (dd, J=17.38, 10.74 Hz, 1H); LCMS: 94.58% (310.37, M+H), RT: 2.96 min.

Step 13. (2R, 3R, 5S, 6S)-2,5-dimethyl-6-((E)-3-methylpenta-2,4-dien-1-yl)tetrahydro-2H-pyran-3-amine, Compound 8

To a stirred suspension of Compound 13b (1.5 g, 4.84 mmol) in DCM (40 ml) at 23° C. was added zinc bromide (5.45 g, 24.23 mmol) under a nitrogen atmosphere. The reaction mixture was stirred at 23° C. for 48 h. The progress of the reaction was monitored by TLC (10% MeOH in DCM, $R_F$=0.1, UV visible). After completion, the reaction mixture was diluted with DCM (50 ml), filtered, washed with DCM (100 ml), the filtrate was concentrated in vacuo to afford Compound 8 (1.6 g crude) as a pale yellow gum. It was directly used in the next step without further purification. $^1H$ NMR (400 MHz, chloroform-d) δ ppm 1.03-1.20 (m, 3H) 1.23-1.32 (m, 3H) 1.34-1.43 (m, 3H) 1.73-1.81 (m, 3H) 1.88-2.00 (m, 1H) 2.09-2.54 (m, 3H) 3.42-3.53 (m, 1H) 3.58 (br d, J=5.87 Hz, 1H) 3.66-3.89 (m, 2H) 4.87-5.04 (m, 1H) 5.08-5.21 (m, 1H) 5.36-5.53 (m, 1H) 6.19-6.46 (m, 1H) 6.70-7.12 (m, 3H); LCMS: 81.62% (210.18, M+H), RT: 1.80 min.

Part C:

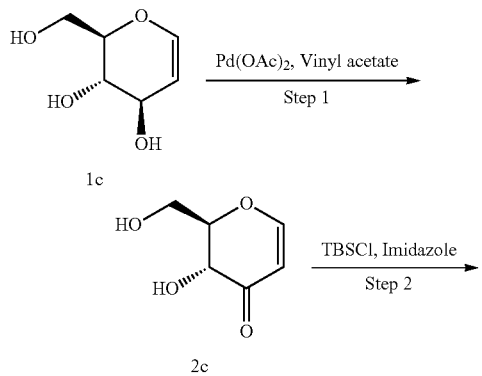

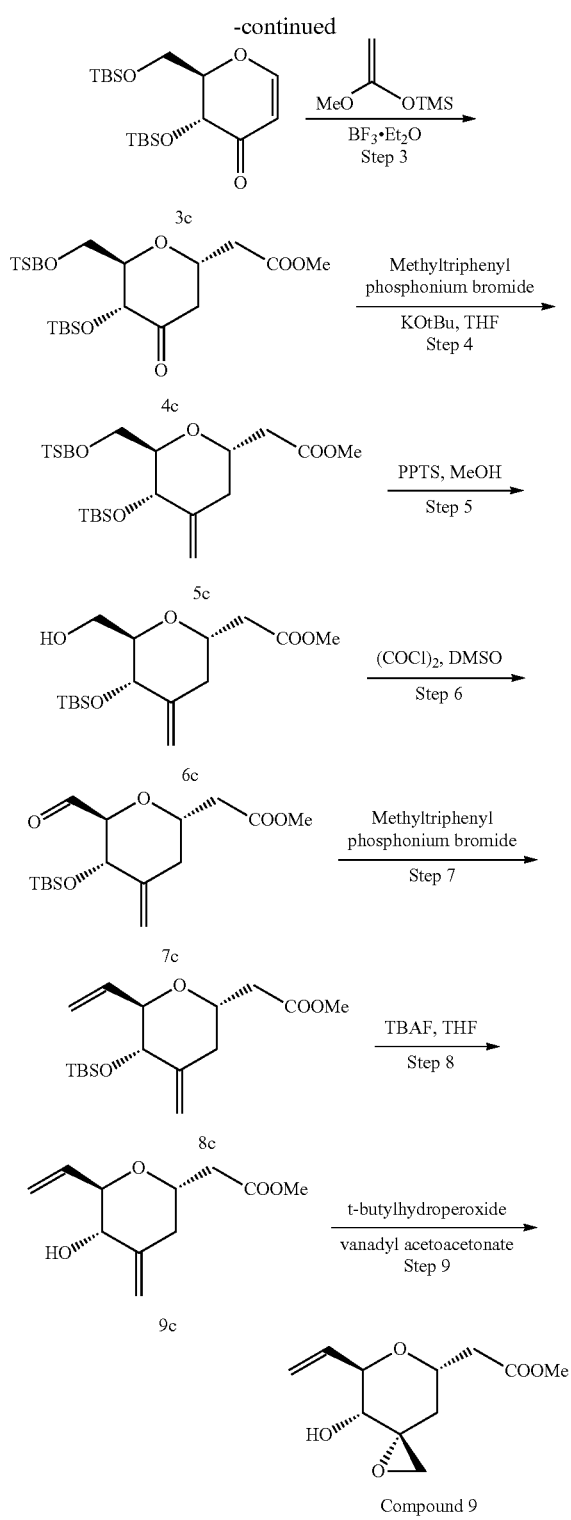

(100 ml). The solvent was concentrated under reduced pressure to obtain the crude product. The residue was recrystallized from a mixture of acetone (68 ml) and EtOAc (68 ml) to afford Compound 2c (75 g, 55%) as an off-white solid. $^1$H NMR (400 MHz, DMSO-d$_6$) δ=7.60 (d, J=5.9 Hz, 1H), 5.61 (d, J=4.9 Hz, 1H), 5.30 (d, J=5.4 Hz, 1H), 5.00 (t, J=5.6 Hz, 1H), 4.16-4.06 (m, 2H), 3.82-3.76 (m, 1H), 3.73-3.66 (m, 1H).

Step 2. (2R, 3R)-3-(tert-Butyldimethylsilyloxy)-2-((tert-butyldimethylsilyloxy) methyl)-2H-pyran-4 (3H)-one, Compound 3c To a solution of Compound 2c (100 g, 0.69 mol) in DMF (1900 ml) was added TBS-Cl (277 g, 2.65 mol) and imidazole (140.9 g, 2.07 mol) at room temperature. The reaction mixture was stirred at room temperature for 24 h. The progress of the reaction was monitored by TLC (5% EtOAc in petroleum ether, Rf:0.5, UV active). After completion of reaction, the reaction mixture was diluted with diethyl ether (2500 ml) and washed with water (1000 ml) and brine (1000 ml). The diethyl ether layer was dried over anhydrous sodium sulfate, then filtered, and concentrated to obtain the crude product. The crude product was purified by column chromatography (100-200 silica gel/eluent 2% EtOAc in petroleum ether) to afford Compound 3c (200 g, 77.5%) as an off white solid. $^1$H NMR (400 MHz, chloroform-d) δ=7.30-7.25 (m, 1H), 5.30 (d, J=5.8 Hz, 1H), 4.45-4.40 (m, 1H), 4.18 (td, J=2.6, 12.2 Hz, 1H), 3.99 (d, J=2.8 Hz, 2H), 0.91 (d, J=2.5 Hz, 18H), 0.23 (s, 3H), 0.11-0.05 (m, 6H); LCMS: 99.48% (373.37, M+H), RT: 3.47 min.

Step 3. Methyl 2-((2S, 5R, 6R)-5-(tert-butyldimethylsilyloxy)-6-((tert-butyldimethylsilyloxy)methyl)-4-oxotetrahydro-2H-pyran-2-yl)acetate, Compound 4c To a stirred solution of Compound 3c (55 g, 0.147 mol) in DCM (2000 ml) was added tert-butyl(1-methoxyvinyloxy)dimethylsilane (55 g, 0.292 mol) at room temperature. The reaction mixture was stirred at room temperature for 2 h, followed by addition of BF$_3$.Et$_2$O (63.25 g, 3.03 mol) at −78° C. The reaction mixture was stirred at −78° C. for 1 h. The progress of the reaction was monitored by TLC (15% EtOAc in petroleum ether, Rf: 0.5, PMA active). The reaction mixture was quenched with saturated NH$_4$Cl (500 ml) and extracted with DCM (2×250 ml). The combined organic layer was washed with saturated NaHCO$_3$ (500 ml) and brine (500 ml). The organic layer was dried over anhydrous sodium sulfate, then filtered and concentrated to obtain the crude product. The crude product was purified by column chromatography (100-200 silica gel/eluent 3% EtOAc in petroleum ether) to give Compound 4c (25 g, 37.9%) as a transparent gum. $^1$H NMR (400 MHz, chloroform-d) b=4.92-4.72 (m, 1H), 4.33 (d, J=8.8 Hz, 1H), 3.91-3.78 (m, 2H), 3.74-3.58 (m, 4H), 2.83-2.60 (m, 2H), 2.52-2.38 (m, 2H), 0.99-0.79 (m, 18H), 0.15 (s, 3H), 0.11-0.01 (m, 9H).

Step 4. Methyl 2-((2S, 5S, 6R)-5-(tert-butyldimethylsilyloxy)-6-((tert-butyldimethylsilyloxy)methyl)-4-methylenetetrahydro-2H-pyran-2-yl)acetate, Compound 5c To a suspension of methyl triphenyl phosphonium bromide (12 g, 0.033 mol) in THF (180 ml) at 0° C., was added a THF (80 ml) solution of KOtBu (3.33 g, 0.029 mol). After 1 h, a THF (60 ml) solution of Compound 4c (10 g, 0.022

Step 1. Synthesis of (2R, 3R)-3-hydroxy-2-(hydroxymethyl)-2H-pyran-4 (3H)-one, Compound 2c To a mixture of Compound 1c (137.5 g, 0.941 mole), Pd(OAc)$_2$ (5.9 g, 0.026 mole) in ACN (550 ml) was added vinyl acetate (250 g, 2.907 mole) at room temperature. The reaction mixture was stirred at 60° C. for 24 h. The reaction mixture was filtered through celite and washed with EtOAc mole) was added dropwise. Then reaction mixture allowed to 25° C. and stirred for 1 hr. The progress of the reaction was monitored by TLC (5% EtOAc in petroleum ether, RF=0.3, PMA active). The reaction mixture was quenched with saturated NH$_4$Cl (100 ml) and extracted with EtOAc (2×150 ml). The EtOAc layer was dried over anhydrous sodium sulfate, then filtered and concentrated. The crude residue was purified by column chromatography (100-200 silica gel/eluent 5% EtOAc in petroleum ether) to afford Compound 5c (4 g, 40.4%) as a yellow liquid. $^1$H NMR (400 MHz, chloroform-d) δ=5.07 (s, 1H), 4.89-4.86 (m, 1H), 4.30-4.23 (m, 1H), 4.02 (d, J=6.5 Hz, 1H), 3.75-3.66 (m, 5H), 3.47 (td, J=4.7, 6.4 Hz, 1H), 2.65 (dd, J=7.3, 15.0 Hz, 1H), 2.48 (dd, J=6.8, 15.0 Hz, 1H), 2.42-2.28 (m, 2H), 0.95-0.84 (m, 18H), 0.12-0.01 (m, 12H).

Step 5. Methyl-2-((2S, 5S, 6R)-5-(tert-butyldimethylsilyloxy)-6-(hydroxymethyl)-4-methylenetetrahydro-2H-pyran-2-yl)acetate, Compound 6c To a stirred solution of Compound 5c (75.1 g, 0.168 mole) in MeOH (751 ml) was added PPTS (59.4 g, 0.236 mole) at room temperature. The reaction mixture was stirred at room temperature for 16 h. The progress of the reaction was monitored by TLC (25% EtOAc in petroleum ether, RF=0.3, PMA active). The reaction mixture was quenched with saturated NaHCO$_3$ (1270 ml) and extracted with EtOAc (2×1500 ml). The EtOAc layer was dried over anhydrous sodium sulfate, then filtered and concentrated. The crude residue was purified by column chromatography (100-200 silica gel/eluent 25% EtOAc in petroleum ether) to afford Compound 6c (39 g, 69.8%) as a yellow colored gum. $^1$H NMR (400 MHz, chloroform-d) δ=5.11 (s, 1H), 4.88 (s, 1H), 4.42-4.35 (m, 1H), 3.93 (d, J=7.3 Hz, 1H), 3.71-3.64 (m, 5H), 3.56-3.50 (m, 1H), 2.73 (dd, J=8.8, 15.4 Hz, 1H), 2.51-2.42 (m, 2H), 2.31 (dd, J=3.8, 13.4 Hz, 1H), 2.15 (t, J=6.4 Hz, 1H), 0.94-0.91 (m, 9H), 0.10-0.08 (m, 3H), 0.05-0.03 (m, 3H); LCMS: 80.17% (331.39, M+H), RT: 2.78 min.

Step 6. Methyl 2-((2S, 5S, 6S)-5-(tert-butyldimethylsilyloxy)-6-formyl-4-methylenetetrahydro-2H-pyran-2-yl) acetate, Compound 7c To a stirred solution of oxallyl chloride (17.2 g, 0.136 mol) in DCM (214 ml) at −78° C. was slowly added DMSO (21 g, 0.27 mol). The reaction mixture was stirred at −78° C. to −60° C. for 20 min. A solution of Compound 6c (30 g, 0.09 mol) in DCM (414 ml) was added dropwise at −78° C. for 30 min. The reaction mixture was slowly warmed to −45° C. over 30 min. TEA (52.8 g, 0.522 mol) was added at −45° C. and the reaction mixture was warmed to 0° C. over 10 min. The reaction progress was monitored by TLC (20% EtOAc in petroleum ether, RF=0.35, PMA active). The reaction mixture was quenched with saturated NH$_4$Cl (500 ml) and extracted with DCM (2×500 ML). The organic layer was washed with brine (1000 ml). The organic layer was dried over anhydrous sodium sulfate, then filtered and concentrated. The crude residue was purified by column chromatography (100-200 silica gel/eluent 20% EtOAc in petroleum ether) to give Compound 7c (22 g, 73.8%) as a yellow gum. $^1$H NMR (400 MHz, chloroform-d) δ=9.76-9.73 (m, 1H), 5.05-5.00 (m, 1H), 4.93-4.87 (m, 1H), 4.36 (d, J=4.3 Hz, 1H), 4.29-4.20 (m, 1H), 4.12-4.08 (m, 1H), 3.73-3.67 (m, 4H), 2.78-2.69 (m, 1H), 2.55-2.40 (m, 1H), 2.27-2.20 (m, 2H), 0.96-0.87 (m, 9H), 0.12-0.02 (m, 6H); LCMS: 97.53% (329.34, M+H), RT: 2.60 min.

Step 7: Methyl 2-((2S, 5S, 6R)-5-(tert-butyldimethylsilyloxy)-4-methylene-6-vinyltetrahydro-2H-pyran-2-yl)acetate, Compound 8c To a suspension of methyl triphenyl phosphonium bromide (28 g, 0.078 mol) in THF (381 ml) at 0° C. was added KOtBu (7.9 g, 0.070 mol). After 1 h, a THF (1361 ml) solution of Compound 7c (14 g, 0.042 mole) was added dropwise. The mixture was stirred for 1 h at 0° C. The reaction progress was monitored by TLC (10% EtOAc in petroleum ether, RF=0.5, PMA active). The reaction mixture was quenched with saturated NH$_4$Cl (1200 ml) and extracted with EtOAc (2×500 ml). The EtOAc layer was washed with brine (1000 ml), dried over anhydrous sodium sulfate, filtered and concentrated. The crude residue was purified by column chromatography (100-200 silica gel/eluent 2% EtOAc in petroleum ether) to give Compound 8c (5.8 g, 41.7%) as a transparent gum. $^1$H NMR (400 MHz, chloroform-d) δ ppm 0.04 (d, J=7.08 Hz, 6H) 0.88-0.95 (m, 9H) 2.30-2.39 (m, 1H) 2.40-2.57 (m, 2H) 2.70 (dd, J=14.99, 7.47 Hz, 1H) 3.62-3.71 (m, 3H) 3.83 (d, J=6.65 Hz, 1H) 3.90-3.99 (m, 1H) 4.37 (tt, J=6.96, 4.81 Hz, 1H) 4.88 (d, J=0.65 Hz, 1H) 5.09 (s, 1H) 5.18-5.37 (m, 2H) 5.83 (ddd, J=17.17, 10.74, 6.10 Hz, 1H).

Step 8. Methyl 2-((2S, 5S, 6R)-5-hydroxy-4-methylene-6-vinyltetrahydro-2H-pyran-2-yl)acetate, Compound 9c To a stirred solution of Compound 8c (5.6 g, 0.017 mole) in THF (52 ml) was added TBAF (5.15 g, 0.019 mole, 1M in THF) at 0° C. The reaction mixture was stirred at RT for 8 h. The reaction progress was monitored by TLC (30% EtOAc in petroleum ether, RF=0.2, PMA active). The reaction mixture was quenched with saturated NH4Cl (100 ml) and extracted with EtOAc (2×300 ml). The organic layer was washed with brine (600 ml), dried over anhydrous sodium sulfate, filtered and concentrated. The crude product was purified by column chromatography (100-200 silica gel/eluent 20% EtOAc in petroleum ether) to give Compound 9c (2.5 g, 68.8%) as a yellow gum. $^1$H NMR (400 MHz, chloroform-d) δ ppm 1.97-2.08 (m, 1H) 2.33-2.55 (m, 3H) 2.68 (dd, J=15.13, 7.67 Hz, 1H) 3.69 (s, 3H) 3.93 (t, J=5.48 Hz, 1H) 4.06-4.14 (m, 1H) 4.34 (dt, J=12.44, 6.17 Hz, 1H) 4.95 (s, 1H) 5.12 (s, 1H) 5.26-5.42 (m, 2H) 5.86 (ddd, J=17.26, 10.80, 6.14 Hz, 1H).

Step 9. Methyl 2-((3R, 5S, 7R, 8R)-8-hydroxy-7-vinyl-1, 6-dioxaspiro [2.5] octan-5-yl)acetate, Compound 9

Compound 9c (1.1 g, 0.0051 mol) was dissolved in DCM (86 ml) and cooled to −20° C. To this was added vanadyl acetoacetate (125 mg, 0.00047 mol) followed by a solution of tert-butyl hydroperoxide (1.71 ml, 0.017 mol). The mixture was allowed to slowly warm to 0° C. over 2 h. The reaction mixture was stirred at room temperature for 24 h. The reaction progress was monitored by TLC (40% EtOAc in petroleum ether, Rf=0.2, PMA active). The reaction mixture was purified by column chromatography (100-200 silica gel/eluent 35% EtOAc in petroleum ether) to afford Compound 9 (600 mg) as a colorless gum. $^1$H NMR (300 MHz, chloroform-d) δ ppm 1.76-1.93 (m, 2H) 1.99-2.14 (m, 2H) 2.60-2.74 (m, 2H) 2.84-3.02 (m, 2H) 3.43-3.55 (m, 1H 3.70 (s, 3H) 4.17-4.29 (m, 1H) 4.42-4.55 (m, 1H) 5.26-5.45 (m, 2H) 5.93 (ddd, J=17.45, 10.69, 5.48 Hz, 1H).

Part D:

1.48-1.59 (m, 8H) 1.23-1.30 (m, 3H) 1.13-1.20 (m, 4H) 1.01-1.09 (m, 4H) 0.81-0.96 (m, 2H); LCMS: 85.71% (412.37, M+H), RT: 2.92 and 2.94 min.

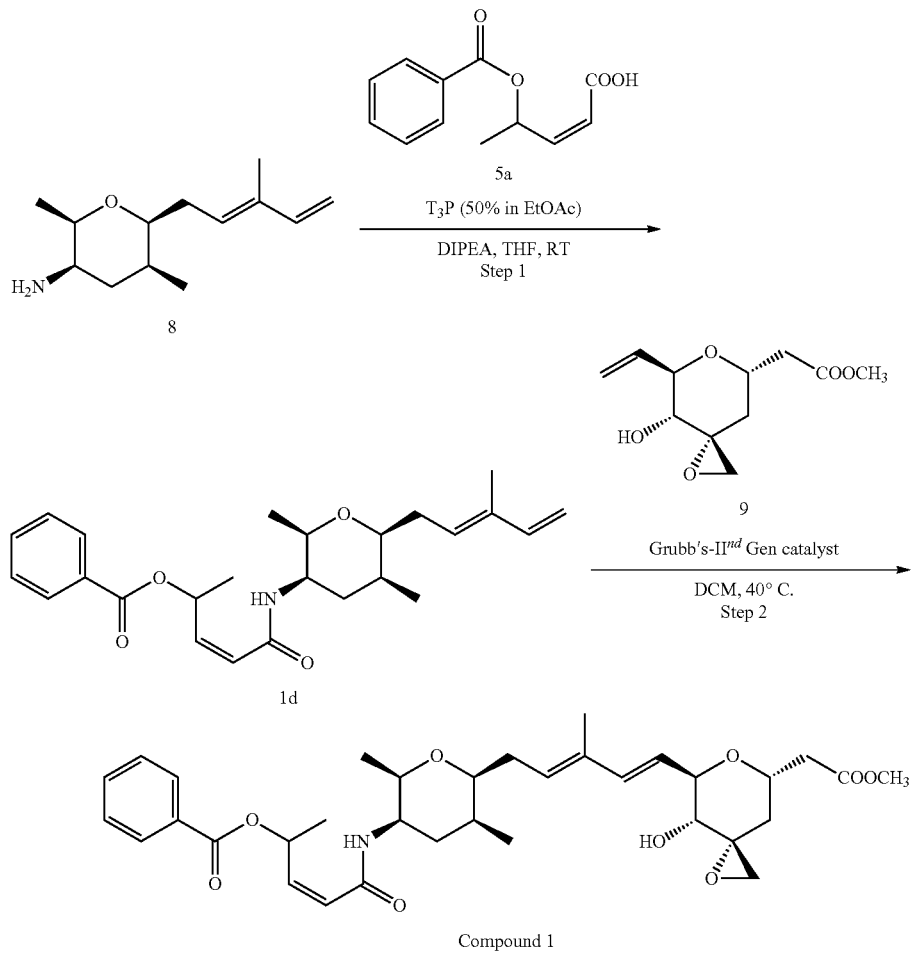

Step 1. (Z)-5-((2R, 3R, 5S, 6S)-2,5-dimethyl-6-((E)-3-methylpenta-2,4-dienyl)tetrahydro-2H-pyran-3-ylamino)-5-oxopent-3-en-2-yl Benzoate, Compound 1d To a stirred solution of Compound 8 (200 mg, 0.955 mmol) and Compound 5a (126 mg, 0.573 mmol) in THF (10 ml), DIPEA (616 mg, 4.755 mmole) and T$_3$P (50% in EtOAc) (911 mg, 2.865 mmol) were added at room temperature. The reaction mixture was stirred at room temperature for 3 h. The reaction progress was monitored by TLC (20% EtOAc in petroleum ether, RF=0.5, UV active) until the starting material was consumed. The reaction solvent was concentrated under reduced pressure to obtain the crude product. The crude product was purified by column chromatography (100-200 silica gel/eluent 12% EtOAc in petroleum ether) to give Compound 1d (120 mg, 30%) as a colorless gum. $^1$H NMR (400 MHz, chloroform-d) δ ppm 8.01-8.11 (m, 2H) 7.50-7.62 (m, 1H) 7.39-7.47 (m, 2H) 6.47-6.57 (m, 1H) 6.26-6.44 (m, 2H) 5.92-6.08 (m, 2H) 5.70-5.80 (m, 1H) 5.39-5.51 (m, 1H) 5.11 (d, J=17.33 Hz, 1H) 4.96 (d, J=10.79 Hz, 1H) 3.92-4.04 (m, 1H) 3.63-3.73 (m, 1H) 3.50-3.58 (m, 1H) 2.41 (dq, J=15.10, 7.61 Hz, 1H) 2.21-2.33 (m, 1H) 1.89-2.02 (m, 3H) 1.72-1.84 (m, 5H)

Step 2. (Z)-5-((2R, 3R, 5S, 6S)-6-((2E, 4E)-5-((3R, 4R, 5R, 7S)-4-hydroxy-7-(2-methoxy-2-oxoethyl)-1,6-dioxaspiro[2.5]octan-5-yl)-3-methylpenta-2,4-dienyl)-2,5-dimethyltetrahydro-2H-pyran-3-ylamino)-5-oxopent-3-en-2-yl Benzoate, Compound 1

To a stirred solution of Compound 1d (115 mg, 0.279 mmol) in DCM (5 mL), Compound 9 (181 mg, 2.83 mmol) and Grubbs-II catalyst (47 mg, 0.055 mmol) were added at room temperature under argon atmosphere. The reaction mixture was stirred at 40° C. for 4 h. The reaction progress was monitored by TLC, which showed that both starting materials were still present. The reaction mixture was filtered through celite and washed with DCM (5 mL). The solvent was concentrated under reduced pressure to a residue. The residue was again dissolved in DCM (5 mL) and Grubbs-II catalyst (47 mg, 0.055 mmol) was added. The reaction mixture was stirred for 23 h at 40° C. The reaction progress was monitored by TLC (50% EtOAc in petroleum ether, RF=0.1, UV active) until Compound 9 was consumed.

The reaction mixture was filtered through a celite and washed with DCM (2 mL). The solvent was concentrated under reduced pressure to obtain crude product. The crude product was purified by preparative HPLC [Mobile Phase A: 10 mm ABC, Mobile Phase B: acetonitrile; Column: X-Bridge (150×19) mm, 5u; Method: (T/o % B): 0/30, 2/30, 20/30, 20/60, 20.5, 90, 22/90; Flow: 18 ml/min; Solubility: ACN+THF+water; Ambient temperature]. The fractions were lyophilized to obtain pure Compound 1 (11 mg, 6%) as an off-white solid. $^1$H NMR (400 MHz, chloroform-d) δ ppm 7.98-8.10 (m, 2H) 7.49-7.59 (m, 1H) 7.37-7.48 (m, 2H) 6.47-6.57 (m, 1H) 6.33-6.45 (m, 2H) 6.28 (br d, J=8.99 Hz, 1H) 5.93-6.09 (m, 1H) 5.72-5.81 (m, 1H) 5.62 (dd, J=15.79, 6.14 Hz, 1H) 5.47-5.56 (m, 1H) 4.44-4.54 (m, 1H) 4.21 (br t, J=6.58 Hz, 1H) 3.99 (br dd, J=4.82, 2.63 Hz, 1H) 3.62-3.75 (m, 4H) 3.47-3.57 (m, 2H) 2.86-3.02 (m, 2H) 2.53-2.74 (m, 2H) 2.33-2.48 (m, 1H) 2.20-2.31 (m, 3H) 2.10-2.18 (m, 1H) 1.89-2.04 (m, 4H) 1.69-1.86 (m, 7H) 1.38-1.50 (m, 3H) 1.22-1.33 (m, 3H) 1.14-1.20 (m, 3H) 1.01-1.11 (m, 3H) 0.79-0.93 (m, 1H); LCMS: 93.71% (612.49, M+H), RT: 5.09, 5.13 min.

Example 2

Synthesis of (Z)-5-((2R, 3R, 5S, 6S)-6-((2E, 4E)-5-((3R, 4R, 5R, 7S)-4-hydroxy-7-(2-methoxy-2-oxo-ethyl)-1,6-dioxaspiro[2.5]octan-5-yl)-3-methylpenta-2,4-dienyl)-2,5-dimethyltetrahydro-2H-pyran-3-ylamino)-5-oxopent-3-en-2-yl 4-fluorobenzoate, Compound 2

Part A:

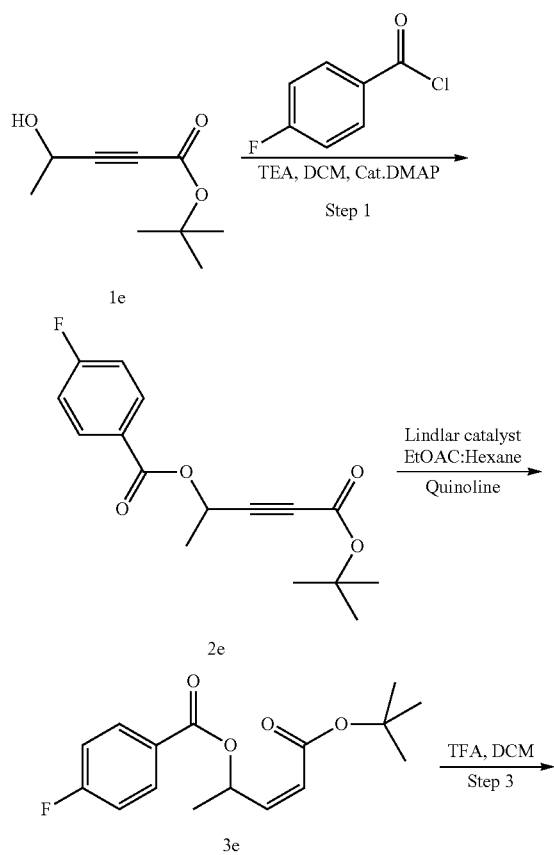

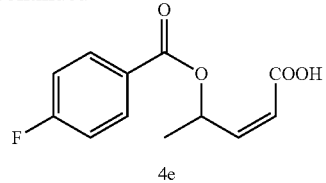

Step 1. 5-(tert-Butoxy)-5-oxopent-3-yn-2-yl 4-fluorobenzoate, Compound 2e

A solution of Compound 1e (1 g, 9.41 mmol) in dry DCM (50 mL) was cooled to −10° C., then triethylamine (6.41 ml, 47.05 mmol) and DMAP (115 mg, 0.941 mmol) was added. After 5 minutes, 4-fluorobenzoyl chloride (1.43 ml, 12.233 mmol) was added dropwise to the reaction mixture. The reaction mixture was allowed to cool to room temperature over 2 hours. The progress of the reaction was monitored by TLC (10% EtOAc in petroleum ether, RF=0.3, UV and KMnO$_4$ active). After completion of the reaction, the reaction mixture was diluted with DCM (100 ml), then washed with water and brine solution (1×50 ml) and dried over anhydrous sodium sulfate. The solvent was removed under reduced pressure and the crude compound was isolated. The crude compound was purified by column chromatography (100-200 silica gel/eluent 5% EtOAc in petroleum ether) to give Compound 2e (900 mg, 53%) as an off white solid. $^1$H NMR (400 MHz, chloroform-d) δ=8.12-8.04 (m, 2H), 7.17-7.07 (m, 2H), 5.76 (q, J=6.8 Hz, 1H), 1.67 (d, J=6.8 Hz, 3H), 1.49 (s, 9H).

Step 2. 5-(tert-Butoxy)-5-oxopent-3-en-2-yl 4-fluorobenzoate, Compound 3e

To a solution of Compound 2e (900 mg, 3.08 mmol) in EtOAc:hexane (30 ml+10 ml) was added quinoline (0.5 ml) and Lindlar catalyst (520 mg, 4.88 mmol) under argon purging. After 5 minutes of purging, the reaction mixture was stirred under hydrogen balloon pressure for 3 h. The progress of the reaction was monitored by TLC (10% EtOAc in petroleum ether, RF=0.36, UV and KMnO$_4$ active). After completion of reaction, the reaction mixture was filtered through celite, the filtrate concentrated under vacuum and the crude product isolated. The crude product was purified by column chromatography (100-200 silica gel; eluent 6% EtOAc in petroleum ether) and to yield Compound 3e (605 mg, 66%) as a yellow gummy liquid. $^1$H NMR (400 MHz, DMSO-d$_6$) δ=8.04 (dd, J=5.6, 8.7 Hz, 2H), 7.36 (t, J=8.8 Hz, 2H), 6.38-6.28 (m, 2H), 5.83-5.76 (m, 1H), 1.50-1.40 (m, 12H); LCMS: 85.63% (295.16, M+H), RT: 4.30 min.

Step 3. (Z)-4-((4-Fluorobenzoyl)oxy)pent-2-enoic acid, Compound 4e

To a stirred solution of Compound 3e (600 mg, 2.04 mmol) in dry DCM (20 mL), was cooled to −10° C. and trifluoroacetic acid (2.4 ml) was added dropwise to the reaction mixture. The reaction mixture was allowed to warm to 25° C. and was stirred for 3 h. The progress of the reaction was monitored by TLC (30% EtOAc in petroleum ether, RF=0.15, UV and KMnO$_4$ active). After completion of reaction, the reaction mixture was concentrated under vacuum and the crude compound was washed with 50% diethyl ether in n-pentane (2×10 ml) and dried under vacuum to give Compound 4e (383 mg, 78%) as an off-white solid. ¹H NMR (400 MHz, DMSO-d₆) δ=12.64 (br s, 1H), 8.03 (dd, J=5.6, 8.7 Hz, 2H), 7.36 (t, J=8.9 Hz, 2H), 6.43-6.32 (m, 2H), 5.84 (d, J=10.5 Hz, 1H), 1.43 (d, J=6.1 Hz, 3H); D₂O (400 MHz, DMSO-d₆) δ=8.07-8.02 (m, 2H), 7.39-7.33 (m, 2H), 6.42-6.33 (m, 2H), 5.88-5.83 (m, 1H), 1.46-1.41 (m, 3H).

Part B:

1.47-1.55 (m, 5H) 1.69-1.85 (m, 4H) 1.89-2.03 (m, 2H) 2.19-2.32 (m, 1H) 2.34-2.49 (m, 1H) 3.49-3.59 (m, 1H) 3.62-3.75 (m, 1H) 3.91-4.04 (m, 1H) 4.87-5.01 (m, 1H) 5.11 (d, J=17.44 Hz, 1H) 5.47 (br d, J=3.81 Hz, 1H) 5.76 (ddd, J=11.61, 5.94, 1.20 Hz, 1H) 5.88-6.09 (m, 2H) 6.18-6.58 (m, 3H) 7.05-7.16 (m, 2H) 7.99-8.10 (m, 2H); LCMS: 87.8% (430.07, M+H), RT: 2.50 min.

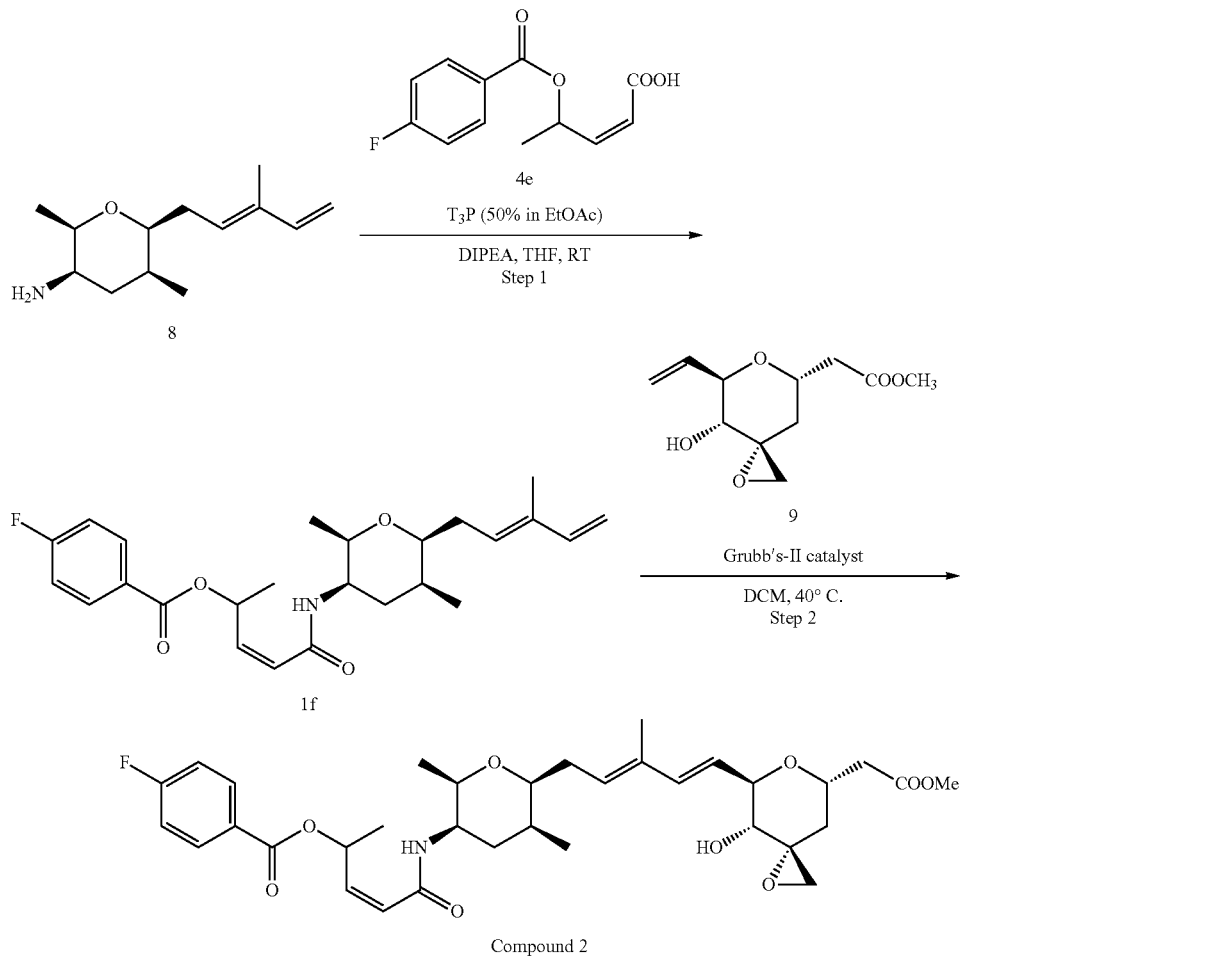

Step 1. (Z)-5-((2R, 3R, 5S, 6S)-2,5-dimethyl-6-((E)-3-methylpenta-2,4-dienyl)tetrahydro-2H-pyran-3-ylamino)-5-oxopent-3-en-2-yl 4-fluorobenzoate, Compound 1f To a stirred solution of Compound 8 (400 mg, 1.91 mmol), Compound 4e (273 mg, 1.14 mmol) in THF (12 ml), DIPEA (1.23 g, 9.55 mmol), and T3P (1.82 g) were added at room temperature. The reaction mixture was stirred at room temperature for 4 h. The reaction progress was monitored by TLC (30% EtOAc in petroleum ether, RF=0.2, PMA active). The reaction mixture was concentrated under reduced pressure. The crude product was purified by column chromatography (100-200 silica gel/eluent 10% EtOAc in petroleum ether) to give Compound 1f (220 mg) as a colorless gum. ¹H NMR (400 MHz, chloroform-d) δ ppm 0.99-1.08 (m, 3H) 1.11-1.20 (m, 3H) 1.36-1.44 (m, 3H)

Step 2. (Z)-5-((2R, 3R, 5S, 6S)-6-((2E, 4E)-5-((3R, 4R, 5R, 7S)-4-hydroxy-7-(2-methoxy-2-oxoethyl)-1,6-dioxaspiro[2.5]octan-5-yl)-3-methylpenta-2,4-dienyl)-2,5-dimethyltetrahydro-2H-pyran-3-ylamino)-5-oxopent-3-en-2-yl 4-fluorobenzoate, Compound 2

To a stirred solution of Compound 1f (100 mg, 0.232 mmol) in DCM (10 ml), Compound 9 (150 mg, 0.657 mmole) and Grubbs-II catalyst (41 mg, 0.2 mmol) were added at room temperature under argon atmosphere. The reaction mixture was stirred at 40° C. for 5 h. The reaction progress was monitored by TLC (50% EtOAc in petroleum ether, RF=0.1, UV active). The reaction mixture was filtered through celite and washed with DCM (2 ml). The solvent was concentrated under reduced pressure. The crude product was purified by preparative HPLC [X Bridge column (150× 19) mm, 5 u; mobile phase A: 10 mm ABC; mobile phase B: acetonitrile; method:—(T/% B): 0/30, 2/30, 20/30; flow.—

18 ml/min; solubility:—ACN+THF+water; ambient temperature]. The resulting fractions were lyophilized to obtain pure Compound 2 (5.8 mg) as a white solid. ¹H NMR (400 MHz, chloroform-d) δ ppm 0.99-1.09 (m, 3H) 1.13-1.20 (m, 3H) 1.22-1.36 (m, 1H) 1.52 (br s, 1H) 1.69-1.84 (m, 7H) 1.88-2.05 (m, 3H) 2.10-2.31 (m, 2H) 2.33-2.47 (m, 1H) 2.60-2.78 (m, 2H) 2.88-3.04 (m, 2H) 3.48-3.58 (m, 2H) 3.62-3.76 (m, 4H) 3.98 (br dd, J=5.26, 2.85 Hz, 2H) 4.10-4.24 (m, 1H) 4.40-4.56 (m, 1H) 5.52 (br s, 1H) 5.58-5.68 (m, 1H) 5.72-5.81 (m, 2H) 5.89-6.10 (m, 2H) 6.32-6.58 (m, 2H) 7.10 (t, J=8.55 Hz, 1H) 7.95-8.11 (m, 2H); LCMS: 94.37% (630.16, M+H), RT: 4.73 min and 4.77 min.

Example 3

Synthesis of Methyl 2-((3R, 5S, 7R, 8R)-7-((1E, 3E)-5-((2S, 3S, 5R, 6R)-5-((Z)-4-(3,5-dimethyl-1H-1,2,4-triazol-1-yl)pent-2-enamido)-3,6-dimethyltetrahydro-2H-pyran-2-yl)-3-methylpenta-1,3-dienyl)-8-hydroxy-1,6-dioxaspiro[2.5]octan-5-yl)acetate, Compound 3

Part A:

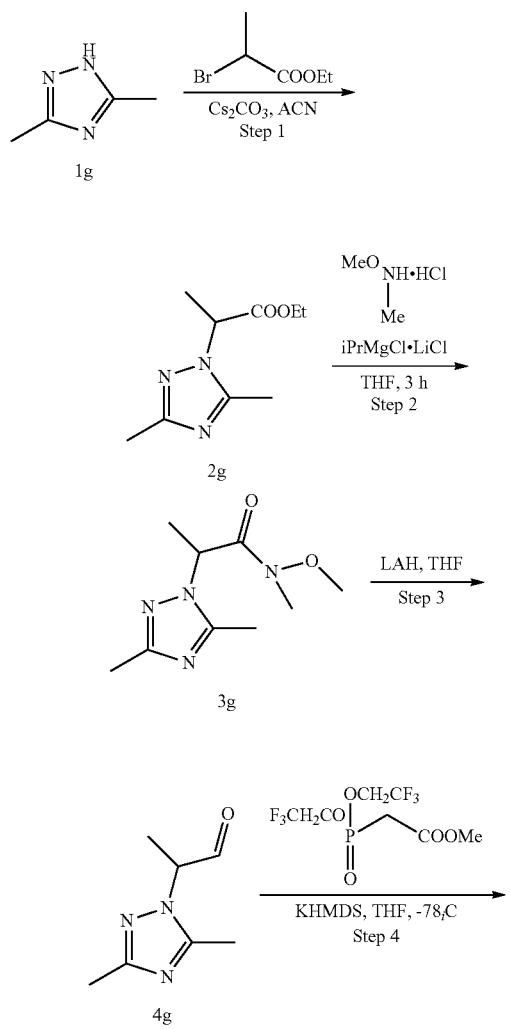

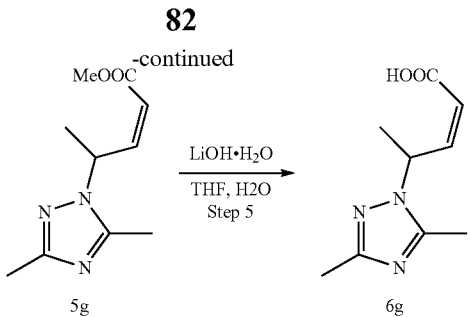

Step 1. Ethyl 2-(3,5-dimethyl-1H-1,2,4-triazol-1-yl)propanoate, Compound 2g

To a stirred solution of Compound 1g in ACN (100 ml) were added Cs₂CO₃ (125.6 g, 386.15 mmol) and ethyl 2-bromopropanoate (39.43 ml, 283.15 mmol) at 25° C. The mixture was stirred for 16 h at room temperature. The progress of the reaction was monitored by TLC (5% MeOH in DCM, Rf=0.5, PMA active). After completion of the reaction, the reaction mixture was filtered and washed with EtOAc (300 ml). The filtrate was washed with water (2×200 ml), brine (2×200 ml). The organic layer was dried over anhydrous sodium sulfate and concentrated to obtain 35 g crude product. The crude product was purified by normal phase column chromatography using silica (100-200 mesh), eluting with 2% MeOH in DCM. The collected fractions were evaporated to obtain Compound 2g (30 g, 59.17%) as a pale yellow liquid. The desired isomer was confirmed by NOE analysis. ¹H NMR (400 MHz, DMSO-d₆) δ ppm: 5.22-5.34 (m, 1H), 4.03-4.18 (m, 2H), 2.32 (s, 3H), 2.16 (s, 3H), 1.60 (d, J=7.23 Hz, 3H), 1.06-1.19 (m, 3H); LCMS: 75.07% (198.17, M+H), RT=1.18 min.

Step 2. 2-(3,5-Dimethyl-1H-1,2,4-triazol-1-yl)-N-methoxy-N-methylpropanamide, Compound 3g To a stirred solution of Compound 2g (5 g, 25.38 mmol) in anhydrous THF (10 ml/mmol) was added N,O-dimethyl hydroxylamine hydrochloride (4.9 g 50.76 mmol) and then isopropyl magnesium chloride lithium chloride complex (58.57 ml, 76.14 mmol, 1.3 M in THF) was slowly added at 0° C. The mixture was stirred for 3 h at room temperature. The progress of the reaction was monitored by TLC (neat EtOAc, Rf=0.3, PMA active). After completion of reaction, it was quenched with satd. aq. ammonium chloride solution, extracted with ethyl acetate (3×50 ml) and dried with sodium sulfate. The solvent was evaporated under reduced pressure to obtain Compound 3g (3.9 g, 73.58%) as a pale yellow gum. ¹H NMR (400 MHz, DMSO-d₆) δ ppm: 5.27 (m, 1H), 3.38 (s, 3H), 3.21 (s, 3H), 2.43 (s, 3H), 2.34 (s, 3H), 1.66 (s, 3H), 1.61 (d, 3H); LCMS: 79.07% (213.01, M+H), RT=1.40 min.

Step 3. 2-(3,5-Dimethyl-1H-1,2,4-triazol-1-yl)propanal, Compound 4g

To a stirred solution of Compound 3g (3.9 g, 18.39 mmol) in THF (8 ml) was added LAH (10.11 ml, 20.23 mmol, 2.0 M in THF). After the addition, the reaction mixture was stirred at 0° C. for 2 h. The progress of the reaction was monitored by TLC (neat EtOAc, Rf=0.25, 2, 4-DNP active). After completion of reaction, it was quenched with satd. aq.

ammonium chloride solution, extracted with ethyl acetate (3×50 ml) and dried over anhydrous sodium sulfate. The solvent was evaporated under reduced pressure to obtain Compound 4g (2.6 g, 92%). The crude product was used for next step without purification. The aldehyde compound was confirmed by $^1$H NMR.

Step 4. (Z)-Methyl 4-(3,5-dimethyl-1H-1,2,4-triazol-1-yl)pent-2-enoate, Compound 5g To a stirred solution of methyl 2-(bis(2,2,2-trifluoroethoxy)phosphoryl)acetate (5.4 g, 16.9 mmol) in anhydrous THF (10 ml) was added 18-crown-6 (22.43 g, 84.96 mmol) and KHMDS (16.99 ml, 16.99 m mol, 1.0 M in THF) at −75° C. and the reaction mixture was stirred for 20 min. Then Compound 4g (2.6 g, 16.993 mmol) in (5 ml) THF was added to the reaction mixture, which was allowed to warm to 25° C. and stirred for 2 h. The progress of the reaction was monitored by TLC (50% EtOAc in hexane, Rf=0.3, UV active). After completion of the reaction, it was quenched with satd. aq. ammonium chloride solution, the product was extracted with ethyl acetate (3×50 ml), and dried over anhydrous sodium sulfate. Solvent was evaporated under reduced pressure to obtain 3 g of crude product. The crude product was purified by silica column using 50% EtOAc in hexane. The product in the collected fractions were identified by UV, which were evaporated under reduced pressure to obtain Compound 5g (500 mg, 14.08%) as a pale yellow gum. $^1$H NMR (400 MHz, DMSO-d$_6$) δ ppm: 6.48-6.53 (dd, J=8.8 Hz 1H), 6.19-6.23 (m, 1H), 5.87-5.84 (d, J=1.2 Hz 1H), 3.76 (s, 3H), 2.42 (s, 3H), 2.34 (s, 3H), 1.58-1.60 (d, 3H); LCMS: 74.79% (210.11, M+H), RT=1.24 min.

Step 5. (Z)-4-(3,5-Dimethyl-1H-1,2,4-triazol-1-yl)pent-2-enoic acid, Compound 6g To a stirred solution of Compound 5g (500 mg, 16.99 mmol) in THF (8 ml) and water (2 ml) was added LiOH.H$_2$O (120.57 g, 2.87 mmol). The reaction mixture was stirred for 2 h at room temperature. The progress of the reaction was monitored by TLC (20% MEOH in DCM, Rf=0.4, UV active). After completion of the reaction, solvent was evaporated under reduced pressure to obtain the crude product, which was treated with an acid and a base treatment. The crude compound was dissolved in 1 ml water and extracted with diethyl ether (5 ml). The separated aqueous layer was acidified with saturated citric acid (0.2 ml, pH=5) and extracted with 20% MeOH in DCM (2×20 ml). The separated organic layer was dried over anhydrous sodium sulfate and the solvent evaporated under reduced pressure to obtain 300 mg of the desired product. This 300 mg of the final product was combined with earlier batch (80 mg, LCMS 97%), washed with water (1 ml) and the filtered solid dried under vacuum to obtain Compound 6g (240 mg, 39.02%) as an off-white solid. The JJ constant coupling of the olefinic double bond indicated that the compound is the Z geometric isomer. $^1$H NMR (400 MHz, DMSO-d$_6$) δ ppm: 12.76 (br s, 1H), 6.36 (dd, J=11.18, 8.99 Hz, 1H), 6.00-6.16 (m, 1H), 5.83 (d, J=11.40 Hz, 1H), 2.30 (s, 3H), 2.18 (s, 3H), 1.48 (d, J=6.58 Hz, 3H); LCMS: 98.64% (196.22, M+H), RT=1.10 min.

Part B:

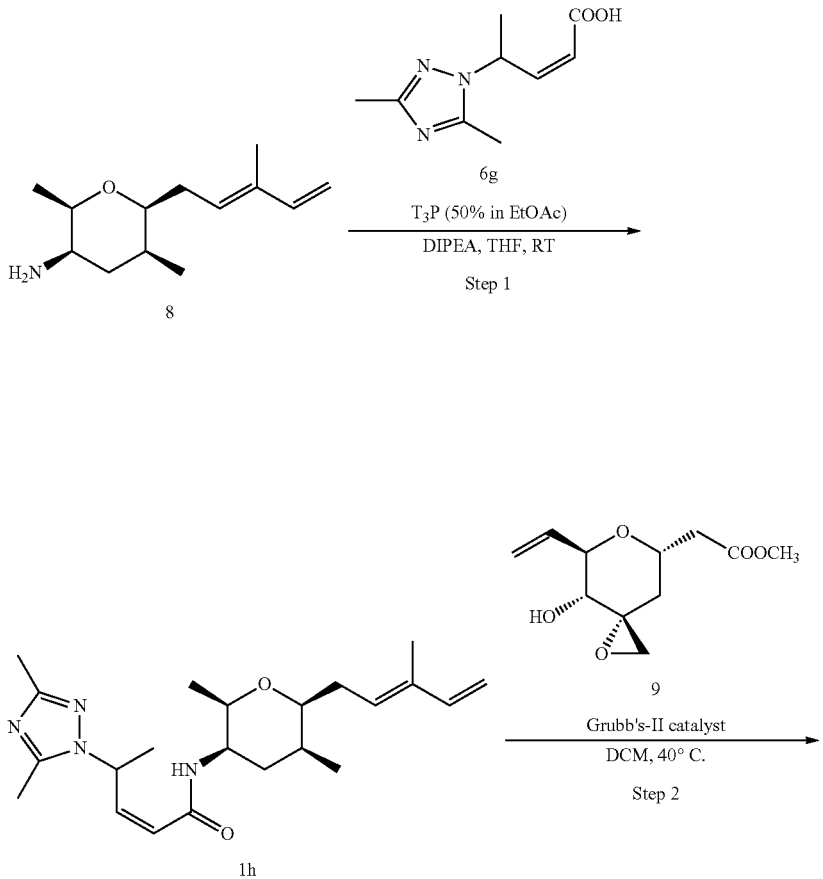

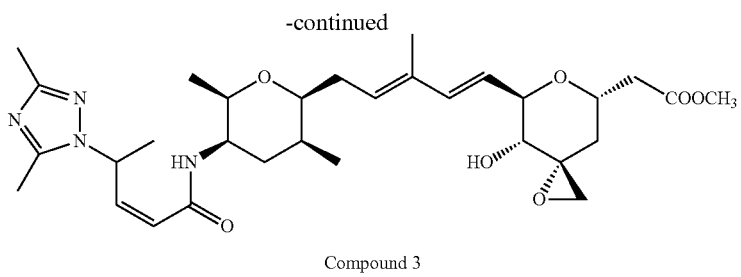

Compound 3

Step-1. (Z)-4-(3,5-dimethyl-1H-1,2,4-triazol-1-yl)-N-((2R, 3R, 5S, 6S)-2,5-dimethyl-6-((E)-3-methyl-penta-2,4-dienyl)tetrahydro-2H-pyran-3-yl)pent-2-enamide, Compound 1h To a stirred solution of Compound 8 (300 mg, 1.435 mmol), Compound 6g (167.6 mg, 0.85 mmol) in THF (10 ml), DIPEA (924 mg, 7.15 mmole) and T$_3$P (50% in EtOAc) (1.36 g, 4.29 mmol) were added at room temperature. The reaction mixture was stirred at room temperature for 5 h. The reaction progress was monitored by TLC (EtOAc, RF=0.1, UV active). The reaction solvent was concentrated under reduced pressure to obtain the crude product. The crude product was purified by column chromatography (100-200 silica gel/eluent 90% EtOAc in petroleum ether) to give Compound 1h (130 mg, 23.5%) as a colorless gum. $^1$H NMR (400 MHz, chloroform-d) δ ppm 6.53 (br d, J=1.96 Hz, 1H) 6.23-6.42 (m, 2H) 5.81-5.94 (m, 1H) 5.68-5.78 (m, 1H) 5.45 (br t, J=7.09 Hz, 1H) 5.30 (s, 2H) 5.05-5.16 (m, 1H) 4.88-5.03 (m, 1H) 4.12 (q, J=7.34 Hz, 3H) 3.89-3.99 (m, 1H) 3.64-3.76 (m, 1H) 3.51-3.60 (m, 1H) 2.72-2.90 (m, 1H) 2.32-2.50 (m, 7H) 2.19-2.29 (m, 2H) 2.08-2.14 (m, 3H) 2.05 (s, 5H) 1.87-1.98 (m, 3H) 1.70-1.85 (m, 4H) 1.59 (dd, J=6.60, 3.18 Hz, 3H) 1.39-1.46 (m, 3H) 1.19-1.33 (m, 11H) 1.09-1.19 (m, 3H) 1.01 (br dd, J=16.14, 7.34 Hz, 3H) 0.81-0.92 (m, 2H); LCMS: 82.3% (387.38, M+H), RT: 2.31, 2.35 min.

Step 2. Methyl 2-((3R, 5S, 7R, 8R)-7-((1E, 3E)-5-((2S, 3S, 5R, 6R)-5-((Z)-4-(3,5-dimethyl-H-1,2,4-triazol-1-yl)pent-2-enamido)-3,6-dimethyltetrahydro-2H-pyran-2-yl)-3-methylpenta-1,3-dienyl)-8-hydroxy-1,6-dioxaspiro[2.5]octan-5-yl)acetate, Compound 3

To a stirred solution of Compound 1h (100 mg, 0.258 mmol) and Compound 9 (100 mg, 0.438 mmol) in DCM (10 mL) was added Grubbs-II catalyst (65.7 mg, 0.0774 mmol) at room temperature under argon atmosphere. The reaction mixture was stirred at 40° C. for 5 h. The reaction progress was monitored by TLC (100% EtOAc, UV active). The reaction mixture was filtered through a celite pad and washed with DCM (2 mL). The solvent was concentrated under reduced pressure to obtain the crude product. The crude product was purified by preparative HPLC [Mobile Phase A: 10 mm ABC; Mobile Phase B: Acetonitrile; Column: X-Bridge (150×19 mm), 5u; Method: (T/% B): 0/30, 2/30, 20/30, 20/60, 20.5, 90, 22/90; Flow: 18 ml/min; Solubility: –ACN+THF+water Ambient temperature]. The collected fractions were lyophilized to obtain pure product Compound 3 (3 mg, 1.9%) as an off-white solid. $^1$H NMR (400 MHz, chloroform-d) δ ppm 6.44-6.60 (m, 1H) 6.22-6.43 (m, 2H) 5.86 (td, J=7.23, 1.32 Hz, 1H) 5.77 (br d, J=9.21 Hz, 1H) 5.58-5.72 (m, 1H) 5.51 (br t, J=7.02 Hz, 1H) 4.44-4.56 (m, 1H) 4.20 (br t, J=–6.80 Hz, 1H) 3.87-4.00 (m, 2H) 3.60-3.76 (m, 5H) 3.45-3.57 (m, 3H) 2.89-3.02 (m, 2H) 2.61-2.78 (m, 4H) 2.40-2.49 (m, 4H) 2.29-2.38 (m, 9H) 2.13-2.26 (m, 4H) 2.07-2.11 (m, 3H) 1.88-2.03 (m, 4H) 1.71-1.85 (m, 6H) 1.51-1.55 (m, 3H) 1.47 (br d, J=2.85 Hz, 2H) 1.43 (s, 6H) 1.22-1.35 (m, 3H) 1.16 (d, J=6.36 Hz, 3H) 0.98 (d, J=7.45 Hz, 3H); LCMS: 75% (587.17, M+H), RT: 2.95 min.

Example 4

Synthesis of Methyl 2-((3R, 5S, 7R, 8R)-8-hydroxy-7-((1E, 3E)-5-((2S,3S,5R,6R)-5-((Z)-4-(isoxazol-3-yl)pent-2-enamido)-3,6-dimethyltetrahydro-2H-pyran-2-yl)-3-methylpenta-1,3-dien-1-yl)-1,6-dioxaspiro[2.5]octan-5-yl)acetate, Compound 4

Part A:

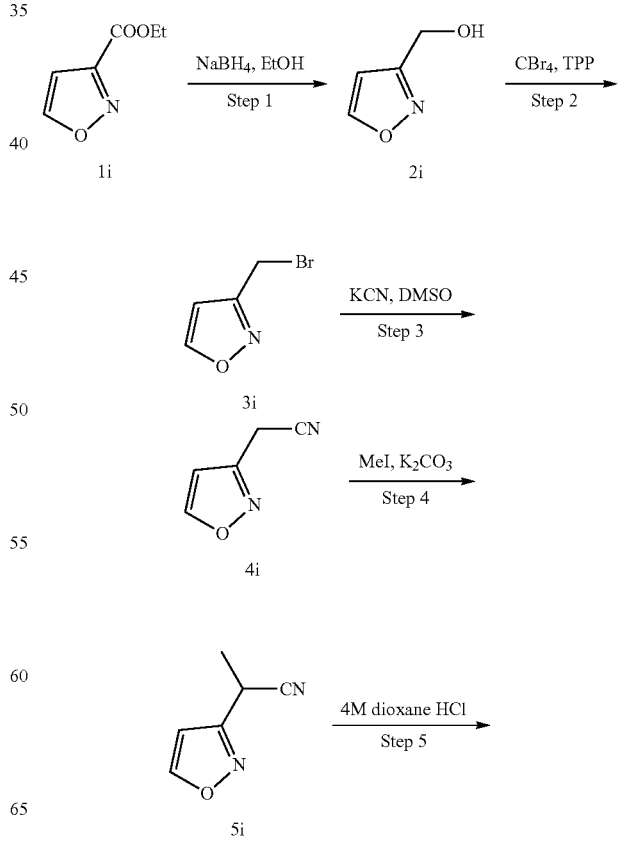

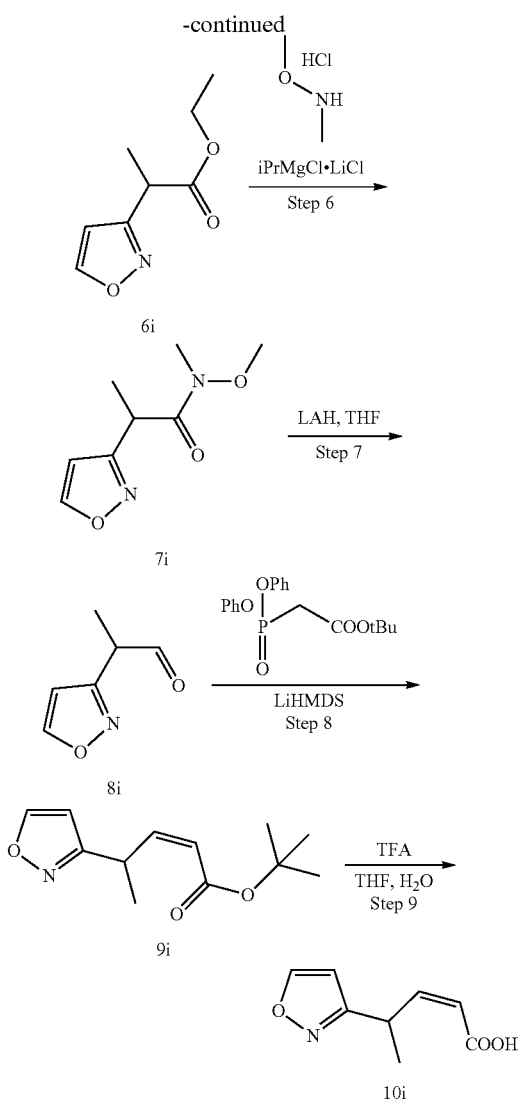

Step 1. Isoxazol-3-ylmethanol, Compound 2i

A stirred solution of ethyl isoxazole-3-carboxylate (Compound 1i) (24 g, 170.2 mmol) in ethanol (400 ml) was cooled to 0° C., sodium borohydride (16.17 g, 425.5 mmol) was added and the mixture stirred for 3 h. The progress of the reaction was monitored by TLC (10% methanol in DCM, Rf: 0.3, iodine and UV active). The reaction mixture was evaporated under reduced pressure, quenched with ice cold water (30 ml), extracted with 10% methanol in DCM (6×500 ml), and the organic layer dried over anhy. sodium sulfate. The organic solvent was evaporated under reduced pressure to obtain Compound 2i (16.8 g, 99.32%) as a colorless oil. GCMS: 56% (99 M/Z), RT: 5.109 min; $^1$H NMR (400 MHz, chloroform-d) δ ppm 2.238 (S, 1H), 4.813 (s, 2H) 6.428-6.386 (d, J=2 Hz, 1H) 8.392 (d, J=2 Hz, 1H).

Step 2. 3-(Bromomethyl)isoxazole, Compound 3i

A stirred solution of Compound 2i (16.8 g, 169.69 mmol) in DCM (350 ml) was cooled to 0° C., triphenyl phosphine (44.5 g, 169.69 mmol) and CBr$_4$ (56.27 g, 169.69 mmol) were added and the mixture stirred for 4 h at room temperature. The progress of the reaction was monitored by TLC (20% ethyl acetate in hexane, Rf: 0.7, iodine and UV active). The reaction mixture was washed with water (2×100 ml), brine solution (100 ml). The organic layer was dried over Na$_2$SO$_4$, filtered and concentrated to obtain the crude product as pale yellow liquid (23 g), which was purified by normal phase column chromatography using silica gel (100-200 mesh) and eluting with 10% ethyl acetate in hexane. The collected fractions were evaporated to obtain Compound 3i (16.5 g, 62.6%) as a pale yellow liquid. $^1$H NMR (400 MHz, chloroform-d) δ ppm 4.461 (s, 2H) 6.463 (d, J=1.6 Hz, 1H) 8.396 (d, J=1.6 Hz, 1H); LCMS: 85% (162, M+H), RT: 1.69 min.

Step 3. 2-(Isoxazol-3-yl) Acetonitrile, Compound 4i

To a stirred solution of Compound 3i (16.5 g, 102.4 mmol) in DMSO (35 ml) and water (15 ml) was added KCN (9.92 g, 153.72 mmol) at 0° C., then reaction was allowed to warm to 25° C. and was stirred for 3 h. The progress of the reaction was monitored by TLC (30% ethyl acetate in hexane, Rf: 0.5, KMnO$_4$ active). The reaction mixture was diluted with water (100 ml) and extracted with ethyl acetate (2×150 ml). The combined organic layers were washed with water (100 ml) and brine solution (100 ml), dried over Na$_2$SO$_4$ and concentrated under reduced pressure to obtain the crude compound (12 g), which was purified by normal phase column chromatography using silica gel (100-200 mesh) and 20% EtOAc in hexane as an eluent. The collected fractions were evaporated to obtain Compound 4I (8 g, 72.7%) as a pale yellow liquid. $^1$H NMR (400 MHz, chloroform-d) δ ppm 3.87 (s, 2H) 6.49 (d, J=1.47 Hz, 1H) 8.48 (d, J=1.47 Hz, 1H); LCMS: 96.57% (109.09, M+H), RT: 1.19 min.

Step 4. 2-(Isoxazol-3-yl)propanenitrile, Compound 5i

To a solution of Compound 4i (8 g, 92.5 mmol) in THF (300 ml) was added KOtBu (9.35 g, 83.33 mmol) at 0° C. and the mixture was stirred for 20 min. Then methyl iodide (28 ml, 462.5 mmol) was added to the reaction at 0° C. and the reaction mixture was allowed to warm to 25° C. and stirred for 16 h. The progress of the reaction was monitored by TLC (30% ethyl acetate in hexane, Rf=0.45, KMnO$_4$ active). After completion of the reaction, the mixture was filtered, the filtrate was diluted with ethyl acetate (250 ml) and washed with water (100 ml) and brine solution (100 ml). The organic layer was dried over Na$_2$SO$_4$ and concentrated under reduced pressure to obtain the crude compound (15 g), which was purified by normal phase column chromatography using silica gel (100-200 mesh) and eluting with 15% EtOAc in hexane. The collected fractions were evaporated to obtain Compound 5i (5 g, 55.37%) as a pale yellow liquid. $^1$H NMR (400 MHz, chloroform-d) δ ppm 1.748-1.730 (d, J=7, 3H), 4.178-4.113 (m, 1H), 6.49 (d, J=1.47 Hz, 1H) 8.48 (d, J=1.47 Hz, 1H); LCMS: 92.66% (123.16, M+H), RT: 1.44 min.

Step 5. Ethyl 2-(isoxazol-3-yl)propanoate, Compound 6i

To a solution of Compound 5i (4.5 g, 36.88 mmol) in ethanol (45 ml) was added 4.0 M HCl in 1,4-dioxane (45 ml) in a 250-ml tube, which was then sealed. The tube was heated to 80° C. and stirred for 24 h. The progress of the reaction was monitored by TLC (30% ethyl acetate in hexane, Rf=0.7, KMNO$_4$ active). After completion of reaction, the reaction mixture was concentrated, and the residue was taken up in ethyl acetate (100 ml), and washed with NaHCO$_3$ solution (2×50 ml), water (50 ml), and brine solution (50 ml). The organic layer was dried over Na$_2$SO$_4$ and concentrated under reduced pressure to obtain the crude compound (3.5 g), which was purified by normal phase column chromatography using silica gel (100-200 mesh) and eluting with 10% ethyl acetate in hexane. The collected fractions were evaporated to get Compound 6i (6 g, 96.3%) as a pale yellow liquid. $^1$H NMR (400 MHz, chloroform-d) δ ppm 8.34-8.38 (m, 1H) 6.37-6.42 (m, 1H) 4.15-4.22 (m, 2H) 3.96-4.03 (m, 1H) 1.55-1.58 (m, 3H) 1.25-1.28 (m, 3H); LCMS: 88.80% (170.16, M+H), RT: 1.97 min.

Step 6.
2-(Isoxazol-3-yl)-N-methoxy-N-methylpropanamide, Compound 7i

To a stirred solution of Compound 6i (6 g, 35.5 mmol) in THF (200 ml) was added N,O-dimethylhydroxylamine hydrochloride (6.92 g, 71 mmol) and the reaction mixture cooled to 0° C. Isopropyl magnesium chloride lithium chloride complex was then added (1.3 M) (109.2 ml, 142 mmol). The reaction mixture stirred for 3 h at 0° C. The progress of the reaction was monitored by TLC (50% ethyl acetate in hexane, Rf: 0.4, KMNO$_4$ active). The reaction mixture was quenched by using saturated aq. ammonium chloride solution, extracted with ethyl acetate (3×100 ml). The combined organic layer was dried over sodium sulfate and concentrated under reduced pressure to obtain the crude compound (9 g). The crude product was purified by silica gel column using 50% ethyl acetate in hexane as an eluent. The pure fractions were collected and evaporated under reduced pressure to obtain Compound 7i (2 g, 30.62%) as pale yellow oil. $^1$H NMR (400 MHz, chloroform-d) δ ppm 1.50 (d, J=7.02 Hz, 3H) 3.21 (s, 3H) 3.63-3.71 (m, 3H) 4.53 (br d, J=6.14 Hz, 1H) 6.45 (d, J=1.53 Hz, 1H) 8.33 (d, J=1.53 Hz, 1H); LCMS: 97.05% (185.22, M+H), RT: 1.23 min.

Step 7. 2-(isoxazol-3-yl)propanal, Compound 8i

To a stirred solution of Compound 7i (2 g, 10.87 mmol) in THF (50 ml) was added LAH (5.43 ml, 10.87 mmol, 2 M in THF) at −70° C. After the addition, the reaction mixture was stirred at 0° C. for 1 h. The progress of the reaction was monitored by TLC (50% ethyl acetate in hexane, RF=0.15, 2,4-DNP active). After completion of the reaction, the mixture was quenched with a sodium sulfate slurry, and stirred for 30 min at room temperature. The solid was filtered solid, washed with ethyl acetate (50 ml). The filtrate was dried over anhy. sodium sulfate, and evaporated under reduced pressure to afford Compound 8I (1.2 g). The crude product was used in the next step without purification. The $^1$H NMR showed the characteristic aldehyde proton at 9.8 ppm with an integration value of 0.12 (other peak values are not listed due to impure compound).

Step 8. (Z)-Methyl 4-(1H-1, 2, 3-triazol-1-yl) pent-2-enoate, Compound 9i

To a stirred solution of 18-crown-6 (19.18 g, 72.58 mmol) and tert-butyl 2-(diphenoxyphosphoryl)acetate (3.34 g, 9.6 mmol) in THF (40 ml) was added 1 M KHMDS in THF solution (9.6 ml, 9.6 mmol) dropwise at −75° C. After the addition, reaction mixture was stirred at −75° C. for 20 min. Then Compound 8i (1.2 g, 14.51 mmol) in THF (10 ml) was added to the reaction mixture at −75° C. After the addition, the reaction mixture was stirred for 2 h at room temperature. The progress of the reaction was monitored by TLC (30% ethyl acetate in hexane, RF=0.6, UV active). After completion of the reaction, it was quenched with sat. aqueous ammonium chloride solution, extracted with ethyl acetate (3×30 ml) and dried over anhy. sodium sulfate. The solvent was evaporated under reduced pressure and 4 g of crude product were obtained. The crude product was purified by silica column using 15% ethyl acetate in hexane as a gradient. The pure fractions were collected and evaporated under reduced pressure to get Compound 9i (430 mg, 19.6%) as a yellow gum. $^1$H NMR (400 MHz, chloroform-d) δ ppm 1.42 (d, J=7.02 Hz, 3H), 1.55 (s, 9H) 5.002-4.961 (m, 1H) 5.796-5.767 (d, J=11.6 Hz, 1H) 6.255-6.196 (m, 2H) 8.316-8.312 (d, J=1.6 Hz, 1H); Z geometric isomer confirm by JJ constant coupling value of olefin bond: 11.6 Hz; LCMS: 85.78% (224.26, M+H), RT: 2.49 min.

Step 9. (Z)-4-(isoxazol-3-yl) pent-2-enoic acid, Compound 10i

To a stirred solution of Compound 9i (420 mg, 1.88 mmol) in DCM (42 ml) was added TFA (4.2 ml, 41.50 mmol) at 25° C. and the mixture stirred for 4 h. The progress of the reaction was monitored by TLC (30% EtOAc in petroleum ether, Rf=0.1, UV active). After completion of the reaction, the solvent was evaporated at 25° C. under reduced pressure to obtain the crude product. The crude compound was purified through preparative HPLC [Mobile phase A: 10 FA; Mobile phase B: acetonitrile column: X select phenyl hexyl (150×19) mm, 5u; Flow: 16 ml/min; Method: 0/20, 2/20, 10/50; Solubility:—ACN+Water+THF; Ambient temperature] to obtain Compound 10i (142 mg, 45.2%) as colorless oil. $^1$H NMR (400 MHz, DMSO-d$_6$) δ ppm 1.33 (d, J=7.02 Hz, 3H) 4.90-5.02 (m, 1H) 5.81 (d, J=11.40 Hz, 1H) 6.31 (t, J=10.74 Hz, 1H) 6.57 (d, J=1.32 Hz, 1H) 8.81 (d, J=1.32 Hz, 1H) 12.31 (s, 1H); LCMS: 98.16% (166.15, M−H), RT: 1.43 min.

Part B:

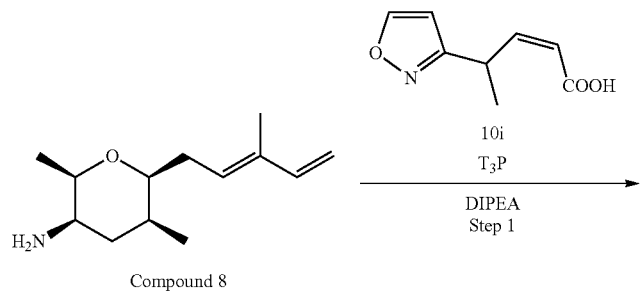

Compound 8

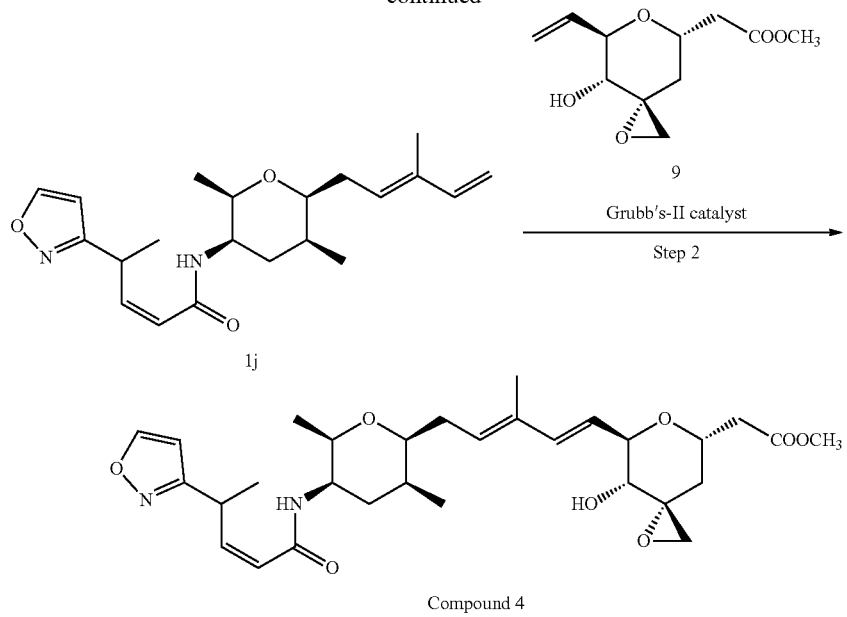

Step 1. (Z)—N-((2R, 3R, 5S, 6S)-2,5-dimethyl-6-((E)-3-methylpenta-2,4-dien-1-yl)tetrahydro-2H-pyran-3-yl)-4-(isoxazol-3-yl)pent-2-enamide, Compound 1j To a stirred solution of Compound 8 (150 mg, 0.716 mmol) and Compound 10i (119 mg, 0.716 mmol) in THF (10 ml) at 23° C., was added DIPEA (0.65 ml, 3.58 mmol) and T$_3$P (50% in EtOAc) (0.68 mL, 2.14 mmol). The reaction mixture was stirred at room temperature for 3 h. The reaction progress was monitored by TLC (50% EtOAc in hexane, R$_f$=0.6, UV visible). After completion, the reaction mixture was concentrated in vacuo to obtain the crude compound. The crude residue was purified by flash chromatography (20 to 50% EtOAc in hexanes) on silica (100-200 mesh) to afford Compound 1j (130 mg, 50.78%) as a pale yellow liquid. $^1$H NMR (400 MHz, chloroform-d) δ ppm 8.27-8.32 (m, 1 H) 6.37 (dd, J=17.33, 10.68 Hz, 1H) 6.24-6.30 (m, 1H) 6.14 (td, J=11.20, 9.97 Hz, 1H) 5.72-5.88 (m, 2H) 5.40-5.50 (m, 1H) 5.06-5.21 (m, 2H) 4.96 (d, J=10.57 Hz, 1H) 3.91-4.02 (m, 1H) 3.63-3.73 (m, 1H) 3.51-3.59 (m, 1H) 2.33-2.45 (m, 1H) 2.19-2.31 (m, 1H) 1.91-1.99 (m, 2H) 1.81 (ddd, J=9.92, 4.96, 2.45 Hz, 1H) 1.76 (s, 3H) 1.43-1.50 (m, 4H) 1.24-1.28 (m, 3H) 1.15 (dd, J=13.19, 6.43 Hz, 3H) 1.02 (dd, J=13.95, 7.41 Hz, 3H); LCMS: 93.58% (359.40, M+H), RT: 2.73 min and 2.75 min.

Step-2. Methyl 2-((3R, 5S, 7R, 8R)-8-hydroxy-7-((1E, 3E)-5-((2S, 3S, 5R, 6R)-5-((Z)-4-(isoxazol-3-yl)pent-2-enamido)-3,6-dimethyltetrahydro-2H-pyran-2-yl)-3-methylpenta-1,3-dien-1-yl)-1,6-dioxaspiro[2.5]octan-5-yl)acetate, Compound 4

To a stirred solution of Compound 1j (120 mg, 0.335 mmol) in DCM (10 ml) at 23° C., Compound 9 (114 mg, 0.502 mmol) and Grubbs-II catalyst (85 mg, 0.10 mmol) were added under a nitrogen atmosphere. The reaction mixture was stirred at 40° C. for 5 h. The reaction progress was monitored by TLC (50% EtOAc in hexanes, R$_F$=0.1, UV visible). The reaction mixture was filtered through celite and washed with DCM (5 ml) and the filtrate was concentrated under reduced pressure to obtain the crude compound. The crude residue was purified by preparative HPLC [Mobile Phase A: 10 mm ABC; Mobile Phase B: acetonitrile; Column: X-select phenyl hexyl (150×19) mm, 5u; Method: (T/% B): 0/20, 2/20, 12/55, 20.50/90, 22/90; Flow: 16 ml/min; Ambient temperature]. The collected fractions were lyophilized to afford Compound 4 (5 mg) as a pale brown gum. $^1$H NMR (400 MHz, chloroform-d) δ ppm 8.30 (s, 1H) 6.38 (br d, J=15.89 Hz, 1H) 6.28 (dd, J=3.30, 1.59 Hz, 1H) 6.07-6.20 (m, 1H) 5.80-5.87 (m, 1H) 5.76 (dd, J=11.13, 3.06 Hz, 1H) 5.63 (dd, J=15.77, 6.24 Hz, 1H) 5.52 (br t, J=6.85 Hz, 1H) 5.05-5.23 (m, 2H) 4.50 (ddd, J=1.68, 7.15, 4.89 Hz, 1H) 4.21 (br t, J=6.72 Hz, 1H) 3.92-4.01 (m, 1H) 3.63-3.75 (m, 7H) 3.46-3.58 (m, 2H) 2.89-3.03 (m, 2H) 2.60-2.74 (m, 2H) 2.34-2.46 (m, 1H) 2.13-2.32 (m, 3H) 1.90-1.99 (m, 2H) 1.71-1.85 (m, 6H) 1.47 (dd, J=6.97, 2.57 Hz, 3H) 1.15 (dd, J=13.45, 6.36 Hz, 3H) 1.02 (dd, J=14.18, 7.34 Hz, 3H); LCMS: 92.45% (559.3, M+H), RT: 4.75 min and 4.80 min.

Example 5

Synthesis of Methyl 2-((3R, 5S, 7R, 8R)-8-hydroxy-7-((1E, 3E)-5-((2S, 3S, 5R, 6R)-5-((Z)-4-(3-methoxyisoxazol-5-yl)pent-2-enamido)-3,6-dimethyltetrahydro-2H-pyran-2-yl)-3-methylpenta-1,3-dienyl)-1,6-dioxaspiro[2.5]octan-5-yl)acetate, Compound 5

Part A:

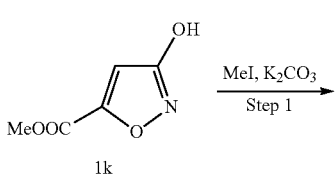

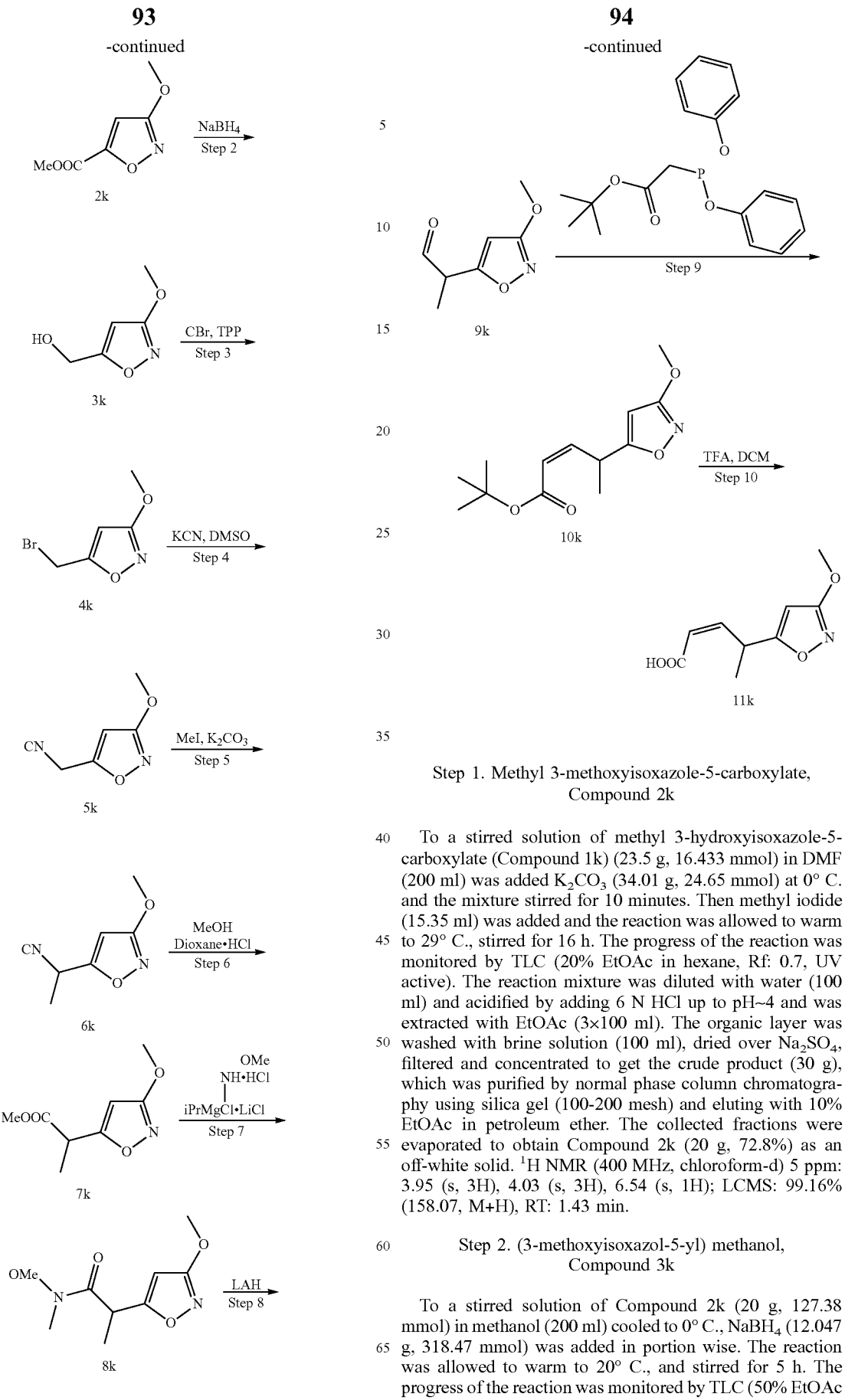

Step 1. Methyl 3-methoxyisoxazole-5-carboxylate, Compound 2k

To a stirred solution of methyl 3-hydroxyisoxazole-5-carboxylate (Compound 1k) (23.5 g, 16.433 mmol) in DMF (200 ml) was added $K_2CO_3$ (34.01 g, 24.65 mmol) at 0° C. and the mixture stirred for 10 minutes. Then methyl iodide (15.35 ml) was added and the reaction was allowed to warm to 29° C., stirred for 16 h. The progress of the reaction was monitored by TLC (20% EtOAc in hexane, Rf: 0.7, UV active). The reaction mixture was diluted with water (100 ml) and acidified by adding 6 N HCl up to pH~4 and was extracted with EtOAc (3×100 ml). The organic layer was washed with brine solution (100 ml), dried over $Na_2SO_4$, filtered and concentrated to get the crude product (30 g), which was purified by normal phase column chromatography using silica gel (100-200 mesh) and eluting with 10% EtOAc in petroleum ether. The collected fractions were evaporated to obtain Compound 2k (20 g, 72.8%) as an off-white solid. $^1$H NMR (400 MHz, chloroform-d) δ ppm: 3.95 (s, 3H), 4.03 (s, 3H), 6.54 (s, 1H); LCMS: 99.16% (158.07, M+H), RT: 1.43 min.

Step 2. (3-methoxyisoxazol-5-yl) methanol, Compound 3k

To a stirred solution of Compound 2k (20 g, 127.38 mmol) in methanol (200 ml) cooled to 0° C., $NaBH_4$ (12.047 g, 318.47 mmol) was added in portion wise. The reaction was allowed to warm to 20° C., and stirred for 5 h. The progress of the reaction was monitored by TLC (50% EtOAc in hexane, Rf: 0.3, PMA active). The reaction mixture was quenched with aqueous NH₄Cl (20 ml) at 0° C. The solvent was evaporated under reduced pressure at 30° C. to obtain a residue which was diluted in water (100 ml) and extracted with 10% MeOH in DCM (3×200 ml). The combined organic layers were washed with brine (100 ml), dried over Na₂SO₄, filtered and concentrated to obtain Compound 3k (13 g, 79%) as a pale yellow liquid. ¹H NMR (400 MHz, chloroform-d) δ ppm: 2.49 (s, 1H), 3.96 (s, 3H), 4.64 (d, J=5.70 Hz, 2H), 5.88 (s, 1H); LCMS: 98.84% (130.06, M+H), RT: 0.90 min.

Step 3. 5-(Bromomethyl)-3-methoxyisoxazole, Compound 4k

To a stirred solution of Compound 3k (13 g, 100.77 mmol) in DCM (200 ml), TPP (26.4 g, 100.77 mmol) and CBr₄ (33.42 g, 100 mmol) were added at 0° C., then the reaction mixture was allowed to warm to 25° C. and stirred for 2 h. The progress of the reaction was monitored by TLC (20% EtOAc in hexane, Rf: 0.8, UV active). The reaction mixture was washed with water (2×100 ml) and brine solution (100 ml). The organic layer was dried over Na₂SO₄, filtered and concentrated to obtain the crude product as a pale yellow liquid (23 g), which was purified by normal phase column chromatography using silica gel (100-200 mesh) and eluting with 10% EtOAc in petroleum ether as an eluent. The collected fractions were evaporated to obtain Compound 4k (15 g, 78%) as a pale yellow liquid. ¹H NMR (400 MHz, chloroform-d) δ ppm: 5.94 (s, 1H), 4.33 (s, 2H), 3.97 (S, 3H); LCMS: 92.15% (192.16, M+H), RT: 1.59 min.

Step 4. 2-(3-Methoxyisoxazol-5-yl)acetonitrile, Compound 5k

To a stirred solution of Compound 4k (15 g, 78.53 mmol) in DMSO (150 ml) and water (40 ml) was added KCN (7.65 g, 117.80 mmol) at 0° C., and the reaction was allowed to warm to 25° C. and was stirred for 3 h. The progress of the reaction was monitored by TLC (30% EtOAc in hexane, Rf: 0.3, iodine active). The reaction mixture was diluted with water (100 ml) and extracted with EtOAc (2×150 ml). The combined organic layers were washed with water (100 ml) and brine solution (100 ml), dried over Na₂SO₄ and concentrated under reduced pressure to obtain the crude compound (12 g), which was purified by normal phase column chromatography using silica gel (100-200 mesh) and eluting with 15% EtOAc in petroleum ether. The collected fractions were evaporated to obtain Compound 5k (6 g, 55%) as a pale yellow solid. ¹H NMR (400 MHz, chloroform-d) δ ppm: 6.00 (s, 1H), 3.98 (s, 3H), 3.79 (s, 2H); LCMS: 77.99% (138.92, M+H), RT: 1.54 min.

Step 5. 2-(3-Methoxyisoxazol-5-yl)propanenitrile, Compound 6k

To a suspension of Compound 5k (6 g, 43.478 mmol) in acetonitrile (60 ml) was added K₂CO₃ (6.6 g, 47.825 mmol) at 0° C. and the reaction was stirred for 20 min. Methyl iodide (16.22 ml, 260.86 mmol) in acetonitrile (20 ml) was added to the reaction at 0° C. After the addition, the reaction mixture was allowed to warm to 25° C., and stirred for 48 h. The progress of the reaction was monitored by TLC (30% EtOAc, RF=0.4, KMnO₄ active). After completion of the reaction, the mixture was filtered, the filtrate was diluted with EtOAc (150 ml) and washed with water (50 ml) and brine solution (50 ml). The organic layer was dried over Na₂SO₄ and concentrated under reduced pressure to obtain the crude compound (9 g), which was purified by normal phase column chromatography using silica gel (100-200 mesh) and eluting with 8% EtOAc in petroleum ether. The collected fractions were evaporated to obtain Compound 6k (3 g, 45%) as a pale yellow liquid. ¹H NMR (400 MHz, chloroform-d) δ ppm: 5.96 (s, 1H), 4.01 (m, 1H), 3.99 (s, 3H), 1.71 (d, 3H); LCMS: 85.72% (153.21, M+H), RT: 1.43 min.

Step 6. Methyl 2-(3-methoxyisoxazol-5-yl)propanoate, Compound 7k

To a solution of Compound 6k (3 g, 19.736 mmol) in MeOH (20 ml) was added 4.0 M HCl in 1,4-dioxane (20 ml) in a 100-ml sealed tube, which was heated to 70° C. and stirred for 24 h. The progress of the reaction was monitored by TLC (30% EtOAc in hexane, RF=0.6, PMA active). After completion of reaction, the reaction mixture was concentrated, and the residue was taken up in EtOAc (100 ml) and washed with NaHCO₃ solution (2×50 ml), water (50 ml), and brine solution (50 ml). The organic layer was dried over Na₂SO₄ and concentrated under reduced pressure to obtain the crude compound (3.5 g), which was purified by normal phase column chromatography using silica gel (100-200 mesh), eluting with 5% EtOAc in petroleum ether. The collected fractions were evaporated to obtain Compound 7k (3 g, 83%) as a pale yellow gum. ¹H NMR (400 MHz, chloroform-d) δ ppm: 5.80 (s, 1H), 3.95 (s, 3H), 3.82 (m, 1H), 3.73 (s, 3H), 1.55 (d, 3H); LCMS: 94.48% (186.22, M+H), RT: 1.54 min.

Step 7. N-Methoxy-2-(3-methoxyisoxazol-5-yl)-N-methylpropanamide, Compound 8k To a stirred solution of Compound 7k (3 g, 16.216 mmol) and N,O-dimethyl hydroxylamine hydrochloride (3.16 g, 32.43 mmol) in THF (50 ml) was added isopropyl magnesium chloride lithium chloride complex (37.42 ml, 48.648 mmol) at 0° C. After the addition, the reaction mixture was stirred for 3 h at room temperature. The progress of the reaction was monitored by TLC (50% EtOAc, RF=0.3, PMA active). After completion, the reaction mixture was quenched with saturated ammonium chloride solution at 0° C. and extracted with ethyl acetate (3×100 ml). The combined organic layers were dried over sodium sulfate and concentrated under reduced pressure to obtain the crude product (5 g), which was purified by normal phase column chromatography using silica gel (100-200 mesh), eluting with 20% EtOAc in petroleum ether. The collected fractions were evaporated to obtain Compound 8k (2.1 g, 60%) as a pale yellow liquid. ¹H NMR (400 MHz, chloroform-d) δ ppm: 5.80 (s, 1H), 4.31 (m, 1H), 3.94 (s, 3H), 3.68 (s, 3H), 3.21 (s, 3H), 1.47 (d, 3H); LCMS: 97.22% (215.23, M+H), RT: 1.40 min.

Step 8. 2-(3-methoxyisoxazol-5-yl)propanal, Compound 9k

To a stirred solution of Compound 8k (1.8 g, 8.411 mmol) in THF (30 ml) was added LAH (4.2 ml, 8.411 mmol, 2 M in THF) at −78° C. and the mixture was stirred for 30 minutes at −78° C. The progress of the reaction was monitored by TLC (30% EtOAc, RF=0.4, 2, 4-DNP active). After completion of the reaction, it was quenched with sodium sulfate slurry, and stirred for 30 min at room temperature.

The un-dissolved solids were filtered and washed with ethyl acetate (50 ml). The filtrate was dried with sodium sulfate and evaporated under reduced pressure to afford Compound 9k (1.1 g). The crude product was used for next step without purification. The presence of an aldehyde compound was confirmed by $^1$H NMR.

Step 9. (Z)-tert-Butyl 4-(3-methoxyisoxazol-5-yl)pent-2-enoate, Compound 10k To a stirred solution of 18-crown-6 (19.18 g, 72.58 mmol) and tert-butyl 2-(diphenoxyphosphino) acetate (4.61 g, 14.51 mmol) in THF (50 ml) was added LiHMDS (14.51 ml, 14.51 mmol, 1 M in THF) dropwise at −78° C. After the addition, the reaction mixture was stirred at −78° C. for 40 min. Then Compound 9k (1.1 g, 14.51 mmol) in THF (10 ml) was added to the reaction mixture at −78° C. After the addition, the reaction mixture was stirred for 2 h at room temperature. The progress of the reaction was monitored by TLC (20% EtOAc in hexane, RF=0.7, PMA active). After completion of the reaction, it was quenched with saturated ammonium chloride solution, extracted with ethyl acetate (3×100 ml) and dried with sodium sulfate. The solvent was evaporated under reduced pressure to obtain the crude product (3 g), which was purified by silica column using a 2% EtOAc in hexane gradient. The pure fractions were collected and evaporated under reduced pressure to Compound 10k (350 mg, 19%) as a yellow liquid. $^1$H NMR (400 MHz, chloroform-d) δ ppm: 1.40 (d, J=7.02 Hz, 3H), 1.45-1.52 (m, 9H), 3.94 (s, 3H), 4.87-4.97 (m, 1H), 5.64 (s, 1H), 5.77 (d, J=11.40 Hz, 1H), 6.10 (dd, J=11.18, 9.87 Hz, 1H); LCMS: 91.94% (254.31, M+H), RT: 2.60 min.

Step 10. (Z)-4-(3-Methoxyisoxazol-5-yl)pent-2-enoic acid, Compound 11k

To a stirred solution of Compound 10k (350 mg, 1.383 mmol) in DCM (35 ml) was added TFA (3.17 ml, 41.50 mmol) at 29° C. and the mixture stirred for 6 h. The progress of the reaction was monitored by TLC (30% EtOAc in petroleum ether, RF=0.2, UV active). After completion of the reaction, the solvent was evaporated at 25° C. under reduced pressure to obtain the crude product. The crude compound was washed with n-pentane (2×10 ml) and the solid residue was dried under reduced pressure to obtain Compound 11k (202 mg, 87%) as off-white solid. JJ constant coupling value confirmed formation of Z geometric isomer. $^1$H NMR (400 MHz, DMSO-d$_6$) δ ppm: 12.62 (br, 1H), 6.25 (dd, J=11.18, 9.87 Hz, 1H), 6.06 (s, 1H), 5.87 (d, J=11.40 Hz, 1H), 4.80-4.91 (m, 1H), 3.86 (s, 3H), 1.32 (d, J=7.02 Hz, 3H); LCMS: 90.09% (198.24, M+H), RT: 2.54 min.

Part B:

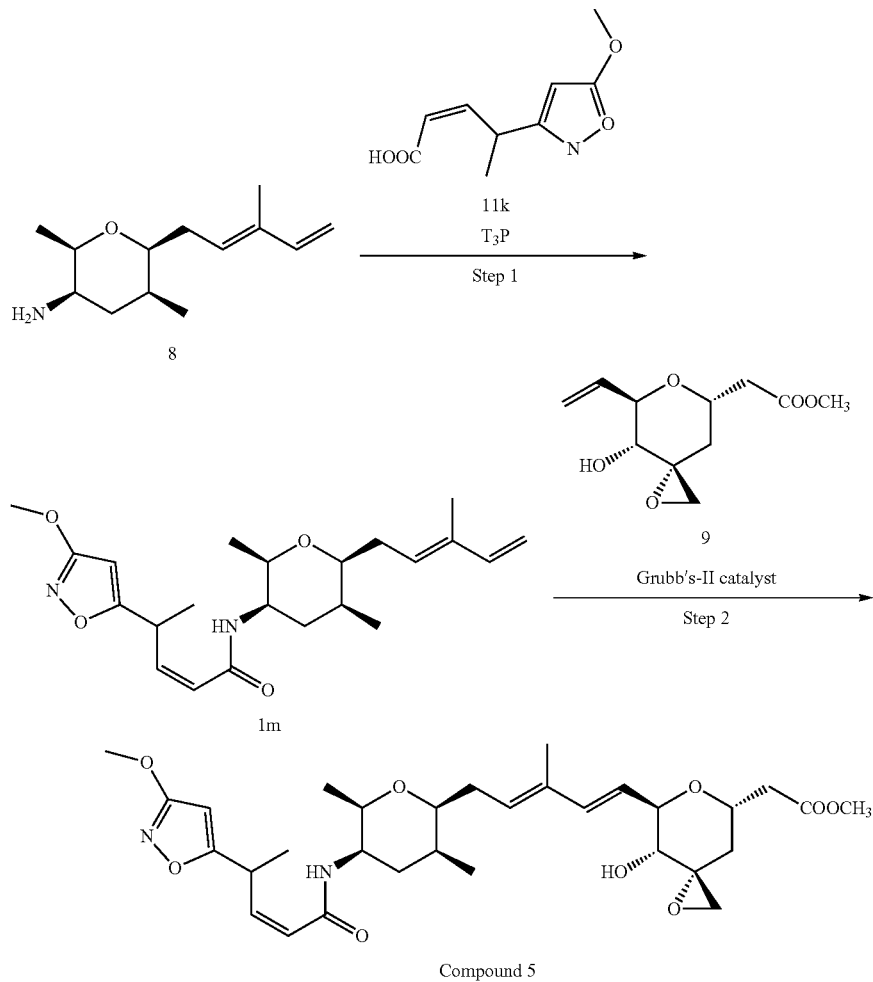

Compound 5

Step 1. (Z)—N-((2R, 3R, 5S, 6S)-2,5-dimethyl-6-((E)-3-methylpenta-2,4-dienyl)tetrahydro-2H-pyran-3-yl)-4-(3-methoxyisoxazol-5-yl)pent-2-enamide, Compound 1m To a stirred solution of Compound 8 (300 mg, 1.435 mmol), Compound 11k (170 mg, 0.861 mmol) in THF (10 mL), DIPEA (925 mg, 7.175 mmol) and T$_3$P (50% in EtOAc) (1.36 g, 4.305 mmol) were added at room temperature. The reaction mixture was stirred at room temperature for 4 h. The reaction progress was monitored by TLC (20% EtOAc in petroleum ether, RF=0.5, UV active). The reaction solvent was concentrated under reduced pressure to obtain the crude product. The crude product was purified by column chromatography (100-200 silica gel/eluent 10% EtOAc in petroleum ether) to give Compound 1m (90 mg, 16%) as a colorless gum. $^1$H NMR (400 MHz, chloroform-d) δ ppm 6.37 (dd, J=17.61, 10.76 Hz, 1H) 5.97-6.07 (m, 1H) 5.70-5.81 (m, 2H) 5.66 (s, 1H) 5.46 (br t, J=7.09 Hz, 1H) 5.07-5.22 (m, 2H) 4.96 (d, J=10.76 Hz, 1H) 3.94 (d, J=1.96 Hz, 4H) 3.68 (q, J=6.68 Hz, 1H) 3.55 (td, J=7.21, 2.69 Hz, 1H) 2.34-2.46 (m, 1H) 2.25 (dt, J=15.16, 7.58 Hz, 1H) 1.95 (q, J=3.42 Hz, 2H) 1.78-1.85 (m, 1H) 1.76 (s, 3H) 1.41 (dd, J=6.85, 1.96 Hz, 3H) 1.21-1.30 (m, 2H) 1.15 (t, J=6.36 Hz, 3H) 1.02 (t, J=7.34 Hz, 3H); LCMS: 85.73% (389.36, M+H), RT: 2.71 and 2.74 min.

Step 2. Methyl 2-((3R, 5S, 7R, 8R)-8-hydroxy-7-((1E, 3E)-5-((2S, 3S, 5R, 6R)-5-((Z)-4-(3-methoxy-isoxazol-5-yl)pent-2-enamido)-3,6-dimethyltetrahydro-2H-pyran-2-yl)-3-methylpenta-1,3-dienyl)-1,6-dioxaspiro[2.5]octan-5-yl)acetate, Compound 5

To a stirred solution of Compound 1m (77 mg, 0.198 mmol) and Compound 9 (77 mg, 0.337 mmol) in DCM (8 ml) was added Grubbs-II catalyst (50 mg, 0.059 mmol) at room temperature under argon atmosphere. The reaction mixture was stirred at 40° C. for 5 h. The reaction progress was monitored by TLC (50% EtOAc in petroleum ether, RF=0.1, UV active). The reaction mixture was filtered through a celite pad and washed with DCM (2 ml). The solvent was concentrated under reduced pressure to obtain the crude product. The crude product was purified by preparative HPLC [Mobile Phase A: 10 mm ABC; Mobile phase B: acetonitrile; Column: X-Bridge (150×19) mm, 5u; Column: Method: (T/% B): 0/30, 2/30, 20/30.20/60, 20.5, 90, 22/90; Flow. 18 ml/min; Solubility: ACN+THF+water; Ambient temperature]. The combined fractions were lyophilized to obtain pure product Compound 5 (7.5 mg, 6.4%) as an off-white solid. $^1$H NMR (400 MHz, chloroform-d) δ ppm 6.37 (d, J=15.78 Hz, 1H) 6.02 (ddd, J=11.18, 9.76, 2.52 Hz, 1H) 5.68-5.80 (m, 2H) 5.57-5.67 (m, 2H) 5.51 (br t, J=7.13 Hz, 1H) 5.06-5.22 (m, 1H) 4.43-4.55 (m, 1H) 4.20 (br t, J=6.69 Hz, 1H) 3.94 (d, J=1.75 Hz, 4H) 3.61-3.73 (m, 4H) 3.46-3.57 (m, 2H) 2.87-3.02 (m, 2H) 2.60-2.74 (m, 2H) 2.33-2.48 (m, 2H) 2.20-2.32 (m, 2H) 2.16 (dd, J=13.81, 5.48 Hz, 1H) 1.90-1.98 (m, 2H) 1.71-1.85 (m, 6H) 1.41 (dd, J=7.02, 1.97 Hz, 3H) 1.14 (t, J=6.36 Hz, 3H) 1.01 (t, J=7.34 Hz, 3H); LCMS: 90.65% (589.11, M+H), RT: 3.95, 4.01 min.

Example 6

Synthesis of Methyl 2-((3R, 5S, 7R, 8R)-7-((1E, 3E)-5-((2S, 3S, 5R, 6R)-3,6-dimethyl-5-((Z)-4-(5-methyl-1,2,4-oxadiazol-3-yl)pent-2-enamido)tetrahydro-2H-pyran-2-yl)-3-methylpenta-1,3-dienyl)-8-hydroxy-1,6-dioxaspiro[2.5]octan-5-yl)acetate, Compound 6

Part A:

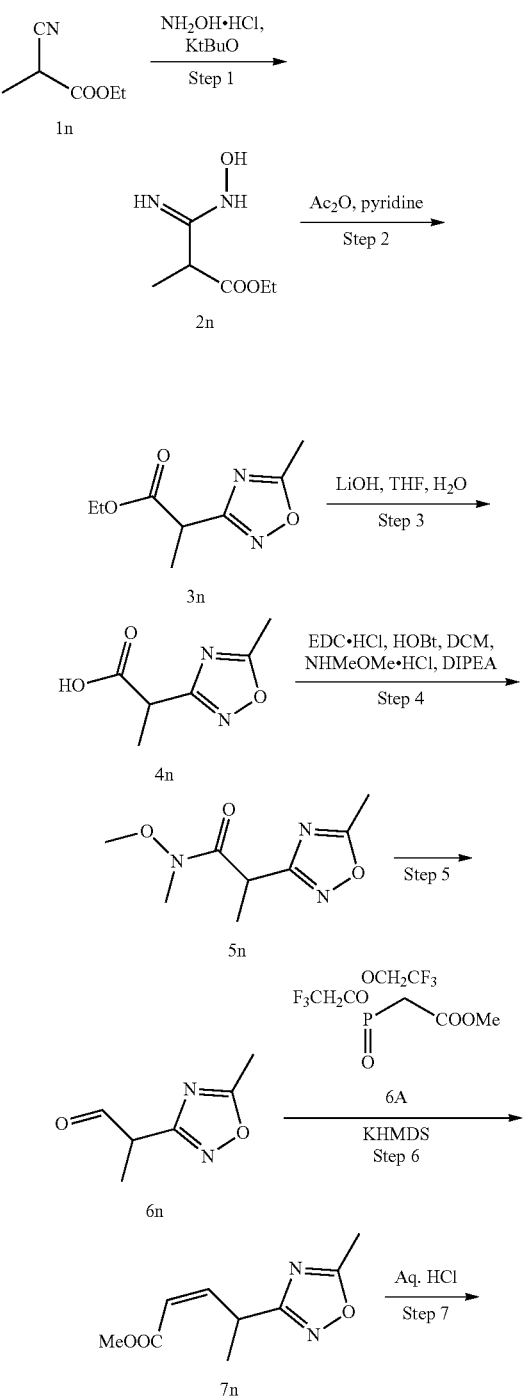

-continued

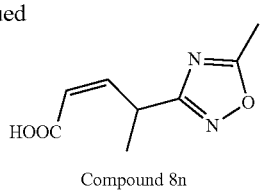

Compound 8n

Step 1. Ethyl 3-(hydroxyl amino)-3-imino-2-methylpropanoate, Compound 2n

To a stirred solution of ethyl 2-cyanopropanoate (Compound 1n) (20 g, 15.7 mmol) in THF (500 ml) was added a solution of KOtBu (314 ml, 31.4 mmol, 1 M in THF) at 0° C. After 10 min, hydroxyl amine hydrochloride (27 g, 39.3 mmol) was added and the reaction mixture was stirred at room temperature for 48 h. The progress of the reaction was monitored by TLC (50% EtOAc in hexane, Rf: 0.1, $KMnO_4$ active). The reaction mixture was evaporated under reduced pressure, and the residue was purified by silica column using 40% ethyl acetate in hexane as an eluent. The pure fractions were collected and evaporated under reduced pressure to obtain Compound 2n (5.5 g, 21.8%) as colorless oil. $^1H$ NMR (400 MHz, DMSO-$d_6$) δ ppm 1.17 (t, J=7.15 Hz, 3H), 1.24 (d, J=7.15 Hz, 3H), 3.10-3.20 (m, 1H), 3.92-4.23 (q, 2H), 5.31-5.45 (br, 2H); LCMS: 43.4% (161.13, M+H), RT=0.37 min. and 49.48% (161.13, M+H), RT=0.41 min.

Step 2. Ethyl 2-(5-methyl-1, 2, 4-oxadiazol-3-yl) propanoate, Compound 3n

To a stirred solution of Compound 2n (5.5 g, 34.3 mmol) in pyridine (50 ml) was added acetic anhydride (9.7 ml, 10.3 mmol) in a sealed tube at room temperature. The reaction mixture was heated at 120° C. for 24 h. The progress of the reaction was monitored by TLC (50% EtOAc in hexane, Rf: 0.5, $KMnO_4$ active). The reaction mixture was evaporated under reduced pressure, and the residue was purified by silica column using 20% ethyl acetate in hexane as an eluent. The pure fractions were collected and evaporated under reduced pressure to obtain Compound 3n (4.5 g, 71.4%) as a yellow oil. $^1H$ NMR (400 MHz, chloroform-d) δ ppm 1.26 (t, J=7.09 Hz, 3H), 1.58-1.62 (d, 3H), 2.61 (s, 3H), 3.89-4.00 (q, 1H), 4.15-4.26 (q, 2H); LCMS: 86.56% (185.22, M+H), RT=1.48 min.

Step 3. 2-(5-Methyl-1, 2, 4-oxadiazol-3-yl) propanoic acid, Compound 4n

To a stirred solution of Compound 3n (4.5 g, 24.4 mmol) in MeOH:THF:$H_2O$ (45 ml, 4:4:1) was added LiOH.$H_2O$ (4 g, 9.7 mmol) at 0° C. and the reaction mixture was stirred at room temperature for 12 h. The progress of the reaction was monitored by TLC (50% EtOAc in hexane, Rf: 0.1, $KMnO_4$ active). The reaction mixture was evaporated under reduced pressure, the pH of residue was adjusted ~1 using 6N HCl (~10 ml), and then extracted with ethyl acetate (25 ml×2). The combined organic layer was dried using $Na_2SO_4$ and concentrated under reduced pressure to obtain Compound 4n (3.5 g, 92%) as a colorless oil. $^1H$ NMR (400 MHz, DMSO-$d_6$) δ ppm 1.41 (d, J=7.23 Hz, 3H), 2.57 (s, 3H), 3.88-3.97 (q, 1H), 12.65-12.82 (br s, 1H); LCMS: 94.38% (157.1, M+H), RT=1.05 min.

Step 4. N-methoxy-N-methyl-2-(5-methyl-1, 2, 4-oxadiazol-3-yl) propanamide, Compound 5n To a stirred solution of Compound 4n (3.5 g, 22.4 mmol) in DCM (100 ml), EDC-HCl (6.4 g, 33.6 mmol), HOBt (4.5 g, 33.6 mmol) and DIPEA (11.7 ml, 67.2 mmol) were added at 0° C. After 10 min, N,O-dimethyl hydroxyl amine hydrochloride (3.2 g, 33.6 mol) was added at 0° C. The reaction mixture was stirred at room temperature for 12 h. The progress of the reaction was monitored by TLC (50% EtOAc in hexane, Rf: 0.2, $KMnO_4$ active). The reaction mixture was diluted with DCM (40 ml) and washed with saturated solution of sodium bicarbonate (30 ml). The organic layer was separated and dried over sodium sulfate. The organic layer was evaporated under reduced pressure and 5 g of crude Compound 5n was obtained. The crude compound was purified by silica column using 40% ethyl acetate in hexane as an eluent. The pure fractions were collected and evaporated under reduced pressure to obtain Compound 5n (2.2 g, 50%) as a colorless oil. $^1H$ NMR (400 MHz, chloroform-d) δ ppm 1.57 (d, J=7.03 Hz, 3H), 2.60 (s, 3H), 3.26 (s, 3H), 3.72 (s, 3H), 4.34-4.42 (q, 1H); LCMS: 96.65% (200.16, M+H), RT=1.21 min.

Step 5. 2-(5-Methyl-1, 2, 4-oxadiazol-3-yl) propanal, Compound 6n

To a stirred solution of LAH (380 mg, 10 mmol) in THF (10 ml) was added Compound 5n (1 g, 50 mmol) in THF (20 ml) slowly at 0° C. The reaction mixture was stirred at room temperature for 1 h. The progress of the reaction was monitored by TLC (40% EtOAc in hexane, Rf: 0.3, $KMnO_4$ active and 2, 4-DNP slightly active). The reaction mixture was quenched using 1 N HCl (~3 ml) at 0° C. and stirred for 10 min and then ethyl acetate (20 ml) was added. The reaction mixture was filtered through a celite bed. The filtrate was dried using sodium sulfate and the volume minimized to 4 ml (~800 mg, crude) of Compound 6n. Compound 6n was used without further purification for Step 6. ESMS: 40.4% (141.1, M+H), RT=2.24 min (crude); Note: $^1H$ NMR did not provide a readable spectrum.

Step 6. Methyl (Z)-4-(5-methyl-1, 2, 4-oxadiazol-3-yl) pent-2-enoate, Compound 7n To a stirred solution of 18-crown-6-ether (7.5 g, 28.5 m mol) in dry THF (30 ml) was added methyl 2-(bis(2,2,2-trifluoroethoxy) phosphoryl) acetate (1.3 ml, 6.2 m mol) at 0° C. followed by 1 M KHMDS in THF (6.2 ml, 6.2 mmol) at −78° C. The reaction mixture maintained at −78° C. for 30 min, then Compound 6n (~800 mg) in dry THF (10 ml) was added at −78° C. The reaction mixture was allowed to warm to room temperature gradually and was stirred at same temperature for 2 h. The progress of the reaction was monitored by TLC (30% EtOAc in hexane, Rf: 0.5, $KMnO_4$ active). The reaction mixture was quenched using $H_2O$ (30 ml) and extracted in ethyl acetate (50 ml×2). The combined organic layers were dried over sodium sulfate and concentrated under reduced pressure to obtain 600 mg of crude Compound 7n. The crude compound was purified by silica column using 10% ethyl acetate in hexane as an eluent. The pure fractions were collected and evaporated under reduced pressure to obtain Compound 7n (420 mg, 59% pure by LCMS, 37%) as yellow colored oil. $^1H$ NMR (400 MHz, chloroform-d) δ ppm 1.44-1.48 (d, 3H), 2.57 (s, 3H) 3.74 (s, 3H), 5.01-5.10 (q, 1H), 5.92-5.89 (d, J=10 Hz, 1H), 6.35-6.46 (dd, J=10 Hz, 1H); LCMS: 59% (197.21, M+H), RT=1.57 min. Z geometric isomer confirm by JJ coupling constant value of olefin bond: 10 Hz.

Step 7. (Z)-4-(5-methyl-1, 2, 4-oxadiazol-3-yl)pent-2-enoic acid, Compound 8n Compound 7n (550 mg, 28 mmol, 80% pure by LCMS) was added in dioxane (10 ml) and 2 N HCl (5 ml). The reaction mixture was heated at 55° C. for 48 h. The progress of the reaction was monitored by TLC (30% EtOAc in hexane, Rf: 0.1, KMnO$_4$ active). The reaction mixture was concentrated under reduced pressure and purified using preparative HPLC to obtain pure Compound 8n (138 mg, 28.6%) as a colorless oil. $^1$H NMR (400 MHz, DMSO-d$_6$) δ ppm 1.33 (d, J=7.02 Hz, 3H), 2.55 (s, 3H), 4.86-5.08 (q, 1H), 5.84 (dd, J=11.40 Hz, 1H), 6.24 (m, J=10.52 Hz, 1H), 11.64-12.96 (br s, 1H); LCMS: 98.59% (183.21, M+H), RT=1.4 min.

Part B:

(50% in EtOAc) (0.68 ml, 1.431 mmol). The reaction mixture was stirred at 23° C. for 3 h. The reaction progress was monitored by TLC (50% EtOAc in hexane, R$_f$=0.6, UV visible). After completion, the reaction mixture was concentrated in vacuo to obtain the crude compound. The crude residue was purified by flash chromatography (10 to 50% EtOAc in hexanes) on silica (100-200 mesh) to afford Compound 1p (130 mg, 48.68%) as a pale yellow liquid. $^1$H NMR (400 MHz, chloroform-d) δ ppm 6.45-6.33 (m, 1H) 6.17-6.12 (m, 1H) 6.07-6.01 (m, 1H) 5.85-5.79 (m, 1H) 5.46-5.45 (m, 1H) 5.13-5.09 (m, 1H) 4.97-4.88 (m, 1H) 3.96 (br, 1H) 3.68-3.66 (m, 1H) 3.55-3.52 (m, 1H) 2.56 9s, 3H) 2.39-2.35 (m, 1H) 2.27-2.21 (m, 1H) 2.04-1.98 (m, 1H) 1.93-1.90 (m, 2H) 1.82-1.76 (m, 3H) 1.49-1.46 (m, 3H) 1.28-1.21 (m 5H) 1.16-1.10 (m, 3H) 1.06-0.97 (m, 3H); LCMS: 85.98% (374.42, M+H), RT: 2.61 min and 2.63 min.

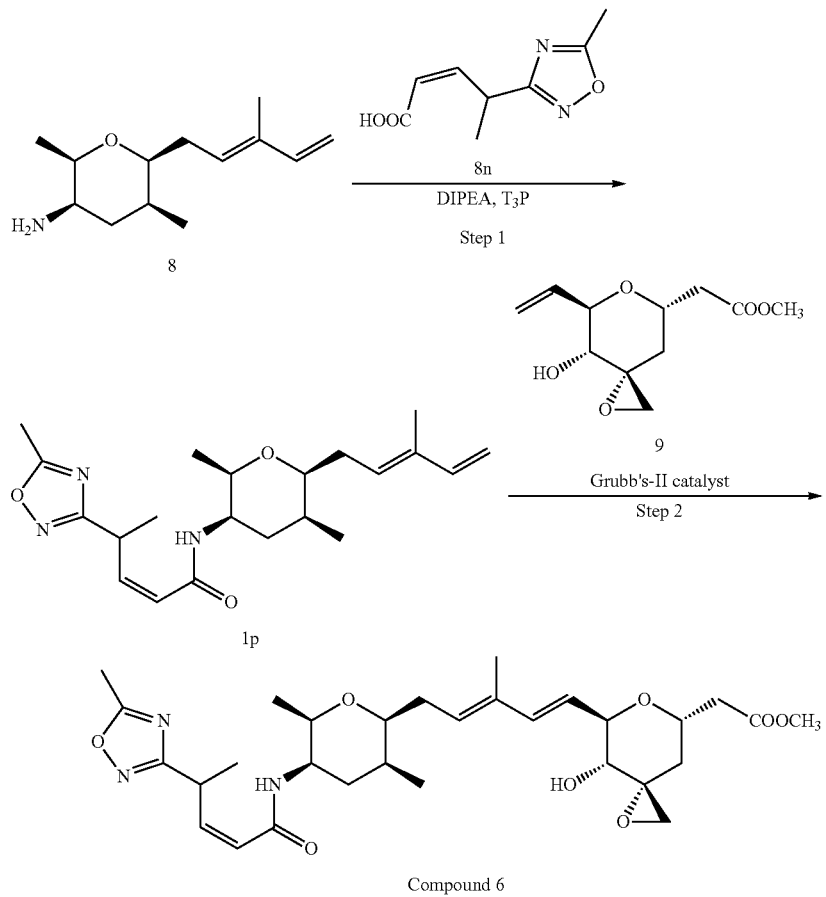

Compound 6

Step-1. (Z)—N-((2R, 3R, 5S, 6S)-2,5-dimethyl-6-((E)-3-methylpenta-2,4-dienyl)tetrahydro-2H-pyran-3-yl)-4-(5-methyl-1,2,4-oxadiazol-3-yl)pent-2-enamide, Compound 1p To a stirred solution of Compound 8 (150 mg, 0.716 mmol), Compound 8n (130 mg, 0.716 mmol) in THF (5 ml) at 23° C., was added DIPEA (0.65 ml, 2.385 mmol) and T$_3$P

Step 2. Methyl 2-((3R, 5S, 7R, 8R)-7-((1E, 3E)-5-((2S, 3S, 5R, 6R)-3,6-dimethyl-5-((Z)-4-(5-methyl-1,2,4-oxadiazol-3-yl)pent-2-enamido)tetrahydro-2H-pyran-2-yl)-3-methylpenta-1,3-dienyl)-8-hydroxy-1,6-dioxaspiro[2.5]octan-5-yl)acetate, Compound 6

To a stirred solution of Compound 1p (120 mg, 0.321 mmol) in DCM (10 ml) at 23° C., Compound 9 (109 mg, 0.481 mmol) and Grubbs-II catalyst (81 mg, 0.096 mmol) were added under a nitrogen atmosphere. The reaction mixture was stirred at 40° C. for 5 h. The reaction progress was monitored by TLC (50% EtOAc in hexanes, $R_F$=0.1, UV visible). The reaction mixture was filtered through celite, washed with DCM (5 ml) and the filtrate was concentrated under reduced pressure to obtain the crude compound. The crude residue was purified by preparative HPLC [Mobile Phase A: 10 mm ABC; Mobile Phase B: acetonitrile; Column: X-bridge (150×19) mm, 5u; Method: (T/% B): 0/30, 2/30, 20/60, 20.50/90, 22/90; Flow: 18 ml/min; Solubility: ACN+THF+Water; Ambient temperature]. The collected fractions were lyophilized to afford Compound 6 (5 mg) as a white solid. $^1$H NMR (400 MHz, chloroform-d) δ ppm 6.31-6.44 (m, 1H) 5.99-6.19 (m, 2H) 5.77-5.89 (m, 1H) 5.63 (br dd, J=15.89, 6.25 Hz, 1H) 5.45-5.56 (m, 1H) 5.02-5.17 (m, 1H) 4.83-4.96 (m, 1H) 4.44-4.54 (m, 1H) 4.20 (br t, J=6.69 Hz, 1H) 3.90-4.02 (m, 1H) 3.61-3.77 (m, 4H) 3.44-3.58 (m, 3H) 2.88-3.02 (m, 2H) 2.61-2.76 (m, 2H) 2.56 (s, 3H) 2.38 (td, J=14.85, 7.34 Hz, 1H) 2.12-2.29 (m, 2H) 1.87-2.04 (m, 3H) 1.70-1.84 (m, 5H) 1.48 (dd, J=6.91, 4.71 Hz, 3H) 1.08-1.20 (m, 3H) 0.94-1.07 (m, 3H); LCMS: 96.43% (574.15, M+H), RT: 3.59 min and 3.64 min.

Example 7

Synthesis of Methyl 2-((3R, 5S, 7R, 8R)-7-((1E, 3E)-5-((2S, 3S, 5R, 6R)-3,6-dimethyl-5-((Z)-4-methyl-5-((3-methyloxetan-3-yl)oxy)pent-2-enamido)tetrahydro-2H-pyran-2-yl)-3-methylpenta-1,3-dien-1-yl)-8-hydroxy-1,6-dioxaspiro[2.5]octan-5-yl) acetate, Compound 7

Part A:

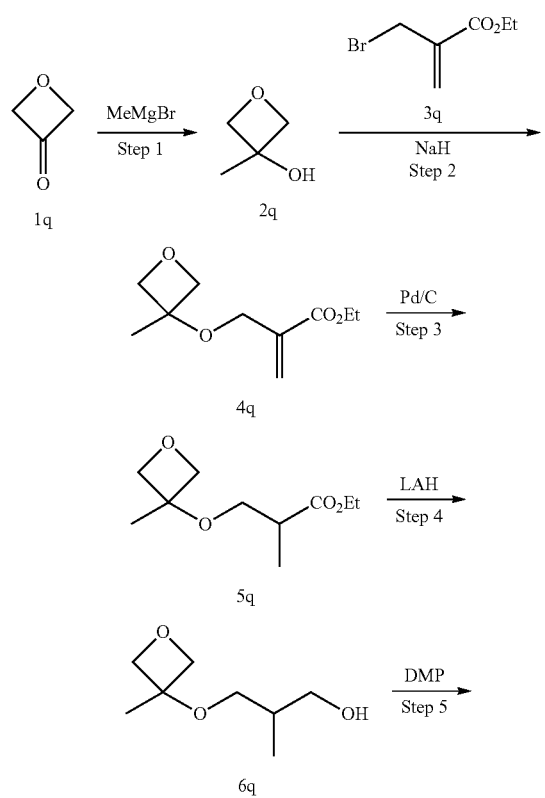

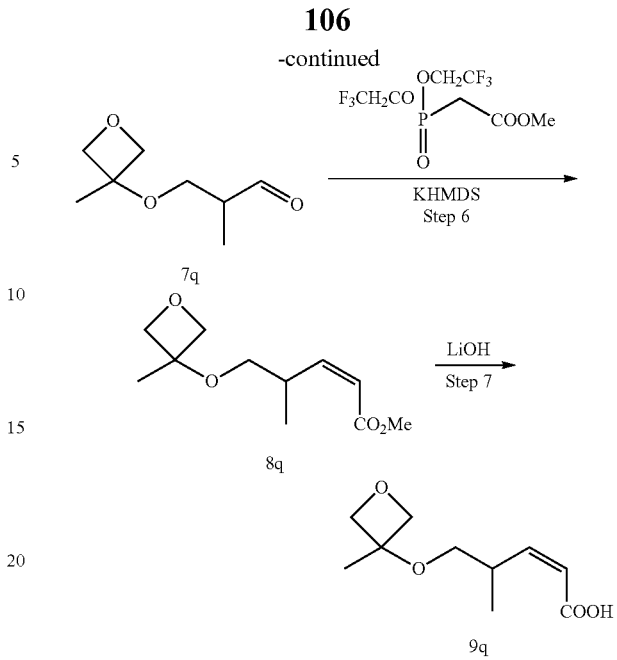

Step 1. 3-Methyloxetan-3-ol, Compound 2q

To a stirred solution of oxetan-3-one (Compound 2q) (25 g, 346.9 mmol) in dry diethyl ether (1.25 l) was added dropwise 3 M methyl magnesium bromide in diethyl ether (127.2 mL, 381.6 mmol) at 0° C. over a period of 2 h. The reaction mass was stirred at 0° C. for 2 h. The progress of the reaction was monitored by TLC (40% EtOAc in hexane, Rf: 0.2, PMA active). The reaction mass was quenched using sat. NH$_4$Cl solution (~1 L) at 0° C. slowly over a period of 1 h. The organic layer was separated and again aqueous layer was extracted with 10% MeOH in DCM (200 ml×5). The combined organic layer was dried over anhydrous Na$_2$SO$_4$ and evaporated under reduced pressure at 20° C. to obtain Compound 2q (16 g, 52%) as an orange-colored oil. $^1$H NMR (400 MHz, DMSO-d$_6$) δ ppm 1.38-1.40 (s, 3H) 4.26 (d, J=6.58 Hz, 2H), 4.43 (d, J=5.92 Hz, 2H), 5.50 (s, 1H); GCMS=98.87%.

Step 2. Ethyl 2-(((3-methyloxetan-3-yl) oxy) methyl) acrylate, Compound 4q

To a stirred solution of Compound 2q (10.5 g, 119.16 mmol) in DMF (120 mL) was added portion wise NaH (5.72 g, 238.33 mmol) at 0° C. The reaction mixture was stirred at 0° C. for 30 min followed by addition of Compound 3q (23 g, 119.16 mmol) at 0° C. and stirring at room temperature for 2 h. The progress of the reaction was monitored by TLC (10% EtOAc in hexane, Rf: 0.5, UV and PMA active). The reaction mixture was quenched using ice cold water (120 ml) and extracted using diethyl ether (100 ml×3). The combined organic layers were washed with cold water (100 ml×3). The organic layer was separated and dried over anhydrous sodium sulfate. The organic layer was evaporated under reduced pressure, and the residue was purified by silica column using 10% ethyl acetate in hexane as an eluent. The pure fractions were collected and evaporated under reduced pressure to obtain Compound 4q (7 g, 29%) as a colorless oil. $^1$H NMR (400 MHz, chloroform-d) δ ppm 1.29-1.34 (t, 3H) 1.58-1.60 (s, 3H), 4.13 (s, J=1.67 Hz, 2H), 4.20-4.27 (q, 2H), 4.37-4.40 (d, 2H), 4.73 (d, J=6.32 Hz, 2H), 5.93 (s, 1H) 6.32 (s, J=1.55 Hz, 1H); LCMS: 71.79% (201.23, M+H), RT=1.57 min.

Step 3. Ethyl 2-methyl-3-((3-methyloxetan-3-yl) oxy) propanoate, Compound 5q To a stirred solution of Compound 4q (7 g, 35 mmol) in ethanol (100 mL) was added 10% Pd/C (2 g) under nitrogen. The reaction mixture was stirred at room temperature for 48 h under hydrogen atmosphere using a hydrogen bladder (~20 psi). The progress of the reaction was monitored by TLC (10% EtOAc in Hexane, Rf: 0.5, PMA active). The reaction mixture was filtered through a celite bed and washed with ethyl acetate (200 ml×2). The reaction mixture was evaporated under reduced pressure to obtain Compound 5q (6 g, 84%) as a colorless oil. $^1$H NMR (400 MHz, DMSO-d$_6$) δ ppm 0.99-1.13 (d, 3H), 1.14-1.26 (t, 3H), 1.32-1.44 (s, 3H), 2.57-2.67 (m, 1H), 3.34-3.47 (m, 2H), 4.00-4.14 (q, 2H), 4.22-4.28 (d, 2H), 4.40-4.48 (m, 2H); LCMS: 85.89% (203.2, M+H), RT=2.72 min.

Step 4. 2-Methyl-3-((3-methyloxetan-3-yl) oxy) propan-1-ol, Compound 6q

To a stirred solution of Compound 5 q (1 g, 4.95 mmol) in dry THF (10 mL) was added LAH (282 mg, 7.42 mmol) at 0° C. and the mixture stirred at room temperature for 16 h. The progress of the reaction was monitored by TLC (30% EtOAc in Hexane, Rf: 0.2, KMnO$_4$ active). The reaction mixture was quenched using ice cold water (20 ml) at 0° C. and stirred at room temperature for 1 h. The reaction mixture was filtered through a celite bed and washed with 10% MeOH in DCM (20 ml×5). The product was extracted from the mother liquor using 10% MeOH in DCM (20 ml×7). The organic layer was separated and dried over anhydrous sodium sulfate followed by evaporation under reduced pressure to obtain crude Compound 6q (700 mg, 88%) as a colorless oil. $^1$H NMR (400 MHz, DMSO-d$_6$) δ ppm 0.86 (d, J=6.80 Hz, 3H), 1.43 (s, 3H), 1.66-1.76 (m, 1H), 3.11-3.39 (m, 5H), 4.23-4.26 (d, 2H), 4.37-4.41 (t, 1H), 4.46-4.50 (d, 2H).

Step 5. 2-Methyl-3-((3-methyloxetan-3-yl) oxy) propanal, Compound 7q

To a stirred solution of Compound 6q (500 mg, 3.12 mmol) in DCM (10 mL) was added Dess-Martin periodinane (DMP) (1.72 g, 4.06 mmol) at 0° C., stirred at room temperature for 2 h. The progress of the reaction was monitored by TLC (30% EtOAc in hexane, Rf: 0.6, 2, 4-DNP and KMnO$_4$ active). The reaction mixture was quenched using sat. NaHCO$_3$ solution (~20 ml) and filtered through a celite bed and washed with dichloromethane (30 ml×2). The product was extracted from the mother liquor using dichloromethane (20 ml×2). The combined organic layers were separated, dried over Na$_2$SO$_4$ and evaporated under reduced pressure. The residue was purified by a silica column using 15% ethyl acetate in hexane as an eluent. The pure fractions were collected and evaporated under reduced pressure to obtain Compound 7q (270 mg, 54%) as a colorless gummy compound. $^1$H NMR (400 MHz, chloroform-d) δ ppm 1.17 (d, J=7.19 Hz, 3H), 1.54 (s, 3H), 2.48-2.71 (m, 1H), 3.44-3.62 (m, 2H), 4.35 (d, J=6.54 Hz, 2H), 4.57-4.75 (d, 2H), 9.60-9.80 (s, 1H).

Step 6. Methyl (Z)-4-methyl-5-((3-methyloxetan-3-yl) oxy) pent-2-enoate, Compound 8q To a stirred solution of 18-crown-6-ether (2.27 g, 8.54 mmol) in dry THF (10 ml) was added methyl 2-(bis (2,2, 2-trifluoroethoxy) phosphoryl) acetate (597 mg, 1.87 mmol) at 0° C. followed by addition of 1 M KHMDS in THF (1.7 ml, 1.70 mmol) at −78° C. The reaction mixture was maintained at −78° C. for 30 min then added Compound 7q (270 mg, 1.70 mmol) in dry THF (5 ml) at −78° C. and the reaction mixture was allowed to warm to room temperature gradually in 1.5 h. The progress of the reaction was monitored by TLC (20% EtOAc in hexane, Rf: 0.5, KMnO$_4$ active). The reaction mixture was quenched using ice cold water (10 ml) and extracted in ethyl acetate (10 ml×2). The combined organic layer was dried over Na$_2$SO$_4$ and evaporated under reduced pressure to obtain 600 mg of crude Compound 7q. The crude compound was purified by silica column using 8% ethyl acetate in hexane as an eluent. The pure fractions were collected and evaporated under reduced pressure to obtain Compound 7q (170 mg, 46%) as a colorless oil. $^1$H NMR (300 MHz, DMSO-d) 5 ppm 0.99 (d, J=6.60 Hz, 3H), 1.38 (s, 3H) 3.25 (m, J=6.42, 2.02 Hz, 2H), 3.45-3.68 (m, 4H), 4.24 (d, J=6.60 Hz, 2H), 4.47 (m, J=5.69 Hz, 2H), 5.78-5.87 (d, 1H), 6.14-6.24 (dd, 1H); LCMS: 72% (215.4, M+H), RT=1.68 min.

Step 7. (Z)-4-methyl-5-((3-methyloxetan-3-yl) oxy) pent-2-enoic acid, Compound 9q To a stirred solution of Compound 7q (170 mg, 0.794 mmol) in THF (2 ml) and H$_2$O (0.5 ml) was added LiOH.H$_2$O (100 mg, 2.38 mmol) at room temperature. The reaction mixture was stirred at room temperature for 72 h. The progress of the reaction was monitored by TLC (70% EtOAc in hexane, Rf: 0.2, KMnO$_4$ active). The reaction mixture evaporated under reduced pressure and diluted with water (10 ml) and washed with 10% MeOH in DCM (5 ml×10). The aqueous layer was separated and acidified using 1 N HCl and adjusted to pH ~2. The crude product was extracted using 10% MeOH in DCM (10 ml×3). The organic layer was separated and dried over anhydrous sodium sulfate and evaporated under reduced pressure to obtain Compound 9q (119 mg, 75%) as a colorless oil. $^1$H NMR (400 MHz, DMSO-d$_6$) δ ppm 0.98 (d, J=6.80 Hz, 3H), 1.43 (s, 3H), 3.24 (d, J=6.36 Hz, 2H), 3.51-3.65 (m, 1H), 4.24 (d, J=6.36 Hz, 2H), 4.47 (t, J=5.81 Hz, 2H), 5.71-5.74 (dd, J=12, 0.77 Hz, 1H) 6.06-6.12 (dd, J=10, 9.76 Hz, 1H). 12.12-12.33 (br s, 1H); ELSD: 98.47% (201.1, M+H), RT=2.44 min; Z geometric isomer confirm by JJ coupling constant value of olefin bond: J=12, 10 Hz.

Part B:

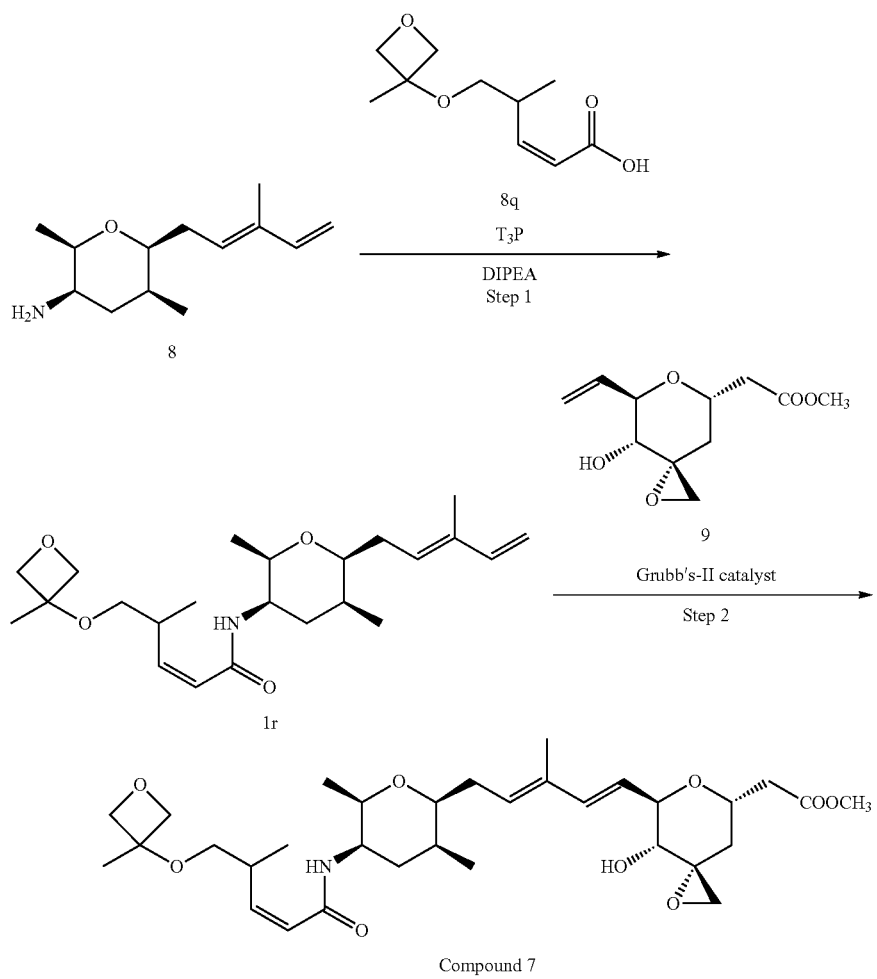

Step 1. (Z)—N-((2R, 3R, 5S, 6S)-2,5-dimethyl-6-((E)-3-methylpenta-2,4-dien-1-yl)tetrahydro-2H-pyran-3-yl)-4-methyl-5-((3-methyloxetan-3-yl)oxy)pent-2-enamide, Compound 1r To a stirred solution of Compound 8 (100 mg, 0.477 mmol), (Z)-4-methyl-5-((3-methyloxetan-3-yl)oxy)pent-2-enoic acid (Compound 1q) (95 mg, 0.477 mmol) in THF (5 ML) at 23° C., was added DIPEA (0.43 mL, 2.385 mmol) and T$_3$P (50% in EtOAc) (0.45 mL, 1.431 mmol). The reaction mixture was stirred at room temperature for 3 h. The reaction progress was monitored by TLC (50% EtOAc in hexane, R$_1$=0.5, UV visible). After completion, the reaction mixture was concentrated in vacuo to obtain the crude compound. The crude residue was purified by flash chromatography (10 to 50% EtOAc in hexanes) on silica (100-200 mesh) to afford Compound 1r (75 mg, 40.10%) as a pale yellow liquid. $^1$H NMR (400 MHz, chloroform-d) δ ppm 6.37 (dd, J=17.38, 10.52 Hz, 1H) 6.03-6.17 (m, 1H) 5.68-5.85 (m, 2H) 5.46 (br t, J=7.14 Hz, 1H) 5.11 (d, J=17.44 Hz, 1H) 4.96 (d, J=10.68 Hz, 1H) 4.61-4.75 (m, 2H) 4.28-4.37 (m, 2H) 3.85-4.05 (m, 1H) 3.47-3.73 (m, 4H) 3.33-3.42 (m, 1H) 3.14-3.25 (m, 1H) 2.32-2.45 (m, 1H) 2.19-2.30 (m, 1H) 1.87-2.07 (m, 3H) 1.49-1.64 (m, 12H) 1.24-1.32 (m, 3H) 1.16-1.22 (m, 2H) 1.10-1.15 (m, 2H) 1.05 (td, J=4.82, 2.23 Hz, 5H) 0.99 (d, J=7.30 Hz, 2H); LCMS: 89.55% (392.13, M+H), RT: 2.21 min.

Step 2. Methyl 2-((3R, 5S, 7R, 8R)-7-((1E, 3E)-5-((2S, 3S, 5R, 6R)-3,6-dimethyl-5-((Z)-4-methyl-5-((3-methyloxetan-3-yl)oxy)pent-2-enamido)tetrahydro-2H-pyran-2-yl)-3-methylpenta-1,3-dien-1-yl)-8-hydroxy-1,6-dioxaspiro[2.5]octan-5-yl)acetate, Compound 7

To a stirred solution of Compound 1r (70 mg, 0.178 mmol) in DCM (10 ml) at 23° C., Compound 9 (61 mg, 0.268 mmol) and Grubbs-II catalyst (45 mg, 0.053 mmol) were added under a nitrogen atmosphere. The reaction mixture was stirred at 40° C. for 5 h. The reaction progress was monitored by TLC (50% EtOAc in hexanes, R$_F$=0.1, UV visible). The reaction mixture was filtered through celite, washed with DCM (5 ml) and the filtrate was concentrated under reduced pressure to obtain the crude compound. The crude residue was purified by preparative HPLC [Mobile Phase A: 10 mm ABC; Mobile Phase B: acetonitrile; Column: X-bridge (150×19) mm, 5u; Method: (T/% B): 0/30, 2/30, 20/60, 20.50/90, 22/90; Flow: 18 ml/min; Solubility: ACN+THF+water; Ambient temperature]. The collected fractions were lyophilized to afford Compound 7 (3.5 mg) as a white solid. $^1$H NMR (400 MHz, DMSO-$d_6$) δ ppm 7.57 (br dd, J=12.39, 8.00 Hz, 1H) 6.28 (br d, J=15.78 Hz, 1H) 5.99-6.08 (m, 1H) 5.68-5.78 (m, 1H) 5.58 (br dd, J=16.00, 5.04 Hz, 1H) 5.52 (br t, J=6.91 Hz, 1H) 5.04 (br d, J=5.92 Hz, 1H) 4.44-4.53 (m, 2H) 4.19-4.32 (m, 4H) 3.77 (ddt, J=15.65, 12.91, 6.55, 6.55 Hz, 1H) 3.65 (br d, J=5.92 Hz, 2H) 3.60 (s, 3H) 3.46-3.54 (m, 1H) 3.23-3.27 (m, 3H) 3.20 (dd, J=6.25, 2.52 Hz, 2H) 2.76 (d, J=5.26 Hz, 1H) 2.67 (dt, J=4.00, 2.27 Hz, 3H) 2.58-2.65 (m, 1H) 2.15-2.36 (m, 3H) 1.77-1.91 (m, 2H) 1.70 (s, 3H) 1.65 (br dd, J=6.47, 3.40 Hz, 3H) 1.53 (br dd, J=12.93, 3.73 Hz, 1H) 1.42 (s, 3H) 1.03-1.11 (m, 3H) 0.91-0.99 (m, 6H); LCMS: 95.81% (592.24, M+H), RT: 3.72 min and 3.74 min.

Example 8

Synthesis of (Z)-5-(((2R, 3R, 5S, 6S)-6-((2E, 4E)-5-((3R,4R,5R,7S)-7-(2-((2,5-dioxopyrrolidin-1-yl)oxy)-2-oxoethyl)-4-hydroxy-1,6-dioxaspiro[2.5]octan-5-yl)-3-methylpenta-2,4-dien-1-yl)-2,5-dimethyltetrahydro-2H-pyran-3-yl)amino)-5-oxopent-3-en-2-yl 4-fluorobenzoate, Compound 10

Part A:

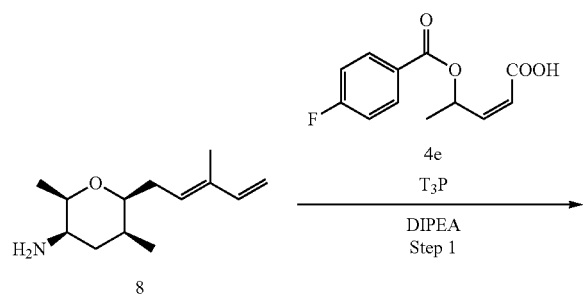

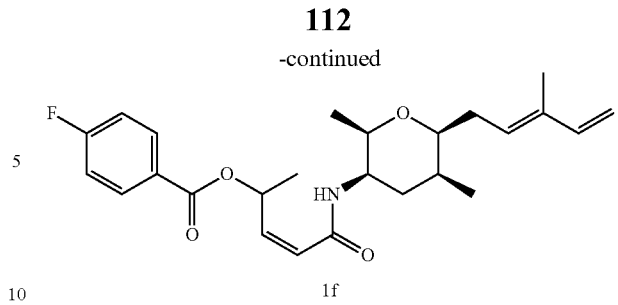

Step 1. (Z)-5-((2R, 3R, 5S, 6S)-2,5-dimethyl-6-((E)-3-methylpenta-2,4-dienyl)tetrahydro-2H-pyran-3-ylamino)-5-oxopent-3-en-2-yl 4-fluorobenzoate, Compound 1f To a stirred solution of Compound 8 (400 mg, 1.91 mmole) at room temperature were added Compound 4e (273 mg, 1.14 mmole) in THF (12 ml), DIPEA (1.23 g, 9.55 mmole), and T$_3$P (50% in EtOAc) (1.82 g) at RT. The reaction mixture was stirred at RT for 4 h. The reaction progress was monitored by TLC (30% EtOAc in petroleum ether, R$_F$=0.2, PMA active). The reaction mixture was concentrated under reduced pressure to obtain the crude product. The crude product was purified by column chromatography (100-200 silica gel/eluent 10% EtOAc in petroleum ether) to give Compound 1f (220 mg) as a colorless gum. $^1$H NMR (400 MHz, chloroform-d) δ ppm 0.99-1.08 (m, 3H) 1.11-1.20 (m, 3H) 1.36-1.44 (m, 3H) 1.47-1.55 (m, 5H) 1.69-1.85 (m, 4H) 1.89-2.03 (m, 2H) 2.19-2.32 (m, 1H) 2.34-2.49 (m, 1H) 3.49-3.59 (m, 1H) 3.62-3.75 (m, 1H) 3.91-4.04 (m, 1H) 4.87-5.01 (m, 1H) 5.11 (d, J=17.44 Hz, 1H) 5.47 (br d, J=3.81 Hz, 1H) 5.76 (ddd, J=11.61, 5.94, 1.20 Hz, 1H) 5.88-6.09 (m, 2H) 6.18-6.58 (m, 3H) 7.05-7.16 (m, 2H) 7.99-8.10 (m, 2H); LCMS: 87.8% (430.07, M+H), RT: 2.50 min and 2.52 min.

Part B:

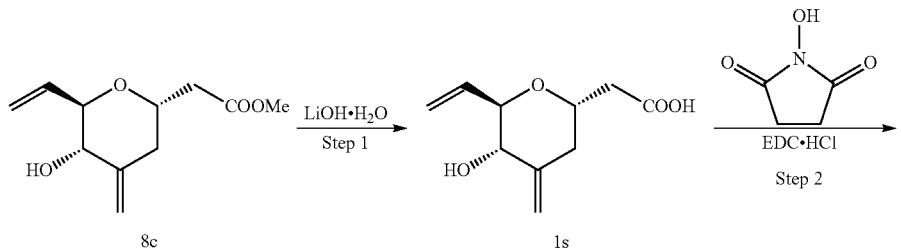

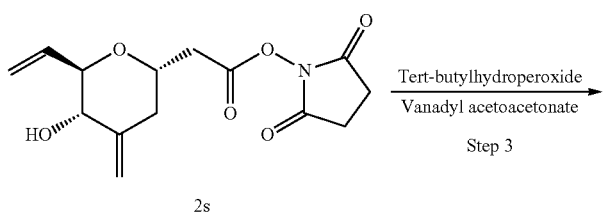

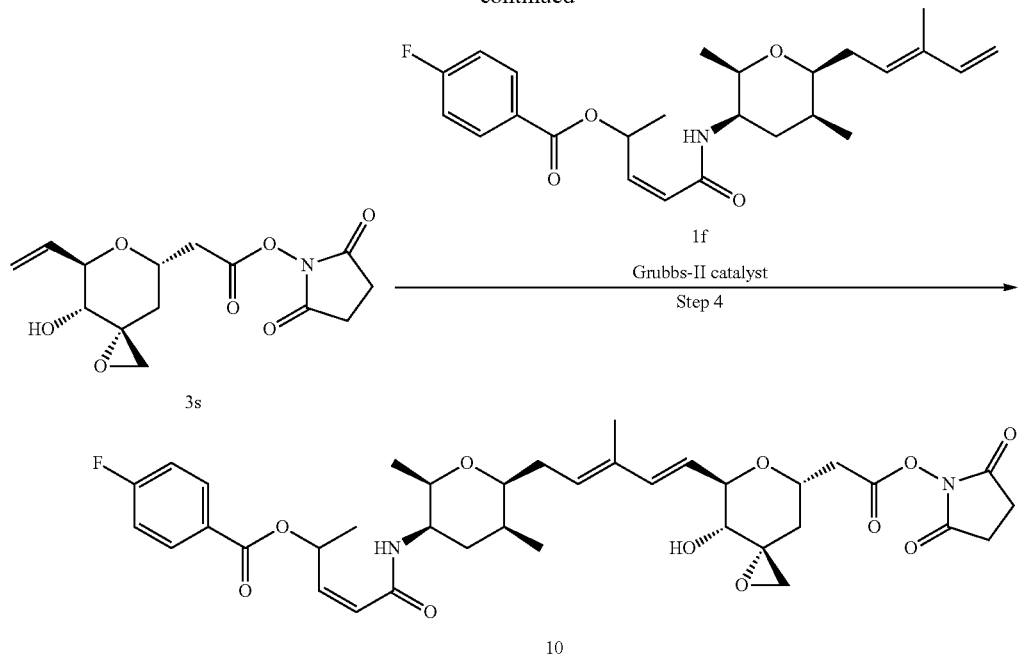

Step 1. 2-((2S, 5S, 6R)-5-hydroxy-4-methylene-6-vinyltetrahydro-2H-pyran-2-yl)acetic acid, Compound 1s To a stirred solution of Compound 8c (600 mg, 2.83 mmol) in THF (9 mL) and water (1 mL) at 23° C. was added lithium hydroxide monohydrate (178 mg, 4.24 mmol). The reaction mixture was stirred at 23° C. for 16 h. The progress of the reaction was monitored by TLC (10% MeOH in DCM, $R_F$: 0.1, PMA visible). After completion, the THF was evaporated under reduced pressure. The resulting residue was acidified with saturated citric acid, extracted with 10% MeOH in DCM (3×50 mL), dried over anhydrous sodium sulfate, filtered, and concentrated in vacuo to afford Compound 1s (200 mg) as a pale yellow liquid. $^1$H NMR (300 MHz, DMSO-$d_6$) δ ppm 12.15 (br s, 1H) 5.87 (ddd, J=17.33, 10.73, 4.95 Hz, 1H) 5.11-5.31 (m, 3H) 5.05 (s, 1H) 4.83 (s, 1H) 4.14-4.26 (m, 1H) 3.83-3.94 (m, 1H) 3.68 (t, J=6.24 Hz, 1H) 3.17 (d, J=5.14 Hz, 1H) 2.43 (dd, J=6.97, 4.03 Hz, 2H) 2.20-2.38 (m, 2H).

Step 2. 2,5-dioxopyrrolidin-1-yl 2-((2S, 5S, 6R)-5-hydroxy-4-methylene-6-vinyltetrahydro-2H-pyran-2-yl)acetate, Compound 2s To a stirred solution of Compound 1s (200 mg, 1.008 mmol) and 1-hydroxypyrrolidine-2,5-dione (174 mg, 1.513 mmol) in DCM (10 mL) at 23° C. was added EDC hydrochloride (289 mg, 1.513 mmol). The mixture was stirred at 23° C. for 12 h. The progress of the reaction was monitored by TLC (TLC system: 50% EtOAc in hexane, $R_f$=0.4, PMA visible). After completion of the reaction, the solvent was concentrated under reduced pressure to obtain the crude product. This residue was purified by flash chromatography (20 to 50% EtOAc in hexane) on silica (100-200 mesh) to afford Compound 2s (180 g, 60.60%) as a pale yellow liquid. $^1$H NMR (400 MHz, chloroform-d) δ ppm 5.87 (ddd, J=17.44, 10.79, 5.99 Hz, 1H) 5.31-5.44 (m, 2H) 5.15 (s, 1H) 5.02 (d, J=0.98 Hz, 1H) 4.37 (qd, J=6.68, 4.36 Hz, 1H) 4.14-4.22 (m, 1H) 3.96 (t, J=5.34 Hz, 1H) 2.89 (dd, J=6.54, 3.27 Hz, 2H) 2.79-2.86 (m, 4H) 2.51-2.59 (m, 1H) 2.39-2.48 (m, 1H) 2.30 (d, J=5.99 Hz, 1H); LCMS: 79.10% (296.09, M+H), RT: 1.37 min.

Step 3. 2,5-dioxopyrrolidin-1-yl 2-((3R, 5S, 7R, 8R)-8-hydroxy-7-vinyl-1,6-dioxaspiro[2.5]octan-5-yl)acetate, Compound 3s To a solution of Compound 2s (180 mg, 0.609 mmol) in DCM (10 mL) at −20° C. was added vanadyl acetoacetonate (16 mg, 0.060 mmol) and tert-butyl hydroperoxide (TBHP) (5.5 M in decane) (0.22 mL). The resulting mixture was then warmed to 0° C. and stirred for 2 h. After 2 h, the reaction mixture was warmed to 23° C. and stirred for 18 h. After completion of the reaction as determined by TLC (50% EtOAc in hexane, $R_1$=0.2, PMA visible), the solvent was concentrated under reduced pressure to obtain the crude product. The crude residue was purified by flash chromatography (30 to 60% EtOAc in hexane) on silica (100-200 mesh) to afford Compound 3s (110 mg, 58.20%) as a pale yellow liquid. $^1$H NMR (400 MHz, chloroform-d) δ ppm 6.00 (s, 1H) 5.44 (dt, J=17.41, 1.54 Hz, 1H) 5.31-5.36 (m, 1H) 4.51-4.59 (m, 1H) 4.20-4.27 (m, 1H) 3.48-3.55 (m, 1H) 3.10-3.20 (m, 1H) 2.96-3.06 (m, 2H) 2.79-2.90 (m, 6H) 2.70 (d, J=4.47 Hz, 1H) 2.05 (t, J=2.34 Hz, 1H) 1.90-2.01 (m, 2H).

Step 4. (Z)-5-(((2R, 3R, 5S, 6S)-6-((2E, 4E)-5-((3R,4R,5R,7S)-7-(2-((2,5-dioxopyrrolidin-1-yl)oxy)-2-oxoethyl)-4-hydroxy-1,6-dioxaspiro[2.5]octan-5-yl)-3-methylpenta-2,4-dien-1-yl)-2,5-dimethyltetrahydro-2H-pyran-3-yl)amino)-5-oxopent-3-en-2-yl 4-fluorobenzoate, Compound 10

To a stirred solution of Compound 1f (100 mg, 0.233 mmol) in DCM (10 ml) at 23° C., Compound 3s (108 mg, 0.502 mmol) and Grubbs-II catalyst (59 mg, 0.069 mmol)

were added under a nitrogen atmosphere. The reaction mixture was stirred at 40° C. for 6 h. The reaction progress was monitored by TLC (50% EtOAc in hexane, $R_F$=0.1, UV visible). The reaction mixture was filtered through celite and washed with DCM (5 ml). The filtrate was concentrated under reduced pressure to obtain the crude product. LCMS analysis showed a yield of 15% of the desired product along with unreacted Compound 1f. The crude compound was purified by preparative HPLC. The collected fractions were lyophilized to afford Compound 10 (11 mg) as a white solid (7% yield). The product was isolated as a mixture of diastereomers by preparative HPLC [Mobile Phase A: 0.1% formic acid, Mobile Phase B: acetonitrile; Column: Synergy polar (250×21.2) mm, 4u; Method: (T/% B): 65:35 (isocrotic); Flow: 18 ml/min; Solubility: ACN+THF+water, Ambient temperature]. $^1$H NMR (400 MHz, chloroform-d) δ ppm 8.05 (ddd, J=8.60, 5.65, 2.41 Hz, 2H) 7.10 (t, J=8.55 Hz, 2H) 6.36-6.58 (m, 2H) 5.91-6.08 (m, 2H) 5.76 (dd, J=11.62, 5.48 Hz, 1H) 5.64 (dd, J=15.78, 5.92 Hz, 1H) 5.54 (br s, 1H) 4.48-4.60 (m, 1H) 4.23 (br t, J=6.36 Hz, 1H) 3.98 (br dd, J=5.26, 2.85 Hz, 1H) 3.68 (q, J=6.28 Hz, 1H) 3.54 (br t, J=7.67 Hz, 2H) 3.02-3.20 (m, 2H) 2.99 (d, J=4.60 Hz, 1H) 2.75-2.90 (m, 4H) 2.69 (d, J=4.60 Hz, 1H) 2.34-2.48 (m, 1H) 2.11-2.31 (m, 2H) 1.86-2.05 (m, 4H) 1.73-1.84 (m, 4H) 1.53 (br d, J=6.58 Hz, 3H) 1.17 (t, J=6.14 Hz, 3H) 1.04 (t, J=7.56 Hz, 3H); LCMS: 96.58% (713.27, M+H), RT: 4.63 min & 4.67 min.

Example 9

Synthesis of ADCs with Trastuzumab Antibody, Compound 11, and Palivizumab Antibody, Compound 12

Lyzer™ dialysis devices (ThermoFisher Scientific, Waltham, Mass.). Dimethyl acetamide (DMA; MP Biomedicals, Santa Ana, Calif.) was added to each formulation to bring the total organic content to 10% v/v. Each antibody was then reacted with 8 molar equivalents of Compound 10 from a 20 mM stock in DMA. The conjugation reactions were allowed to incubate on a rocker table for 2 h at room temperature. To quench unreacted Compound 10, 80 molar equivalents of tris-buffered saline (TBS; Sigma) were added and incubated with rocking at room temperature for 1 h. The ADCs were purified and the buffer exchanged into storage buffer [10 mM histidine (VWR), 50 mM trehalose (Acros Organics, Waltham, Mass.), pH 6.0] using Sephadex™ PD-10 G-25 desalt columns (GE Healthcare, Chicago, Ill.). Final recoveries and concentrations of ADCs were determined using UV/Vis spectrophotometry (4 mL @ 5.0 mg/mL Compound 11; 3.2 mL @ 1.1 mg/mL Compound 12). Drug-to-antibody ratio (DAR) was determined by UV/is spectrophotometry and confirmed using LC-MS mass shift (3.5 for Compound 11; 2.8 for Compound 12). Aggregation analysis was performed for each ADC using size exclusion chromatography (SEC) on a Superdex® Increase 5/150 GL column (GE Healthcare) to ensure integrity of monomeric species (>98% for Compound 11; >99% for Compound 12). Endotoxin content for each ADC was confirmed to be ≤1 EU/mL using a ToxinSensor™ Gel Clot Assay (GenScript; Georgetown, Grand Cayman, Cayman Islands).

A similar procedure is followed to synthesize additional ADCs of the disclosed invention, where amide linkages to lysine residues form the drug conjugate. Different toxins may be substituted for Compound 2 and linkers other than amides may be utilized to produce ADCs. Further, antibod-

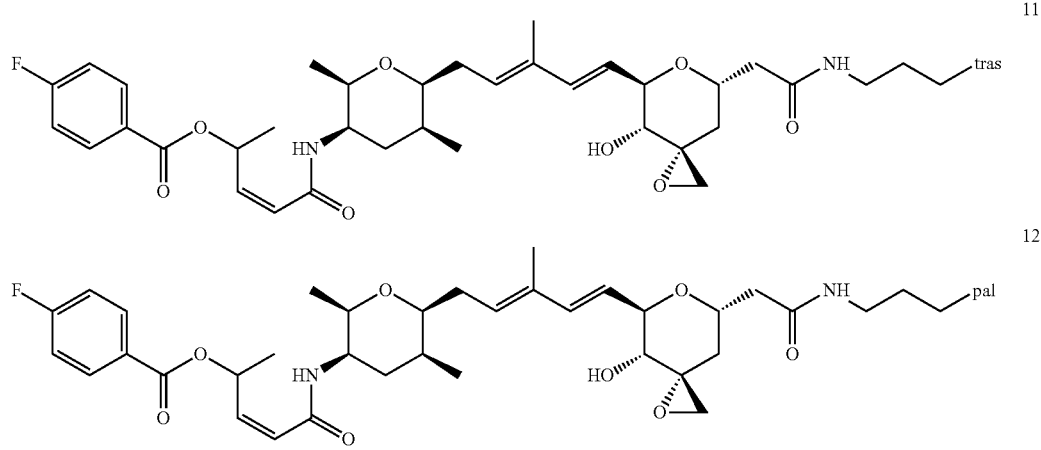

Compound 11, Compound 10 conjugated to trastuzumab, and Compound 12, Compound 10 conjugated to palivizumab, were synthesized in a procedure adapted from Arlotta, et al. (*Antibodies*, 2018, 7(1):6). Twenty-one mg commercial trastuzumab (Herceptin®; Genentech; Pharmaceutical Buyers Inc., New Hyde Park, N.Y.) and 5 mg palivizumab (Synagis®; MedImmune; Pharmaceutical Buyers Inc.) were prepared to concentrations of 3 mg/mL in the formulations listed in the original manufacturer's package insert and dialyzed into conjugation buffer [(50 mM borate) (Alfa Aesar, Haverill, Mass.), 50 mM NaCl (Sigma; St. Louis, Mo.), 2 mM EDTA (Sigma), pH 8.5] using Slide-A- ies other than trastuzumab and palivizumab may be substituted depending upon the cancer cells targeted.

Example 10

In Vitro Cell Assays

On Day 1, 96-well plates are seeded with cancer cell lines SKBR3, HCC1954, MCF7, and MDAMB231 in media at a predetermined cell number/well. Thailanstatin A is used as a positive toxic control test compound for each cell line and diluent only as a negative control. The plates are incubated in a 37° C. humidified CO₂ incubator for 20 hrs. On Day 2, dilutions of the test compounds to be tested are prepared. Initial working stocks of the samples are made in an appropriate media. A 1/3 serial dilution in media is then prepared for each test compound. 5 ul of the dilution are added into each well of ~100 ul cells. Final sample concentrations range from nM to pM (as ⅓ serial dilutions). Duplicate/or triplicate data points are obtained for all samples. Three/two samples per plate using wells in rows B, C, D, E, F, G are produced. The plates are then Incubated in a 37° C. humidified CO₂ incubator for 72 hrs.

On Day 5, cell viability is read using Cell-Titer Glo® reagent using the following procedure. The media is aspirated from the 96-well plate. 100 ul of Cell-Titer Glo reagent (Promega, Inc., Madison, Wis.) is added to each well. The plates are incubated at RT for 10 min. The resulting luminescence is read using a Tecan Ultra® plate reader.

The resulting data are analyzed and plotted as Percent Viability vs. Concentration (nM). The resulting curves are fit using nonlinear regression. The $IC_{50}$ for each test compound is then calculated and tabulated.

The toxicity of the compounds of the invention may be determined in a similar fashion using the following cancer cell lines in the above-described assay: leukemia cell lines including CCRF-CEM, HL-60 (TB), K-562, MOLT-4, RPMI-8226, and SR; non-small cell lung cancer cell lines including A549/ATCC, EKVX, HOP-62, HOP-92, NCI-H226, NCI-H23, NCI-H322M, NCI-H460, and NCI-H522; colon cancer cell lines including COLO 205, HCC-2998, HCT-116, HCT-15, HT29, KM12, and SW-620; CNS cancer cell lines including SF-268, SF-539, SNB-19, SNB-75, and U251; melanoma cell lines including LOX IMVI, MALME-3M, M14, SK-MEL-2, SK-MEL-28, SK-MEL-5, UACC-257, and UACC-62; ovarian cancer cell lines including IGROV1, OVCAR-3, OVCAR-4, OVCAR-5, OVCAR-8, and SK—OV-3; renal cancer cell lines including 786-0, A498, ACHN, CAKI-1, RXF 393, SN 12C, TK-10, and UO-31; breast cancer cell lines including MCF7, HS 578T, MDA-MB-435, BT-549, T-47D, and MDA-MB-468; and prostate cancer cell lines PC-3 and DU-145.

Example 11

In Vitro Cell Assays

Alternatively, the in vitro cytotoxicity of the compounds of the invention may be measured as described in this example. 180 µl of HCT 116 cells (ATCC, Cat # CCL-247) in McCoy's 5a Medium Modified (Sigma-Aldrich®, St. Louis, Mo.)+10% fetal bovine serum were seeded at a density of 5,000 cells/well in a white opaque 96-well plate and incubated for 24 hours at 370° C. in a 5% CO₂ incubator. Twenty-four hours post cell seeding, 20 µl of 100× test compounds were diluted such that the final concentrations of the test compounds were in µM concentration. Half log dilutions were used, starting from 10 µM through 0.0001 µM. Puromycin and untreated cells were used as positive controls. The cells were incubated with the compounds for 72 hours at 370° C. in a 5% CO₂ incubator. After 72 hrs, 100 µl/well of CellTiter-Glo® Luminescent Cell Viability Assay reagent (Promega, Inc., Madison, Wis.; Cat. # G7573) was added to the plates and incubated at room temperature for 30 minutes. The luminescence signals were captured using EnVision 2105 Multimode Plate Reader (PerkinElmer, Waltham, Mass.). The data were analyzed using non-linear regression curve fit (sigmoidal dose response) in GraphPad Prism software (GraphPad Software, La Jolla, Calif.) by plotting the concentration of drug on the X-axis and the mean % inhibition values on the Y-axis.

Table 1 summarizes the cytotoxicity observed for the indicated toxin compounds.

TABLE 1

| Cmpd No. | Structure | $IC_{50}$, µM |
|---|---|---|
| 1 | 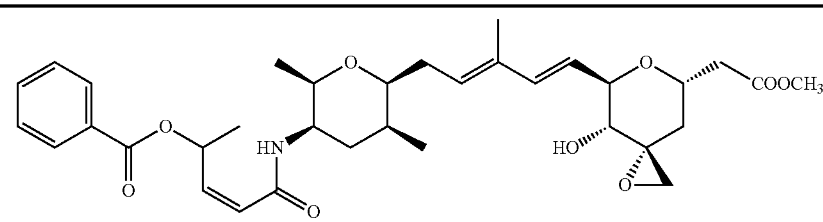 | 0.019 |
| 2 | 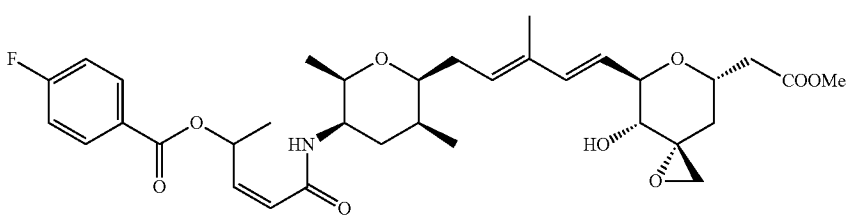 [SMILES: COC(=O)C[C@@H]1C[C@@]2(CO2)[C@H](O)[C@@H](/C=C/C(C)=C/C[C@@H]2O[C@H](C)[C@H](NC(=O)/C=C\C(C)OC(=O)c3ccc(F)cc3)C[C@@H]2C)O1] | 0.007 |
| 3 | 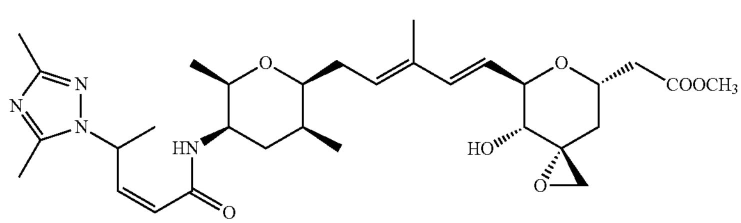 [SMILES: COC(=O)C[C@@H]1C[C@@]2(CO2)[C@H](O)[C@@H](/C=C/C(C)=C/C[C@@H]2O[C@H](C)[C@H](NC(=O)/C=C\C(C)n3nc(C)nc3C)C[C@@H]2C)O1] | 0.39 |

TABLE 1-continued

| Cmpd No. | Structure | IC$_{50}$, μM |
|---|---|---|
| 4 | 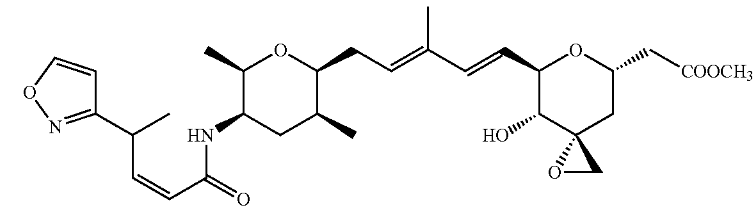 [SMILES: COC(=O)C[C@@H]1C[C@@]2(CO2)[C@H](O)[C@@H](/C=C/C(C)=C/C[C@@H]2O[C@H](C)[C@H](NC(=O)/C=C\C(C)c3ccon3)C[C@@H]2C)O1] | 0.33 |
| 5 | 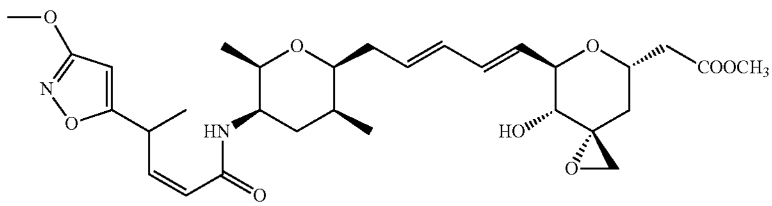 [SMILES: COC(=O)C[C@@H]1C[C@@]2(CO2)[C@H](O)[C@@H](/C=C/C=C/C[C@@H]2O[C@H](C)[C@H](NC(=O)/C=C\C(C)c3cc(OC)no3)C[C@@H]2C)O1] | 0.31 |
| 6 | 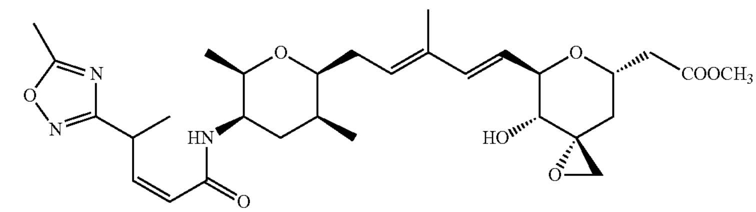 [SMILES: COC(=O)C[C@@H]1C[C@@]2(CO2)[C@H](O)[C@@H](/C=C/C(C)=C/C[C@@H]2O[C@H](C)[C@H](NC(=O)/C=C\C(C)c3noc(C)n3)C[C@@H]2C)O1] | 0.02 |
| 7 | 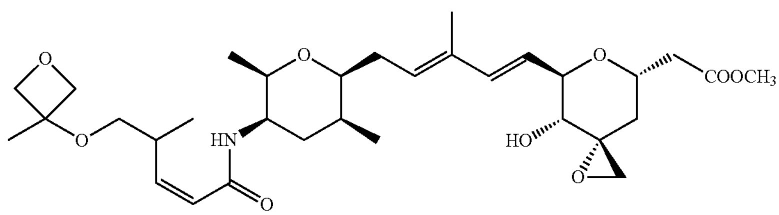 [SMILES: COC(=O)C[C@@H]1C[C@@]2(CO2)[C@H](O)[C@@H](/C=C/C(C)=C/C[C@@H]2O[C@H](C)[C@H](NC(=O)/C=C\C(C)COC3(C)COC3)C[C@@H]2C)O1] | 0.3 |
| Puromycin | | ~0.25 |

Example 12

In Vitro Cytotoxicity of Toxin Compounds

Various cancer cell lines were obtained from the American Type Culture Collection (ATCC®). The cells were cultured in a humidified 5% $CO_2$ incubator in a media consisting of RPMI 1640, L-glutamine, and 10% FBS. The cells were passaged as needed using standard tissue culture techniques. The cells were harvested and plated out into 96-well tissue culture treated plates at a density of 5000 cells per well. After allowing the cells to equilibrate for ~24 hr in a humidified 5% $CO_2$ incubator, the cells were treated with the test compounds at the indicated concentrations. The cells were exposed to the test compounds for three days with no media change. After the treatment period, CellTiter-Glo® Luminescent Cell Viability Assay reagent solution (Promega, Inc., Madison, Wis.; Cat. # G7573) was introduced to each well. The Cell TiterGlo-containing plates were then read on a SpectroMax® iD3 Multi-Mode Microplate reader (Molecular Devices, LLC, San Jose, Calif.). The degree of luminescence was dictated by the abundance of live cells. Cytotoxic 50% inhibitory concentrations (IC$_{50}$) were calculated using GraphPad Prism 7.0 (GraphPad Software, La Jolla, Calif.) nonlinear regression analysis.

The following tables summarize the cytotoxicity (IC$_{50}$), nM, observed for the specified toxin compounds on the indicated cancer cell lines, NCI-H23, DU145, SW480, SKOV3, A549, HT29, SK-MES-1, SKBR3, HCT116, MCF7, N87, and A431 (ATCC designations). Table 2 gives the cytotoxicity for Compounds 2, 4, and 6.

TABLE 2

| | IC$_{50}$, nM | | |
|---|---|---|---|
| Cell Line | Cmpd 2 | Cmpd 4 | Cmpd 6 |
| NCI-H23 | 1.3 | 0.2 | 0.4 |
| DU145 | 27.5 | 1.9 | 3.3 |
| SW480 | 20.2 | 2.2 | 2.7 |
| SKOV3 | 57.2 | 6.7 | 9.7 |
| A549 | 38.3 | 2.8 | 4.8 |
| HT29 | 22.5 | 1.3 | 2.7 |
| SK-MES-1 | 113.2 | 7.5 | 9.3 |
| SKBR3 | 166.2 | 9.5 | 12.3 |
| HCT116 | 8.9 | 1.0 | 2.0 |
| MCF7 | 32.4 | 2.1 | 3.8 |
| N87 | 14.9 | 1.6 | 1.4 |
| A431 | 9.1 | 0.7 | 1.8 |

Table 3 shows the cytotoxicity of Compounds 1 through 7 on two human pancreatic cancer cell lines, PANC 10.05 and PANC 05.04 using Thailanstatin A as a positive control.

TABLE 3

| Compound | PANC 10.05 IC$_{50}$, nM | PANC 05.04 IC$_{50}$, nM |
|---|---|---|
| 1 | 65 | 22 |
| 2 | 21 | 2 |
| 3 | >2000 | 435 |
| 4 | 7.19 | 4 |
| 5 | 19.91 | 12 |
| 6 | 10.35 | 7 |
| 7 | 98.44 | 22 |
| Thailanstatin A | 4 | 3 |

Table 4 gives the cytotoxicity data for Compounds 2, 4, and 6 on the indicated cancer cell lines, HL60, KG-1, NCI-H69, SK-MEL-1, HEL-92.1.7, and K562 (ATCC designations).

TABLE 4

| Cell line | Cmpd 2 IC$_{50}$, nM | Cmpd 4 IC$_{50}$, nM | Cmpd 6 IC$_{50}$, nM |
|---|---|---|---|
| HL60 | 0.08 | 0.05 | 0.04 |
| KG-1 | NA | NA | NA |
| NCI-H69 | 0.96 | 0.63 | 0.21 |
| SK-MEL-1 | 3.26 | 0.42 | 0.78 |
| HEL-92.1.7 | 0.71 | NA | 0.03 |
| K562 | 0.58 | 0.11 | 0.09 |

Example 13

In Vitro Cytotoxicity of ADCs

In a similar procedure to that described in Example 12, the cytotoxicity of ADC Compound 11 was determined for the indicated cancer cell lines. Compound 12 was used as a negative control.

TABLE 3

| Cell Lines | IC$_{50}$ (nM) Compound 11 | IC$_{50}$ (nM) Compound 12 (Control) |
|---|---|---|
| SKBR3 | 0.1 | >10 |
| BT474 | 0.3 | >10 |
| N87 | 0.2 | >10 |

Example 14

In Vivo Efficacy Study in the Treatment of Subcutaneous NCI-N87 Human Gastric Cancer Xenografts in Female Balb/c Nude Mice A human gastric cancer xenograft model of cancer, NCI=N87 (ATCC® Accession No. CRL-5822m), was used to test the in vivo efficacy of the ADCs of the disclosed invention. 1×107 NCI-N87 tumor cells in 0.1 mL of phosphate-buffered saline (PBS) mixed with matrigel (1:1) were injected into the right flank of 6-to-8-week old female Balb/c nude mice. The date of tumor cell inoculation was designated Day 0, and tumor volume was measured twice per week. Tumor volumes were measured in two dimensions using a caliper, and the volume expressed in mm$^3$ using the formula: V=(L×W×W)/2, where V is tumor volume, L is tumor length (the longest tumor dimension) and W is tumor width (the longest tumor dimension perpendicular to L). When the mean tumor size reached 150-300 mm$^3$, the mice were randomized and segregated into 8 treatment groups.

The treatment groups were as follows, where "Q4d*4" means that four total doses of drug substance were administered with a four-day interval between each dose beginning at Day 6:

Group 1: Vehicle (PBS) alone; Q4d*4;
Group 2: 1 mg/kg Compound 11; Q4d*4
Group 3: 3 mg/kg Compound 11; Q4d*4;
Group 4: 3 mg/kg Compound 11; single dose at Day 6;
Group 5: 3 mg/kg Compound 12; Q4d*4;
Group 6: 10 mg/kg Compound 11; single dose at Day 6;
Group 7: 10 mg/kg Kadcyla; single dose at Day 6; and
Group 8: 3 mg/kg Kadcyla; Q4d*4.

Each of the eight groups were administered the indicated test article by i.v. injection. Vehicle (PBS) and Compound 12 were used as negative controls to interrogate the influence of the vehicle (PBS) and target independent effects of Compound 10 as an ADC-delivered molecule on the study. Kadcyla® (ado-trastuzumab emtansine; Genentech, South San Francisco, Calif.) was administered as a comparator and positive ADC control.

Tumor volume was measured in each mouse on Day 6, Day 9, Day 12, Day 15, Day 19, Day 21, Day 23, Day 25, Day 27, Day 29 and Day 31 post injection to determine the efficacy of each treatment in reducing tumor volume. Data analysis was performed using GraphPad Prism 7.04 software.

FIG. 1 shows a graphical representation of the data. Tables 3A and 3B present the numerical bases for FIG. 1 where Avg represents the average Tumor volume (mm$^3$). SEM represents the standard error of the mean, and N represents the number of individual animals in the study group.

TABLE 3A

| Study | Group 1-PBS | | | Group 2-Compound 11 1 mg/kg Q4*4 | | | Group 3-Compound 11 3 mg/kg Q4*4 | | | Group 4-Compound 11 3 mg/kg Singe Dose | | |
|---|---|---|---|---|---|---|---|---|---|---|---|---|
| Day | Avg | SEM | N | Avg | SEM | N | Avg | SEM | N | Avg | SEM | N |
| 6 | 219.71 | 8.84 | 10 | 221.01 | 9.97 | 10 | 219.59 | 11.46 | 10 | 219.61 | 14.21 | 10 |
| 9 | 353.91 | 24.17 | 10 | 301.87 | 18.21 | 10 | 267.49 | 22.43 | 10 | 270.86 | 13.17 | 10 |
| 12 | 459.41 | 37.54 | 10 | 252.57 | 18.38 | 10 | 149.93 | 16.1 | 10 | 144.28 | 10.36 | 8 |
| 15 | 532.93 | 37.77 | 10 | 220.94 | 20.09 | 10 | 90.57 | 8.72 | 10 | 95.6 | 9.75 | 8 |
| 19 | 795.77 | 50.18 | 10 | 160.47 | 21.52 | 10 | 47.4 | 5.09 | 10 | 67.02 | 7.28 | 8 |
| 21 | 935.06 | 85.4 | 10 | 133.73 | 19.18 | 10 | 38.36 | 3.2 | 10 | 73.54 | 12.65 | 8 |
| 23 | 1062.57 | 101.66 | 10 | 122.03 | 17.35 | 10 | 35.32 | 2.87 | 10 | 89.03 | 15.37 | 8 |
| 25 | 1302.11 | 137.59 | 10 | 127.53 | 21.6 | 10 | 32.6 | 2.74 | 10 | 93.14 | 15.4 | 8 |
| 27 | 1449.85 | 184.47 | 10 | 136.66 | 24.48 | 10 | 30.75 | 3.48 | 10 | 96.33 | 18.87 | 8 |
| 29 | 1691.02 | 236.08 | 10 | 136.61 | 26.16 | 10 | 26.81 | 2.83 | 10 | 90.24 | 15.32 | 8 |
| 31 | 2042.43 | 323.77 | 10 | 152.64 | 34.39 | 10 | 26.89 | 2.27 | 10 | 89.66 | 16.62 | 8 |

TABLE 3B

| Study | Group 5-Compound 12 3 mg/kg Q4*4 | | | Group 6-Compound 11 10 mg/kg Single Dose | | | Group 7-Kadcyla 10 mg/kg Single Dose | | | Group 8-Kadcyla 3 mg/kg Q4*4 | | |
|---|---|---|---|---|---|---|---|---|---|---|---|---|
| Day | Avg | SEM | N | Avg | SEM | N | Avg | SEM | N | Avg | SEM | N |
| 6 | 220.57 | 10.47 | 8 | 220.2 | 9.55 | 10 | 219.52 | 12.27 | 10 | 218.77 | 9.9 | 12 |
| 9 | 333.42 | 25.51 | 8 | 185.01 | 32.96 | 3 | 286.58 | 18.98 | 10 | 262.41 | 19.5 | 12 |
| 12 | 463.52 | 18.76 | 7 | | | 0 | 119.79 | 14.33 | 10 | 148.62 | 7.59 | 12 |
| 15 | 528.03 | 25.36 | 7 | | | 0 | 68.93 | 6.67 | 10 | 109.07 | 6.31 | 12 |
| 19 | 710.94 | 43.42 | 7 | | | 0 | 32.84 | 3.07 | 10 | 61.32 | 6.61 | 12 |
| 21 | 890.41 | 72.7 | 7 | | | 0 | 34.57 | 3.1 | 10 | 56.15 | 4.38 | 12 |
| 23 | 929.35 | 55.11 | 7 | | | 0 | 32.3 | 3.89 | 10 | 64.71 | 6.41 | 12 |
| 25 | 1046.29 | 95.49 | 7 | | | 0 | 31.49 | 2.48 | 10 | 63.69 | 7.53 | 12 |
| 27 | 1228.81 | 144.78 | 7 | | | 0 | 30.89 | 2.6 | 10 | 60.18 | 7.45 | 12 |
| 29 | 1395.89 | 211.42 | 7 | | | 0 | 29.62 | 2.81 | 10 | 53.7 | 5.34 | 12 |
| 31 | 1562.98 | 225.55 | 7 | | | 0 | 28.64 | 2.86 | 10 | 48 | 3.61 | 12 |

The results of these in vivo experiments demonstrated that mice that were treated with PBS vehicle alone (Group 1) or with Compound 12 (Group 5) showed no observable reduction in tumor volume subsequent to treatment. In fact, the tumors in these animals continued to increase over time. As expected, the positive control Kadcyla (Groups 7 and 8) reduced tumor volume. The in vivo efficacy of Compound 11 at multiple dose levels and schedules (Groups 2, 3, 4, and 6) was clearly demonstrated by a reduction in tumor volume. The degree of tumor volume reduction was similar to that observed in the Kadcyla groups.

Weight loss after initial dosing was observed in Groups 3, 4, 5 and 6; Compound 11 (3 mg/kg, Q4*4), Compound 11 (3 mg/kg, single dose), Compound 12 (3 mg/kg, Q4*4), and Compound 11 (10 mg/kg, single dose), respectively. Weight loss leading to death was observed in Groups 4, 5 and 6; Compound 11 (3 mg/kg, single dose), Compound 12 (3 mg/kg, s(Q4*4), and Compound 12 (10 mg/kg, single dose), respectively. The most severe effect was observed in Group 6, Compound 11 (10 mg/kg, single dose), where, on day 9, 10 out of the 10 mice making up the treatment group were discovered to have died. Two of 10 mice in Group 3, Compound 11 (3 mg/kg single dose), were found dead the next day despite hydration and diet-based intervention to attempt to reverse the severe weight loss (>15% starting body weight). One mouse in the Compound 12 Group 5 was found with 15.94% weight loss and was euthanized. The number and severity of adverse effects correlated with dose level of Compound 10 ADC administered and were observed with non-HER2 targeting Compound 12 as well as with HER2 targeting Compound 11. Therefore the weight loss and deaths were attributed to effects of increasing levels of the linker toxin Compound 10 in an ADC context.

All publications and patent applications mentioned in this specification are herein incorporated by reference to the same extent as if each individual publication or patent application were specifically and individually indicated to be incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of Formula (III):

$$T\text{-}L'\text{-}Ab \quad (III)$$

or a pharmaceutically acceptable salt thereof, wherein:
L' is a linker moiety;
T is a radical of Formula (I'):

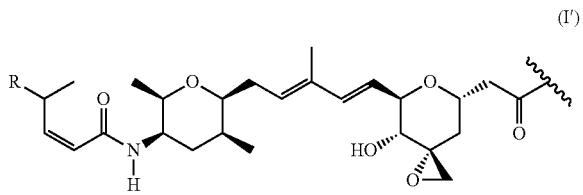

(I')

wherein:
R is selected from the group consisting of: $-(CH_2)_n-R^1$;
-5 to 6 membered heteroaryl, where heteroaryl is optionally substituted with one or more of halogen, $-CF_3$, $-C_{1-6}$alkyl, and $-O-C_{1-6}$alkyl;
$-C(R^2)=N-R^3$; $-CH(CF_3)NH(CH_2)_mCH_3$;
$-C(R^aR^b)NH(CH_2)_mCH_3$;
$-C(\text{halogen})=CH(CH_2)_mCH_3$; $-SO_2-NH(CH_2)_mCH_3$; $-O(CO)\text{-aryl}$; $-O(CO)-$ heteroaryl; $-NR^aR^b$; and $-NH\text{-heteroaryl}$;
wherein $R^1$ is $-O-CR^aR^b(CH_2)_mCH_3$ or $-N-CR^aR^b(CH_2)_mCH_3$;
wherein $R^a$ and $R^b$, together with the atoms to which they are joined, form a $C_{3-10}$ heterocyclyl ring;
$R^2$ is $-CN$ or $-NH(CH_2)_mCH_3$;
$R^3$ is $-(CH_2)_mCH_3$ or $-O-(CH_2)_mCH_3$;
each n is independently 1, 2, or 3;
each m is independently 0, 1, 2, or 3; and
Ab is an antibody.

2. The compound or salt according to claim 1, wherein R is selected from the group consisting of:

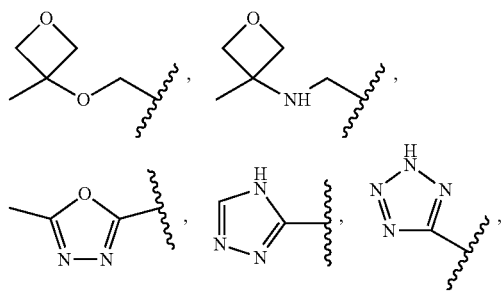

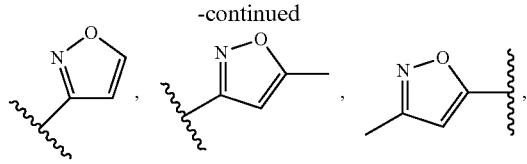,
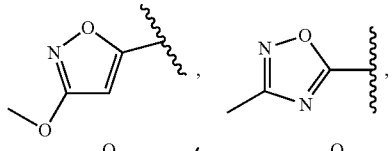,
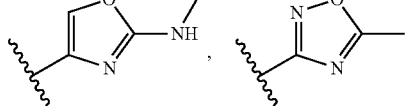,
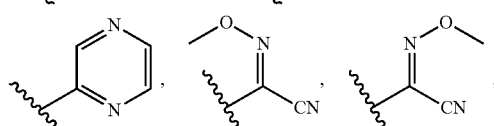,
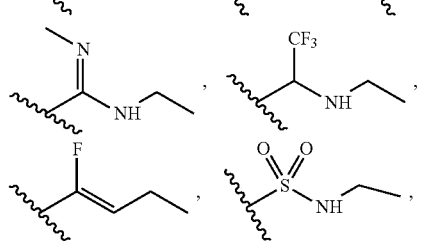,
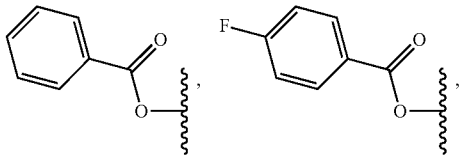,
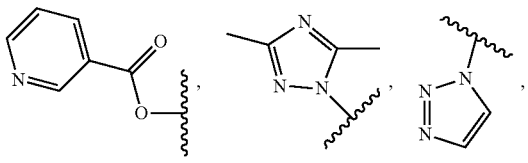, and
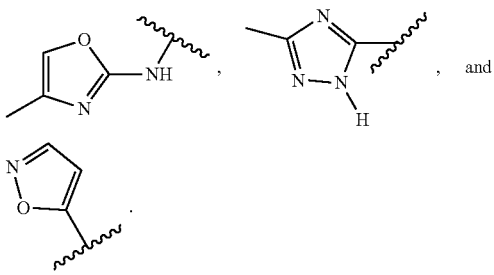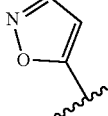.
3. The compound according to claim 1, wherein L' is selected from the group consisting of Formula (B¹), Formula (B²), Formula (B³), and Formula (B⁴):
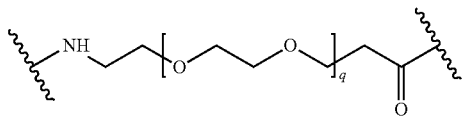 (B¹)
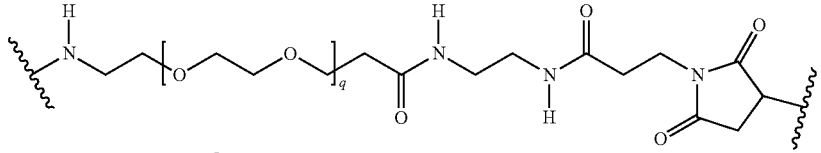 (B²)
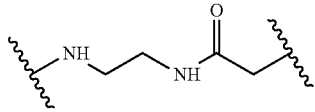 (B³)
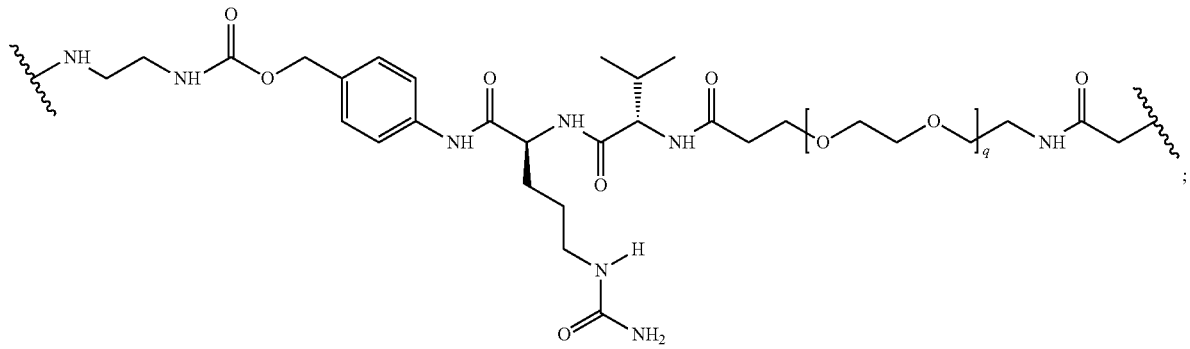 (B⁴);
wherein q is 3, 4, 5, 6, 7, 8, 9, or 10.

4. The compound or salt according to claim 1, wherein the compound of Formula (III) is selected from the group consisting of:
(C¹)
(C²)
(C³)
(C⁴)
(C⁵)
wherein q is 3, 4, 5, 6, 7, 8, 9, or 10; and n is 1, 2, 3, or 4.
5. The compound according to claim 1, having structure 11:
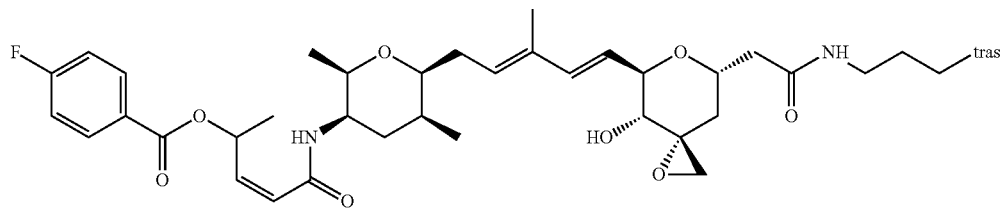
wherein tras is trastuzumab.

6. The compound or salt according to claim 1, wherein the antibody is selected from the group consisting of trastuzumab, pertuzumab, gemtuzumab, and vadastuximab.

7. The compound or salt according to claim 1, wherein the antibody binds to one or more tumor-associated antigens or cell-surface receptors.

8. The compound or salt according to claim 1, wherein the antibody binds to a tumor-associated antigen selected from the group consisting of HER2, CD33, CD70, MUC1/CanAg, MUC16, CD151 and ITGaV.

9. A pharmaceutical composition comprising a therapeutically effective amount of the compound or salt of claim 1 and a pharmaceutically acceptable diluent, carrier or excipient.

10. The method for the treatment of cancer comprising administering to a patient a therapeutically effective amount of the pharmaceutical composition of claim 9, wherein the cancer is selected from carcinomas of the bladder, breast, cervix, colon, endometrium, kidney, lung, esophagus, ovary, prostate, pancreas, skin, stomach and testes, leukemias and lymphomas.

11. A compound of Formula (III):

T-L'-Ab  (III)

or a pharmaceutically acceptable salt thereof, wherein:

L' is a linker moiety;

T is a radical of Formula (I'):

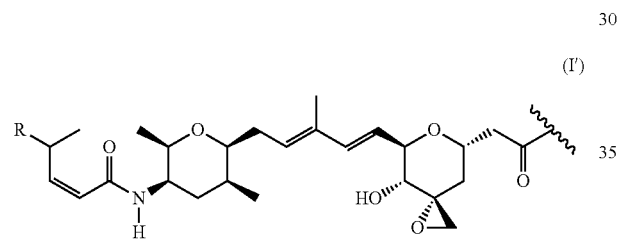

(I')

wherein:

R is selected from the group consisting of:

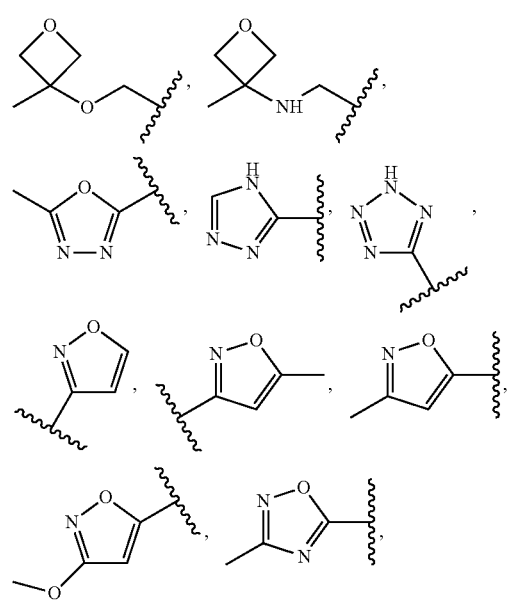

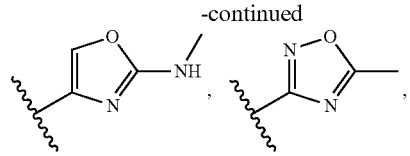

-continued

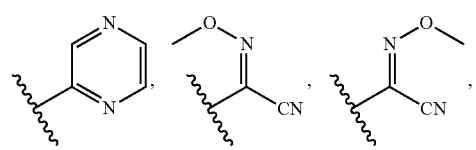

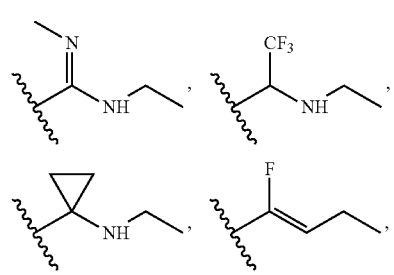

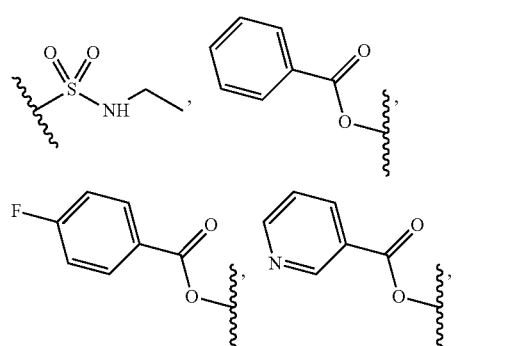

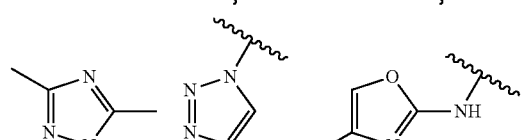

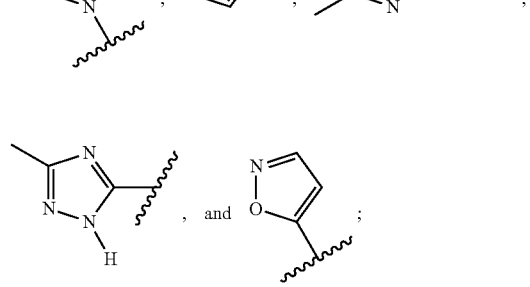

and

Ab is an antibody.

12. The method of claim 10 wherein the cancer is HER2-expressing breast cancer.

13. The compound of claim 1 of Formula (III):

T-L'-Ab  (III)

or a pharmaceutically acceptable salt thereof, wherein:
L' is a linker moiety;
T is a radical of Formula (I'):
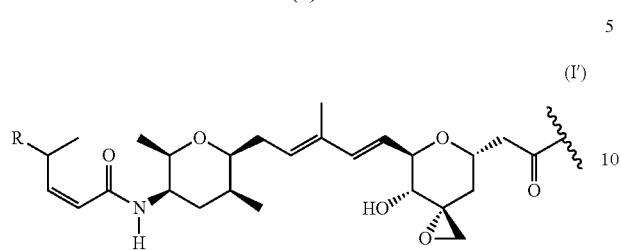
wherein:
R is selected from the group consisting of:
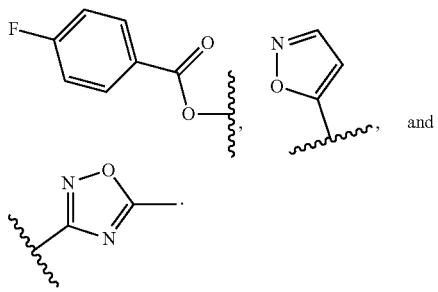, and
14. The compound of claim 13 wherein R is:
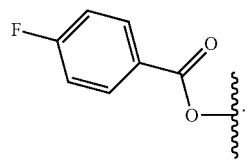 [SMILES: *OC(=O)c1ccc(F)cc1]
15. The compound of claim 13 wherein R is:
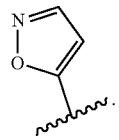
16. The compound of claim 13 wherein R is:
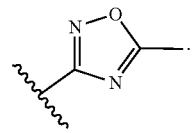
17. The compound of claim 13 wherein Ab is trastuzumab.
* * * * *